(12) United States Patent
Kamen et al.

(10) Patent No.: US 9,535,021 B2
(45) Date of Patent: *Jan. 3, 2017

(54) SENSOR APPARATUS SYSTEMS, DEVICES AND METHODS

(71) Applicant: DEKA Products Limited Partnership, Manchester, NH (US)

(72) Inventors: Dean Kamen, Bedford, NH (US); N. Christopher Perry, Manchester, NH (US); Jason A. Demers, Manchester, NH (US); Brian D. Tracey, Litchfield, NH (US); Arun D. Chawan, Manchester, NH (US); Kevin L. Grant, Litchfield, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/672,764

(22) Filed: Mar. 30, 2015

(65) Prior Publication Data

US 2015/0204807 A1 Jul. 23, 2015

Related U.S. Application Data

(63) Continuation of application No. 13/619,266, filed on Sep. 14, 2012, now Pat. No. 8,992,075, which is a
(Continued)

(51) Int. Cl.
*G01N 25/18* (2006.01)
(52) U.S. Cl.
CPC ..................... *G01N 25/18* (2013.01)
(58) Field of Classification Search
USPC .................. 374/44, 208, 148, 183
See application file for complete search history.

(56) References Cited

U.S. PATENT DOCUMENTS

| 1,693,526 A | 11/1928 | Owens |
| 2,529,028 A | 11/1950 | Landon |

(Continued)

FOREIGN PATENT DOCUMENTS

| CN | 2374187 Y | 4/2000 |
| CN | 1830494 A | 9/2006 |

(Continued)

OTHER PUBLICATIONS

Examination Report for EP Application No. 08726213.5 filed Sep. 24, 2009, published as EP 2131889 on Dec. 16, 2009, which Examination Report is dated May 16, 2012, and claims as pending for EP Application No. 08726213.5 as of May 16, 2012.
(Continued)

*Primary Examiner* — Mirellys Jagan
(74) *Attorney, Agent, or Firm* — Wolf, Greenfield & Sacks, P.C.

(57) ABSTRACT

A sensor apparatus and sensor apparatus system for use in conjunction with a cassette, including a disposable or replaceable cassette. In some embodiments, the cassette includes a thermal well for permitting the sensing of various properties of a subject media. The thermal well includes a hollow housing of a thermally conductive material. In other embodiments, the cassette includes sensor leads for sensing of various properties of a subject media. The thermal well has an inner surface shaped so as to form a mating relationship with a sensing probe. The mating thermally couples the inner surface with a sensing probe. In some embodiments, the thermal well is located on a disposable portion and the sensing probe on a reusable portion.

11 Claims, 62 Drawing Sheets

Related U.S. Application Data continuation of application No. 12/038,474, filed on Feb. 27, 2008, now Pat. No. 8,491,184, which is a continuation-in-part of application No. 11/871,821, filed on Oct. 12, 2007, now abandoned.

(60) Provisional application No. 60/921,314, filed on Apr. 2, 2007, provisional application No. 60/904,024, filed on Feb. 27, 2007.

(56) References Cited

U.S. PATENT DOCUMENTS

| | | |
|---|---|---|
| 2,741,099 A | 4/1956 | Beane |
| 2,816,514 A | 12/1957 | Freese |
| 3,016,563 A | 1/1962 | De Jong |
| 3,200,648 A | 8/1965 | Waggaman |
| 3,508,656 A | 4/1970 | Serfass et al. |
| 3,539,081 A | 11/1970 | Norton et al. |
| 3,656,873 A | 4/1972 | Schiff |
| 3,759,483 A | 9/1973 | Baxter |
| RE27,849 E | 12/1973 | Wortman |
| 3,827,561 A | 8/1974 | Serfass et al. |
| 3,882,861 A | 5/1975 | Kettering et al. |
| 3,936,729 A | 2/1976 | Winslow |
| 3,996,027 A | 12/1976 | Schnell et al. |
| 4,096,211 A | 6/1978 | Rameau |
| 4,096,859 A | 6/1978 | Agarwal et al. |
| 4,133,312 A | 1/1979 | Burd |
| 4,155,852 A | 5/1979 | Fischel et al. |
| 4,161,264 A | 7/1979 | Malmgren et al. |
| 4,266,814 A | 5/1981 | Gallagher |
| 4,267,040 A | 5/1981 | Schal |
| 4,282,099 A | 8/1981 | Jones |
| 4,299,784 A | 11/1981 | Hense |
| 4,309,592 A | 1/1982 | Le Boeuf |
| 4,322,054 A | 3/1982 | Campbell |
| 4,362,156 A | 12/1982 | Feller, Jr. et al. |
| 4,369,781 A | 1/1983 | Gilson et al. |
| 4,398,908 A | 8/1983 | Siposs |
| 4,411,783 A | 10/1983 | Dickens et al. |
| 4,439,188 A | 3/1984 | Dennehey et al. |
| 4,441,357 A | 4/1984 | Kahn et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,490,254 A | 12/1984 | Gordon et al. |
| 4,501,405 A | 2/1985 | Usry |
| 4,574,876 A | 3/1986 | Aid |
| 4,585,442 A | 4/1986 | Mannes |
| 4,623,334 A | 11/1986 | Riddell |
| 4,623,450 A | 11/1986 | Vantard et al. |
| 4,664,891 A | 5/1987 | Cosentino et al. |
| 4,680,445 A | 7/1987 | Ogawa |
| 4,695,385 A | 9/1987 | Boag |
| 4,718,022 A | 1/1988 | Cochran |
| 4,731,072 A | 3/1988 | Aid |
| 4,767,526 A | 8/1988 | Vantard |
| 4,770,769 A | 9/1988 | Schael |
| 4,778,451 A | 10/1988 | Kamen |
| 4,784,495 A | 11/1988 | Jonsson et al. |
| 4,808,161 A | 2/1989 | Kamen |
| 4,822,343 A | 4/1989 | Beiser |
| 4,826,482 A | 5/1989 | Kamen |
| 4,828,543 A | 5/1989 | Weiss et al. |
| 4,833,329 A | 5/1989 | Quint et al. |
| 4,906,816 A | 3/1990 | van Leerdam |
| 4,927,411 A | 5/1990 | Pastrone et al. |
| 4,950,235 A | 8/1990 | Slate et al. |
| 4,971,700 A | 11/1990 | Tsuji et al. |
| 4,976,162 A | 12/1990 | Kamen |
| 4,997,570 A | 3/1991 | Polaschegg |
| 5,024,756 A | 6/1991 | Sternby |
| 5,033,513 A | 7/1991 | Bartholomew |
| 5,061,241 A | 10/1991 | Stephens, Jr. et al. |
| 5,062,774 A | 11/1991 | Kramer et al. |
| 5,074,838 A | 12/1991 | Kroyer |
| 5,088,515 A | 2/1992 | Kamen |
| 5,088,901 A | 2/1992 | Brauer |
| 5,100,554 A | 3/1992 | Polaschegg |
| 5,105,981 A | 4/1992 | Gehman |
| 5,110,447 A | 5/1992 | MacWilliams et al. |
| 5,110,477 A | 5/1992 | Howard et al. |
| 5,116,316 A | 5/1992 | Sertic et al. |
| 5,125,069 A | 6/1992 | O'Boyle |
| 5,160,325 A | 11/1992 | Nichols et al. |
| 5,178,182 A | 1/1993 | Kamen |
| 5,245,693 A | 9/1993 | Ford et al. |
| 5,247,434 A | 9/1993 | Peterson et al. |
| 5,267,956 A | 12/1993 | Beuchat |
| 5,278,072 A | 1/1994 | Wall et al. |
| 5,300,044 A | 4/1994 | Classey et al. |
| 5,306,242 A | 4/1994 | Joyce et al. |
| 5,324,422 A | 6/1994 | Colleran et al. |
| 5,326,476 A | 7/1994 | Grogan et al. |
| D350,823 S | 9/1994 | Lanigan |
| D350,850 S | 9/1994 | Angelini |
| 5,349,896 A | 9/1994 | Delaney, III et al. |
| 5,350,357 A | 9/1994 | Kamen et al. |
| 5,351,686 A | 10/1994 | Steuer et al. |
| 5,362,383 A | 11/1994 | Zimmerman et al. |
| 5,378,126 A | 1/1995 | Abrahamson et al. |
| 5,381,510 A | 1/1995 | Ford et al. |
| 5,385,540 A | 1/1995 | Abbott et al. |
| 5,395,316 A | 3/1995 | Martin |
| 5,410,255 A | 4/1995 | Bailey |
| 5,411,472 A | 5/1995 | Steg, Jr. et al. |
| 5,413,566 A | 5/1995 | Sevrain et al. |
| 5,420,962 A | 5/1995 | Bakke |
| 5,421,823 A | 6/1995 | Kamen et al. |
| 5,423,738 A | 6/1995 | Robinson et al. |
| 5,429,485 A | 7/1995 | Dodge |
| 5,431,626 A | 7/1995 | Bryant et al. |
| 5,438,510 A | 8/1995 | Bryant et al. |
| 5,441,231 A | 8/1995 | Payne et al. |
| 5,441,343 A | 8/1995 | Pylkki et al. |
| 5,441,636 A | 8/1995 | Chevallet et al. |
| 5,472,614 A | 12/1995 | Rossi |
| 5,474,683 A | 12/1995 | Bryant et al. |
| 5,476,368 A | 12/1995 | Rabenau et al. |
| 5,476,444 A | 12/1995 | Keeling et al. |
| 5,482,440 A | 1/1996 | Dennehey et al. |
| 5,486,286 A | 1/1996 | Peterson et al. |
| 5,487,827 A | 1/1996 | Peterson et al. |
| 5,496,273 A | 3/1996 | Pastrone et al. |
| 5,516,429 A | 5/1996 | Snodgrass et al. |
| 5,527,507 A | 6/1996 | Childers et al. |
| 5,541,344 A | 7/1996 | Becker et al. |
| 5,542,919 A | 8/1996 | Simon et al. |
| 5,558,255 A | 9/1996 | Sancoff et al. |
| 5,568,362 A | 10/1996 | Hansson |
| 5,575,310 A | 11/1996 | Kamen et al. |
| 5,578,012 A | 11/1996 | Kamen et al. |
| 5,580,460 A | 12/1996 | Polaschegg |
| 5,586,438 A | 12/1996 | Fahy |
| 5,591,344 A | 1/1997 | Kenley et al. |
| 5,591,389 A | 1/1997 | Esrock |
| 5,593,290 A | 1/1997 | Greisch et al. |
| 5,609,770 A | 3/1997 | Zimmerman et al. |
| 5,616,248 A | 4/1997 | Schal |
| 5,628,908 A | 5/1997 | Kamen et al. |
| 5,632,894 A | 5/1997 | White et al. |
| 5,634,896 A | 6/1997 | Bryant et al. |
| 5,645,531 A | 7/1997 | Thompson et al. |
| 5,651,765 A | 7/1997 | Haworth et al. |
| 5,651,893 A | 7/1997 | Kenley et al. |
| 5,651,898 A | 7/1997 | Imura |
| 5,676,644 A | 10/1997 | Toavs et al. |
| 5,690,831 A | 11/1997 | Kenley et al. |
| 5,692,729 A | 12/1997 | Harhen |
| 5,702,597 A | 12/1997 | Chevallet et al. |
| 5,729,653 A | 3/1998 | Magliochetti et al. |
| 5,730,720 A | 3/1998 | Sites et al. |
| 5,744,027 A | 4/1998 | Connell et al. |
| 5,755,275 A | 5/1998 | Rose et al. |

(56) References Cited

U.S. PATENT DOCUMENTS

| | | |
|---|---|---|
| 5,755,683 A | 5/1998 | Houle et al. |
| 5,776,091 A | 7/1998 | Brugger et al. |
| 5,782,508 A | 7/1998 | Bartholomew |
| 5,797,897 A | 8/1998 | Jepson et al. |
| 5,875,282 A | 2/1999 | Jordan et al. |
| 5,879,316 A | 3/1999 | Safar et al. |
| 5,882,047 A | 3/1999 | Ostrander et al. |
| 5,899,873 A | 5/1999 | Jones et al. |
| 5,902,476 A | 5/1999 | Twardowski |
| 5,906,978 A | 5/1999 | Ash |
| 5,925,011 A | 7/1999 | Faict et al. |
| 5,931,648 A | 8/1999 | Del Canizo |
| 5,932,103 A | 8/1999 | Kenley et al. |
| 5,932,110 A | 8/1999 | Shah et al. |
| 5,938,634 A | 8/1999 | Packard |
| 5,947,931 A | 9/1999 | Bierman |
| 5,989,423 A | 11/1999 | Kamen et al. |
| 6,039,877 A | 3/2000 | Chevallet et al. |
| 6,041,801 A | 3/2000 | Gray et al. |
| 6,042,784 A | 3/2000 | Wamsiedler et al. |
| 6,044,868 A | 4/2000 | Gretz et al. |
| 6,047,108 A | 4/2000 | Sword et al. |
| 6,062,068 A | 5/2000 | Bowling et al. |
| 6,070,761 A | 6/2000 | Bloom et al. |
| 6,101,406 A | 8/2000 | Hacker et al. |
| 6,109,881 A | 8/2000 | Snodgrass et al. |
| 6,136,201 A | 10/2000 | Shah et al. |
| 6,139,819 A | 10/2000 | Unger et al. |
| 6,142,164 A | 11/2000 | Wier et al. |
| 6,142,446 A | 11/2000 | Leinsing |
| 6,146,354 A | 11/2000 | Beil |
| 6,146,523 A | 11/2000 | Kenley et al. |
| 6,146,536 A | 11/2000 | Twardowski |
| 6,153,102 A | 11/2000 | Kenley et al. |
| 6,159,192 A | 12/2000 | Fowles et al. |
| 6,171,261 B1 | 1/2001 | Niermann et al. |
| 6,176,904 B1 | 1/2001 | Gupta |
| 6,210,361 B1 | 4/2001 | Kamen et al. |
| 6,213,996 B1 | 4/2001 | Jepson et al. |
| 6,223,130 B1 | 4/2001 | Gray et al. |
| 6,234,997 B1 | 5/2001 | Kamen et al. |
| RE37,324 E | 8/2001 | Esrock |
| 6,274,303 B1 | 8/2001 | Wowk et al. |
| 6,277,272 B1 | 8/2001 | Nikaido et al. |
| 6,277,277 B1 | 8/2001 | Jacobi et al. |
| 6,284,131 B1 | 9/2001 | Hogard et al. |
| 6,302,653 B1 | 10/2001 | Bryant et al. |
| 6,321,597 B1 | 11/2001 | Demers et al. |
| 6,327,895 B1 | 12/2001 | Jeppsson et al. |
| 6,331,778 B1 | 12/2001 | Daily et al. |
| 6,336,003 B1 | 1/2002 | Mitsunaga et al. |
| 6,336,911 B1 | 1/2002 | Westerbeck |
| 6,347,633 B1 | 2/2002 | Groth et al. |
| 6,382,923 B1 | 5/2002 | Gray |
| 6,406,426 B1 | 6/2002 | Reuss et al. |
| 6,406,452 B1 | 6/2002 | Westerbeck |
| 6,413,233 B1 | 7/2002 | Sites et al. |
| 6,415,797 B1 | 7/2002 | Groth et al. |
| 6,416,293 B1 | 7/2002 | Bouchard et al. |
| 6,423,053 B1 | 7/2002 | Lee |
| 6,464,666 B1 | 10/2002 | Augustine et al. |
| 6,480,257 B2 | 11/2002 | Cassidy et al. |
| 6,485,263 B1 | 11/2002 | Bryant et al. |
| 6,491,656 B1 | 12/2002 | Morris |
| 6,497,676 B1 | 12/2002 | Childers et al. |
| 6,517,510 B1 | 2/2003 | Stewart et al. |
| 6,520,747 B2 | 2/2003 | Gray et al. |
| 6,527,758 B2 | 3/2003 | Ko |
| 6,529,775 B2 | 3/2003 | Whitebook et al. |
| 6,535,689 B2 | 3/2003 | Augustine et al. |
| 6,537,445 B2 | 3/2003 | Muller |
| 6,539,172 B2 | 3/2003 | Akahane |
| 6,543,814 B2 | 4/2003 | Bartholomew |
| 6,579,253 B1 | 6/2003 | Burbank et al. |
| 6,579,496 B1 | 6/2003 | Fausset et al. |
| RE38,203 E | 7/2003 | Kelly |
| 6,595,944 B2 | 7/2003 | Balschat et al. |
| 6,595,948 B2 | 7/2003 | Suzuki et al. |
| 6,604,908 B1 | 8/2003 | Bryant et al. |
| 6,608,968 B2 | 8/2003 | Bakke |
| 6,620,119 B1 | 9/2003 | Utterberg et al. |
| 6,649,063 B1 | 11/2003 | Brugger et al. |
| 6,660,974 B2 | 12/2003 | Faries, Jr. et al. |
| 6,663,353 B2 | 12/2003 | Lipscomb et al. |
| 6,663,359 B2 | 12/2003 | Gray |
| 6,673,314 B1 | 1/2004 | Burbank et al. |
| 6,709,417 B1 | 3/2004 | Houle et al. |
| 6,722,865 B2 | 4/2004 | Domroese |
| 6,723,062 B1 | 4/2004 | Westberg et al. |
| 6,726,656 B2 | 4/2004 | Kamen et al. |
| 6,743,201 B1 | 6/2004 | Donig et al. |
| 6,749,403 B2 | 6/2004 | Bryant et al. |
| 6,752,172 B2 | 6/2004 | Lauer |
| 6,758,975 B2 | 7/2004 | Peabody et al. |
| 6,768,085 B2 | 7/2004 | Faries et al. |
| 6,775,473 B2 | 8/2004 | Augustine et al. |
| 6,788,885 B2 | 9/2004 | Mitsunaga et al. |
| 6,808,369 B2 | 10/2004 | Gray et al. |
| 6,814,547 B2 | 11/2004 | Childers et al. |
| 6,814,718 B2 | 11/2004 | McGuckin, Jr. et al. |
| 6,818,179 B1 | 11/2004 | Edgson et al. |
| 6,826,948 B1 | 12/2004 | Bhatti et al. |
| 6,858,019 B2 | 2/2005 | McGuckin, Jr. et al. |
| 6,860,866 B1 | 3/2005 | Graf et al. |
| 6,868,309 B1 | 3/2005 | Begelman |
| 6,877,713 B1 | 4/2005 | Gray et al. |
| 6,905,314 B2 | 6/2005 | Danby |
| 6,905,479 B1 | 6/2005 | Bouchard et al. |
| 6,929,751 B2 | 8/2005 | Bowman, Jr. et al. |
| 6,939,471 B2 | 9/2005 | Gross et al. |
| 6,949,079 B1 | 9/2005 | Westberg et al. |
| 6,953,323 B2 | 10/2005 | Childers et al. |
| 7,029,245 B2 | 4/2006 | Maianti et al. |
| 7,083,719 B2 | 8/2006 | Bowman, Jr. et al. |
| 7,122,210 B2 | 10/2006 | Elisabettini et al. |
| 7,124,996 B2 | 10/2006 | Clarke et al. |
| 7,147,613 B2 | 12/2006 | Burbank et al. |
| 7,153,286 B2 | 12/2006 | Busby et al. |
| 7,168,334 B1 | 1/2007 | Drott |
| 7,169,303 B2 | 1/2007 | Sullivan et al. |
| 7,175,397 B2 | 2/2007 | Claude et al. |
| 7,175,606 B2 | 2/2007 | Bowman et al. |
| 7,214,210 B2 | 5/2007 | Kamen et al. |
| 7,238,164 B2 | 7/2007 | Childers et al. |
| 7,273,465 B2 | 9/2007 | Ash |
| 7,300,413 B2 | 11/2007 | Burbank et al. |
| 7,303,540 B2 | 12/2007 | O'Mahony et al. |
| 7,318,292 B2 | 1/2008 | Helbling et al. |
| 7,318,892 B2 | 1/2008 | Connell et al. |
| 7,410,294 B2 | 8/2008 | Shiraki et al. |
| 7,461,968 B2 | 12/2008 | Demers et al. |
| 7,465,285 B2 | 12/2008 | Hutchinson et al. |
| 7,476,209 B2 | 1/2009 | Gara et al. |
| 7,488,448 B2 | 2/2009 | Wieting et al. |
| 7,500,962 B2 | 3/2009 | Childers et al. |
| 7,544,179 B2 | 6/2009 | Distler et al. |
| 7,559,524 B2 | 7/2009 | Gray et al. |
| 7,563,248 B2 | 7/2009 | Smisson, III et al. |
| 7,601,636 B2 | 10/2009 | Dumas et al. |
| 7,632,078 B2 | 12/2009 | Demers et al. |
| 7,632,080 B2 | 12/2009 | Tracey et al. |
| 7,648,627 B2 | 1/2010 | Beden et al. |
| 7,662,286 B2 | 2/2010 | Childers et al. |
| 7,717,682 B2 | 5/2010 | Orr |
| 7,727,176 B2 | 6/2010 | Tonelli et al. |
| 7,744,553 B2 | 6/2010 | Kelly et al. |
| 7,776,006 B2 | 8/2010 | Childers et al. |
| 7,776,301 B2 | 8/2010 | Comrie |
| 7,789,849 B2 | 9/2010 | Busby et al. |
| 7,794,141 B2 | 9/2010 | Perry et al. |
| 7,798,997 B2 | 9/2010 | Kamen et al. |
| 7,815,595 B2 | 10/2010 | Busby et al. |
| 7,867,214 B2 | 1/2011 | Childers et al. |
| 7,892,197 B2 | 2/2011 | Folden et al. |

(56) References Cited

U.S. PATENT DOCUMENTS

| | | |
|---|---|---|
| 7,896,830 B2 | 3/2011 | Gura et al. |
| 7,935,074 B2 | 5/2011 | Plahey et al. |
| 7,935,250 B2 | 5/2011 | Castellano et al. |
| 7,967,022 B2 | 6/2011 | Grant et al. |
| 8,002,726 B2 | 8/2011 | Karoor et al. |
| 8,029,454 B2 | 10/2011 | Kelly et al. |
| 8,042,563 B2 | 10/2011 | Grant et al. |
| 8,066,671 B2 | 11/2011 | Busby et al. |
| 8,075,526 B2 | 12/2011 | Busby et al. |
| 8,105,265 B2 | 1/2012 | Demers et al. |
| 8,137,553 B2 | 3/2012 | Fulkerson et al. |
| 8,246,826 B2 | 8/2012 | Wilt et al. |
| 8,266,967 B2 | 9/2012 | Kitani et al. |
| 8,273,049 B2 | 9/2012 | Demers et al. |
| 8,292,594 B2 | 10/2012 | Tracey et al. |
| 8,298,152 B2 | 10/2012 | Konig et al. |
| 8,317,492 B2 | 11/2012 | Demers et al. |
| 8,357,298 B2 | 1/2013 | Demers et al. |
| 8,366,316 B2 | 2/2013 | Kamen et al. |
| 8,366,655 B2 | 2/2013 | Kamen et al. |
| 8,393,690 B2 | 3/2013 | Grant et al. |
| 8,409,441 B2 | 4/2013 | Wilt |
| 8,425,471 B2 | 4/2013 | Grant et al. |
| 8,444,587 B2 | 5/2013 | Kelly et al. |
| 8,459,292 B2 | 6/2013 | Wilt et al. |
| 8,491,184 B2 | 7/2013 | Kamen et al. |
| 8,499,780 B2 | 8/2013 | Wilt et al. |
| 8,512,553 B2 | 8/2013 | Cicchello et al. |
| 8,535,525 B2 | 9/2013 | Heyes et al. |
| 8,545,698 B2 | 10/2013 | Wilt et al. |
| 8,562,834 B2 | 10/2013 | Kamen et al. |
| 8,597,505 B2 | 12/2013 | Fulkerson et al. |
| 8,673,139 B2 | 3/2014 | Hedmann et al. |
| 8,721,879 B2 | 5/2014 | van der Merwe et al. |
| 8,721,884 B2 | 5/2014 | Wilt et al. |
| 8,771,508 B2 | 7/2014 | Grant et al. |
| 8,858,787 B2 | 10/2014 | Muller et al. |
| 8,863,772 B2 | 10/2014 | Dale et al. |
| 8,870,549 B2 | 10/2014 | Tracey et al. |
| 8,870,811 B2 | 10/2014 | Gavin et al. |
| 8,888,470 B2 | 11/2014 | Demers et al. |
| 8,906,240 B2 | 12/2014 | Crnkovich et al. |
| 8,926,294 B2 | 1/2015 | Demers et al. |
| 8,968,232 B2 | 3/2015 | Kamen et al. |
| 8,985,133 B2 | 3/2015 | Grant et al. |
| 8,992,075 B2 | 3/2015 | Kamen et al. |
| 8,992,189 B2 | 3/2015 | Wilt et al. |
| 9,028,691 B2 | 5/2015 | Grant et al. |
| 9,115,708 B2 | 8/2015 | van der Merwe et al. |
| 9,248,225 B2 | 2/2016 | Demers et al. |
| 9,272,082 B2 | 3/2016 | Demers et al. |
| 9,302,037 B2 | 4/2016 | Wilt et al. |
| 9,364,655 B2 | 6/2016 | Grant et al. |
| 2002/0056672 A1 | 5/2002 | Lyle et al. |
| 2002/0092103 A1 | 7/2002 | Bruno et al. |
| 2002/0103453 A1 | 8/2002 | Burbank et al. |
| 2002/0150476 A1 | 10/2002 | Lucke et al. |
| 2002/0179505 A1 | 12/2002 | Rovatti et al. |
| 2002/0179595 A1 | 12/2002 | Nagele |
| 2002/0182090 A1 | 12/2002 | Gray |
| 2003/0100858 A1 | 5/2003 | Utterberg et al. |
| 2003/0114795 A1 | 6/2003 | Faries et al. |
| 2003/0194332 A1 | 10/2003 | Jahn et al. |
| 2003/0195453 A1 | 10/2003 | Han et al. |
| 2003/0195454 A1 | 10/2003 | Wariar et al. |
| 2003/0220599 A1 | 11/2003 | Lundtveit et al. |
| 2003/0220607 A1 | 11/2003 | Busby et al. |
| 2003/0229302 A1 | 12/2003 | Robinson et al. |
| 2003/0230191 A1 | 12/2003 | Ohrle et al. |
| 2004/0001766 A1 | 1/2004 | Maianti et al. |
| 2004/0009096 A1 | 1/2004 | Wellman |
| 2004/0019313 A1 | 1/2004 | Childers et al. |
| 2004/0091374 A1 | 5/2004 | Gray |
| 2004/0101026 A1 | 5/2004 | Nitta et al. |
| 2004/0136843 A1 | 7/2004 | Jahn et al. |
| 2004/0138607 A1 | 7/2004 | Burbank et al. |
| 2004/0211718 A1 | 10/2004 | Deguchi et al. |
| 2004/0245161 A1 | 12/2004 | Treu et al. |
| 2004/0262917 A1 | 12/2004 | Sunohara et al. |
| 2005/0020958 A1 | 1/2005 | Paolini et al. |
| 2005/0045540 A1 | 3/2005 | Connell et al. |
| 2005/0069425 A1 | 3/2005 | Gray et al. |
| 2005/0069427 A1 | 3/2005 | Roemuss et al. |
| 2005/0095141 A1 | 5/2005 | Lanigan et al. |
| 2005/0095154 A1 | 5/2005 | Tracey et al. |
| 2005/0126998 A1 | 6/2005 | Childers |
| 2005/0130332 A1 | 6/2005 | Ishii et al. |
| 2005/0131332 A1 | 6/2005 | Kelly et al. |
| 2005/0209563 A1 | 9/2005 | Hopping et al. |
| 2005/0230292 A1 | 10/2005 | Beden et al. |
| 2005/0234385 A1 | 10/2005 | Vandlik et al. |
| 2005/0242034 A1 | 11/2005 | Connell et al. |
| 2005/0274658 A1 | 12/2005 | Rosenbaum et al. |
| 2006/0002823 A1 | 1/2006 | Feldstein |
| 2006/0093531 A1 | 5/2006 | Tremoulet et al. |
| 2006/0184084 A1 | 8/2006 | Ware et al. |
| 2006/0195064 A1 | 8/2006 | Plahey et al. |
| 2006/0241550 A1 | 10/2006 | Kamen et al. |
| 2007/0060786 A1 | 3/2007 | Gura et al. |
| 2007/0077156 A1 | 4/2007 | Orr |
| 2007/0112297 A1 | 5/2007 | Plahey et al. |
| 2007/0135758 A1 | 6/2007 | Childers et al. |
| 2007/0166181 A1 | 7/2007 | Nilson |
| 2007/0253463 A1 | 11/2007 | Perry et al. |
| 2007/0255527 A1 | 11/2007 | Schick et al. |
| 2007/0278155 A1 | 12/2007 | Lo et al. |
| 2008/0015493 A1 | 1/2008 | Childers et al. |
| 2008/0015515 A1 | 1/2008 | Hopkins et al. |
| 2008/0021377 A1 | 1/2008 | Kienman et al. |
| 2008/0033346 A1 | 2/2008 | Childers et al. |
| 2008/0058697 A1 | 3/2008 | Kamen et al. |
| 2008/0058712 A1 | 3/2008 | Plahey |
| 2008/0077068 A1 | 3/2008 | Orr |
| 2008/0097283 A1 | 4/2008 | Plahey |
| 2008/0105600 A1 | 5/2008 | Connell et al. |
| 2008/0125693 A1 | 5/2008 | Gavin et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0202591 A1 | 8/2008 | Grant et al. |
| 2008/0204086 A1 | 8/2008 | Park et al. |
| 2008/0205481 A1 | 8/2008 | Faries, Jr. et al. |
| 2008/0208103 A1 | 8/2008 | Demers et al. |
| 2008/0208111 A1 | 8/2008 | Kamen et al. |
| 2008/0215898 A1 | 9/2008 | Lu et al. |
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2008/0287854 A1 | 11/2008 | Sun |
| 2009/0004033 A1 | 1/2009 | Demers et al. |
| 2009/0007642 A1 | 1/2009 | Busby et al. |
| 2009/0008331 A1 | 1/2009 | Wilt et al. |
| 2009/0009290 A1 | 1/2009 | Kneip et al. |
| 2009/0012447 A1 | 1/2009 | Huitt et al. |
| 2009/0012448 A1 | 1/2009 | Childers et al. |
| 2009/0012449 A1 | 1/2009 | Lee et al. |
| 2009/0012450 A1 | 1/2009 | Shah et al. |
| 2009/0012452 A1 | 1/2009 | Slepicka et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012460 A1 | 1/2009 | Steck et al. |
| 2009/0012461 A1 | 1/2009 | Childers et al. |
| 2009/0024070 A1 | 1/2009 | Gelfand et al. |
| 2009/0043239 A1 | 2/2009 | Gagel et al. |
| 2009/0076433 A1 | 3/2009 | Folden et al. |
| 2009/0076434 A1 | 3/2009 | Mischelevich et al. |
| 2009/0088675 A1 | 4/2009 | Kelly et al. |
| 2009/0088683 A1 | 4/2009 | Roger et al. |

(56) References Cited

U.S. PATENT DOCUMENTS

| | | |
|---|---|---|
| 2009/0095679 A1 | 4/2009 | Demers et al. |
| 2009/0101549 A1 | 4/2009 | Kamen et al. |
| 2009/0101550 A1 | 4/2009 | Muller et al. |
| 2009/0101566 A1 | 4/2009 | Crnkovich et al. |
| 2009/0105621 A1 | 4/2009 | Boyd et al. |
| 2009/0105629 A1 | 4/2009 | Grant et al. |
| 2009/0107335 A1 | 4/2009 | Wilt et al. |
| 2009/0107902 A1 | 4/2009 | Childers et al. |
| 2009/0112151 A1 | 4/2009 | Chapman et al. |
| 2009/0113335 A1 | 4/2009 | Sandoe et al. |
| 2009/0114582 A1 | 5/2009 | Grant et al. |
| 2009/0154524 A1 | 6/2009 | Girelli |
| 2009/0173682 A1 | 7/2009 | Robinson et al. |
| 2009/0182263 A1 | 7/2009 | Burbank et al. |
| 2009/0192367 A1 | 7/2009 | Braig et al. |
| 2009/0202367 A1 | 8/2009 | Gray et al. |
| 2010/0051529 A1 | 3/2010 | Grant et al. |
| 2010/0051551 A1 | 3/2010 | Grant et al. |
| 2010/0056975 A1 | 3/2010 | Dale et al. |
| 2010/0057016 A1 | 3/2010 | Dale et al. |
| 2010/0087777 A1 | 4/2010 | Hopping et al. |
| 2010/0133153 A1 | 6/2010 | Beden et al. |
| 2010/0137782 A1 | 6/2010 | Jansson et al. |
| 2010/0185134 A1 | 7/2010 | Houwen et al. |
| 2010/0187176 A1 | 7/2010 | Del Canizo Lopez |
| 2010/0192686 A1 | 8/2010 | Kamen et al. |
| 2010/0296953 A1 | 11/2010 | Gray |
| 2010/0327849 A1 | 12/2010 | Kamen et al. |
| 2011/0005992 A1 | 1/2011 | Kelly et al. |
| 2011/0009797 A1 | 1/2011 | Kelly et al. |
| 2011/0092875 A1 | 4/2011 | Beck |
| 2011/0105877 A1 | 5/2011 | Wilt et al. |
| 2011/0144569 A1 | 6/2011 | Britton et al. |
| 2011/0218600 A1 | 9/2011 | Kamen et al. |
| 2011/0299358 A1 | 12/2011 | Wilt et al. |
| 2011/0303588 A1 | 12/2011 | Kelly et al. |
| 2011/0303598 A1 | 12/2011 | Lo et al. |
| 2012/0035533 A1 | 2/2012 | Britton et al. |
| 2012/0071816 A1 | 3/2012 | Busby et al. |
| 2012/0106289 A1 | 5/2012 | Wilt et al. |
| 2012/0207627 A1 | 8/2012 | Demers et al. |
| 2013/0010825 A1 | 1/2013 | Kamen et al. |
| 2013/0020237 A1 | 1/2013 | Wilt et al. |
| 2013/0022483 A1 | 1/2013 | Wilt et al. |
| 2013/0032536 A1 | 2/2013 | Wilt et al. |
| 2013/0037480 A1 | 2/2013 | Wilt et al. |
| 2013/0037485 A1 | 2/2013 | Wilt et al. |
| 2013/0074959 A1 | 3/2013 | Demers et al. |
| 2013/0115105 A1 | 5/2013 | Tracey et al. |
| 2013/0126413 A1 | 5/2013 | Van der Merwe et al. |
| 2013/0177457 A1 | 7/2013 | Demers et al. |
| 2013/0193041 A1 | 8/2013 | Rohde |
| 2013/0284648 A1 | 10/2013 | Grant et al. |
| 2013/0304020 A1 | 11/2013 | Wilt et al. |
| 2013/0317454 A1 | 11/2013 | Grant et al. |
| 2014/0102299 A1 | 4/2014 | Wilt et al. |
| 2014/0102958 A1 | 4/2014 | Kamen et al. |
| 2014/0102970 A1 | 4/2014 | Wilt et al. |
| 2014/0112828 A1 | 4/2014 | Grant et al. |
| 2014/0153356 A1 | 6/2014 | Giant et al. |
| 2014/0199193 A1 | 7/2014 | Wilt et al. |
| 2014/0299544 A1 | 10/2014 | Wilt et al. |
| 2014/0309611 A1 | 10/2014 | Wilt et al. |
| 2014/0319041 A1 | 10/2014 | Wilt et al. |
| 2014/0322053 A1 | 10/2014 | van der Merwe et al. |
| 2015/0042366 A1 | 2/2015 | Wilt et al. |
| 2015/0050166 A1 | 2/2015 | Tracey et al. |
| 2015/0125319 A1 | 5/2015 | Demers et al. |
| 2015/0196698 A1 | 7/2015 | Grant et al. |
| 2015/0196699 A9 | 7/2015 | Wilt et al. |
| 2015/0224242 A1 | 8/2015 | Grant et al. |
| 2015/0265760 A1 | 9/2015 | Wilt et al. |
| 2016/0030657 A1 | 2/2016 | Kelly et al. |
| 2016/0030658 A1 | 2/2016 | Van der Merwe et al. |
| 2016/0058933 A1 | 3/2016 | Ballantyne et al. |
| 2016/0082173 A1 | 3/2016 | Coll et al. |
| 2016/0175505 A1 | 6/2016 | Demers et al. |
| 2016/0175506 A1 | 6/2016 | Wilt et al. |

FOREIGN PATENT DOCUMENTS

| | | |
|---|---|---|
| DE | 3 328 744 A1 | 2/1985 |
| EP | 0 687 474 A1 | 12/1995 |
| EP | 0 815 882 A2 | 1/1998 |
| EP | 0829266 A2 | 3/1998 |
| EP | 0 992 255 A2 | 4/2000 |
| EP | 2 131 893 | 9/2008 |
| EP | 2 319 551 A2 | 5/2011 |
| JP | S60-077782 U | 5/1985 |
| JP | 3103982 | 4/1991 |
| JP | H09-099060 | 4/1997 |
| JP | H11-210633 A | 8/1999 |
| JP | 2001-513675 | 9/2001 |
| JP | 2002-539896 | 11/2002 |
| JP | 2003-509131 | 3/2003 |
| JP | 3422023 | 6/2003 |
| JP | 2005-526573 | 9/2005 |
| JP | 2006-512138 | 4/2006 |
| JP | 2006-204343 A | 8/2006 |
| JP | 2006-218130 A | 8/2006 |
| JP | 2008-006292 A | 1/2008 |
| JP | 2008-136673 A | 6/2008 |
| JP | 2008-539848 | 11/2008 |
| KR | 10-2002-0008145 | 1/2002 |
| KR | 10-2002-0010601 | 2/2002 |
| WO | WO 93/11829 | 6/1993 |
| WO | WO 94/11093 A1 | 5/1994 |
| WO | WO 94/20158 A1 | 9/1994 |
| WO | WO 96/40320 A1 | 12/1996 |
| WO | WO 98/37801 A1 | 9/1998 |
| WO | WO 98/39058 A1 | 9/1998 |
| WO | WO 99/10028 A1 | 3/1999 |
| WO | WO 00/57935 | 10/2000 |
| WO | WO 01/19430 A1 | 3/2001 |
| WO | WO 01/37895 A2 | 5/2001 |
| WO | WO 02/03879 A1 | 1/2002 |
| WO | WO 02/30267 A2 | 4/2002 |
| WO | WO 03/099353 A2 | 12/2003 |
| WO | WO 2004/041081 A1 | 5/2004 |
| WO | WO 2004/060449 A2 | 7/2004 |
| WO | WO 2005/044339 A1 | 5/2005 |
| WO | WO 2005/044435 A2 | 5/2005 |
| WO | WO 2005/089832 A2 | 9/2005 |
| WO | WO 2006/088419 A2 | 8/2006 |
| WO | WO 2006/120415 A1 | 11/2006 |
| WO | WO 2007/019519 A2 | 2/2007 |
| WO | WO 2007/120812 A2 | 10/2007 |
| WO | WO 2007/126360 A1 | 11/2007 |
| WO | WO 2007/149637 A2 | 12/2007 |
| WO | WO 2008/028653 A2 | 3/2008 |
| WO | WO 2008/053259 A1 | 5/2008 |
| WO | WO 2008/106191 A2 | 9/2008 |
| WO | WO 2008/106440 A1 | 9/2008 |
| WO | WO 2008/106452 A1 | 9/2008 |
| WO | WO 2008/106538 A2 | 9/2008 |
| WO | WO 2008/118600 A1 | 10/2008 |
| WO | WO 2009/051669 A1 | 4/2009 |
| WO | WO 2009/094179 A2 | 7/2009 |
| WO | WO 2009/094183 A1 | 7/2009 |
| WO | WO 2009/094184 A1 | 7/2009 |
| WO | WO 2010/027435 A1 | 3/2010 |
| WO | WO 2010/027437 A2 | 3/2010 |
| WO | WO 2010/042666 | 4/2010 |
| WO | WO 2011/053810 A2 | 5/2011 |
| WO | WO 2012/006425 A2 | 1/2012 |
| WO | WO 2013/067359 A2 | 5/2013 |

OTHER PUBLICATIONS

Response to Examination Report dated May 16, 2012 for EP Application No. 08726213.5 filed Sep. 24, 2009, which Response is dated Nov. 21, 2012, and claims as pending for EP Application No. 08726213.5 as of Nov. 21, 2012.

(56) References Cited

OTHER PUBLICATIONS

Office Action for JP Application No. 2009-551724 filed Feb. 27, 2008, which Office Action is dated Aug. 27, 2009, and claims as pending for JP Application No. 2009-551724 as of Nov. 28, 2012.
Office Action for U.S. Appl. No. 12/072,908, filed Feb. 27, 2008, published as US 2009-0008331 on Jan. 8, 2009 which Office Action is dated Oct. 15, 2010, and claims as pending for U.S. Appl. No. 12/072,908 as of Oct. 15, 2010.
Office Action for U.S. Appl. No. 12/072,908, filed Feb. 27, 2008, published as US 2009-0008331 on Jan. 8, 2009 which Office Action is dated Jul. 15, 2011, and claims as pending for U.S. Appl. No. 12/072,908 as of Juy 15, 2011.
Written Opinion for Application No. PCT/US2008/002636 mailed Jul. 2, 2008.
International Preliminary Report on Patentability for Application No. PCT/US2008/002636 mailed Sep. 11, 2009.
Office Action for U.S. Appl. No. 11/871,712, filed Oct. 12, 2007, published as US 2009/0004033 on Jan. 1, 2009, which Office Action is dated Feb. 4, 2010, and claims as pending for U.S. Appl. No. 11/871,712 as of Feb. 4, 2010.
Office Action for U.S. Appl. No. 11/871,712, filed Oct. 12, 2007, published as US 2009-0004033 on Jan. 1, 2009, which Office Action is dated Oct. 15, 2010, and claims as pending for U.S. Appl. No. 11/871,712 as of Oct. 15, 2010.
Office Action for U.S. Appl. No. 11/871,712, filed Oct. 12, 2007, published as US 2009-0004033 on Jan. 1, 2009, which Office Action is dated Feb. 7, 2011, and claims as pending for U.S. Appl. No. 11/871,712 as of Feb. 7, 2011.
International Search Report and Written Opinion for Application No. PCT/US2008/055000 mailed Aug. 1, 2008.
International Preliminary Report on Patentability for Application No. PCT/US2008/055000 mailed Sep. 11, 2009.
Office Action for U.S. Appl. No. 11/871,787, filed Oct. 12, 2007, published as US 2008-0253911 on Oct. 16, 2008, which Office Action is dated Apr. 14, 2011, and claims as pending for U.S. Appl. No. 11/871,787 as of Apr. 14, 2011.
Office Action for U.S. Appl. No. 11/871,793, filed Oct. 12, 2007, published as US 2008-0253912 on Oct. 16, 2008, which Office Action is dated Apr. 28, 2011, and claims as pending for U.S. Appl. No. 11/871,793 as of Apr. 28, 2011.
Office Action for U.S. Appl. No. 13/352,250, filed Jan. 17, 2012, published as US 2012-0207627 on Aug. 16, 2012, which Office Action is dated Feb. 27, 2015, and claims as pending for U.S. Appl. No. 13/352,250 as of Feb. 27, 2015.
Office Action for AU Application No. 2013204505 filed Apr. 12, 2013, which Office Action is dated Jun. 12, 2014 and claims as pending for AU Application No. 2013204505 as of Jun. 12, 2014.
Extended European Search Report for EP Application No. 14155798.3 filed Feb. 27, 2008, which Search Report is dated Apr. 22, 2014, and claims as pending for EP Application No. 14155798.3 as of Apr. 22, 2014.
Office Action for U.S. Appl. No. 13/280,274, filed Oct. 24, 2011, published as US 2012-0106289 on May 3, 2012, which Office Action is dated Aug. 30, 2012, and claims as pending for U.S. Appl. No. 13/280,274 as of Aug. 30, 2012.
Office Action for U.S. Appl. No. 12/038,648, filed Feb. 27, 2008. published as US 2008-0216898 on Sep. 11, 2008, which Office Action is dated Oct. 1, 2010, and claims as pending for U.S. Appl. No. 12/038,648 as of Oct. 1, 2010.
Ex Parte Quayle Action for U.S. Appl. No. 12/038,648, filed Feb. 27, 2008, published as 2008-0216898, on Sep. 11, 2008, which Office Action is dated Mar. 29, 2011, and claims as pending for U.S. Appl. No. 12/038,648 as of Mar. 29, 2011.
Invitation to Pay Additional Fees for Application No. PCT/US2008/055168 mailed Aug. 5, 2008.
International Search Report and Written Opinion for Application No. PCT/US2008/055168 mailed Nov. 10, 2008.
International Preliminary Report on Patentability for Application No. PCT/US2008/055168 mailed Sep. 11, 2009.

Examination Report for AU Application No. 2008231167 filed Feb. 27, 2008, which Examination Report is dated Jul. 30, 2012, and claims as pending for AU Application No. 2008231167 as of Jul. 30, 2012.
Office Action for CA Application No. 2682073 filed Sep. 24, 2009, which Office Action is dated Feburary 21, 2014, and claims as pending for CA Application No. 2682073 as of Feb. 21, 2014.
Office Action for CA Application No. 2682073 filed Sep. 24, 2009, which Office Action is dated Nov. 4, 2014, and claims as pending for CA Application No. 2682073 as of Nov. 4, 2014.
Examination Report for EP Application No. 08730848.2 filed Feb. 27, 2008, published as EP 2131890 on Dec. 16, 2009, which Examination Report is dated Dec. 30, 2011, and claims as pending for EP Application No. 08730848.2 as of Dec. 30, 2011.
Office Action for JP Application No. 2009-551818 filed Feb. 27, 2008, which Office Action is dated Oct. 16, 2012, and claims as pending for JP Application No. 2009-551818 as of Oct. 16, 2012.
Notice of Allowance for JP Application No. 2009-551818 filed Feb. 27, 2008, which Notice of Allowance is dated Apr. 26, 2013, and claims as allowed for JP Application No. 2009-551818 as of Apr. 26, 2013.
Office Action for JP Application No. 2013-119844 filed Jun. 6, 2013, unpublished as of Jun. 10, 2014, which Office Action is dated Jun. 10, 2014, and claims as pending for JP Application No. 2013-119844 as of Jun. 10, 2014.
Office Action for MX Application No. MX/A/2009/009219 filed Aug. 27, 2009, which Office Action is dated Dec. 3, 2014, and claims as pending for MX Application No. MX/A/2009/009219 as of Dec. 3, 2014.
Office Action for U.S. Appl. No. 12/038,474, filed Feb. 27, 2008, published as US 2008-0253427 on Oct. 16, 2008, which Office Action is dated Feb. 7, 2011, and claims as pending for U.S. Appl. No. 12/038,474 as of Feb. 7, 2011.
Office Action for U.S. Appl. No. 12/038,474, filed Feb. 27, 2008, published as US 2008-0253427 on Oct. 16, 2008, which Office Action is dated Sep. 1, 2011, and claims as pending for U.S. Appl. No. 12/038,474 as of Sep. 1, 2011.
Office Action for U.S. Appl. No. 12/038,474, filed Feb. 27, 2008, published as US 2008-0253427 on Oct. 16, 2008, which Office Action is dated May 15, 2012, and claims as pending for U.S. Appl. No. 12/038,474 as of May 15, 2012.
International Search Report and Written Opinion for Application No. PCT/US2008/055136 mailed Jul. 24, 2008.
International Preliminary Report on Patentability for Application No. PCT/US2008/055136 mailed Sep. 11, 2009.
Office Action for U.S. Appl. No. 13/619,266, filed Sep. 14, 2012, published as US 2013-0010825 on Jan. 10, 2013, which Office Action is dated Jul. 30, 2013, and claims as pending for U.S. Appl. No. 13/619,266 as of Jul. 30, 2013.
Office Action for U.S. Appl. No. 13/619,266, filed Sep. 14, 2012, published as US 2013-0010825 on Jan. 10, 2013, which Office Action is dated Apr. 15, 2014, and claims as pending for U.S. Appl. No. 13/619,266 as of Apr. 15, 2014.
Notice of Allowance for U.S. Appl. No. 13/619,266, filed May 11, 2010, published as US 2013-0010825 on Jan. 10, 2013, which Notice of Allowance is dated Nov. 7, 2014, and claims as allowed for U.S. Appl. No. 13/619,266 as of Nov. 7, 2014.
Office Action for U.S. Appl. No. 12/199,166, filed Aug. 27, 2008, published as US 2009-0107335 on Aug. 30, 2009 which Office Action is dated Oct. 11, 2011 and claims as pending for U.S. Appl. No. 12/199,166 as of Oct. 11, 2011.
Office Action for U.S. Appl. No. 12/199,166, filed Aug. 27, 2008, published as US 2009-0107335 on Aug. 30, 2009 which Office Action is dated May 2, 2012, and claims as pending for U.S. Appl. No. 12/199,166 as of May 2, 2012.
Office Action for U.S. Appl. No. 12/199,166, filed Aug. 27, 2008, published as US 2009-0107335 on Aug. 30, 2009 which Office Action is dated Nov. 2, 2012 and claims as pending for U.S. Appl. No. 12/199,166 as of Nov. 2, 2012.
Office Action for U.S. Appl. No. 12/199,166, filed Aug. 27, 2008, published as US 2009-0107335 on Aug. 30, 2009 which Office Action is dated Jun. 25, 2013, and claims as pending for U.S. Appl. No. 12/199,166 as of Jun. 25, 2013.

(56) References Cited

OTHER PUBLICATIONS

Office Action for U.S. Appl. No. 12/199,176, filed Aug. 27, 2008, published as 2010-0056975 on Mar. 4, 2010, which Office Action is dated Nov. 22, 2010, and claims as pending for U.S. Appl. No. 12/199,176 as of Nov. 22, 2010.
Office Action for U.S. Appl. No. 12/199,176, filed Aug. 27, 2008, published as 2010-0056975 on Mar. 4, 2010, which Office Action is dated Sep. 2, 2011, and claims as pending for U.S. Appl. No. 12/199,176 as of Sep. 2, 2011.
Office Action for U.S. Appl. No. 12/199,176, filed Aug. 27, 2008, published as 2010-0056975 on Mar. 4, 2010, which Office Action is dated Feb. 10, 2012, and claims as pending for U.S. Appl. No. 12/199,176 as of Feb. 10, 2012.
Invitation to Pay Additional Fees mailed Nov. 27, 2009 for Application PCT/US2009/004866.
International Search Report and Written Opinion mailed Jan. 27, 2010 for Application PCT/US2009/004866.
International Preliminary Report on Patentability for Application No. PCT/US2009/004866 mailed Mar. 10, 2011.
Office Action for MX Application No. MX/A/2014/004081 filed Apr. 3, 2014, which Office Action is dated Jul. 31, 2014, and claims as pending for MX Application No. MX/A/2014/004081 as of Jul. 31, 2014.
Invitation to Pay Additional Fees mailed Dec. 8, 2009 for Application PCT/US2009/004877.
International Search Report and Written Opinion mailed Feb. 12, 2010 for Application PCT/US2009/004877.
International Preliminary Report on Patentability for Application No. PCT/US2009/004877 mailed Mar. 10, 2011.
Examination Report for EP Application No. 07755392.3 filed Apr. 13, 2007, published as EP 2 010 247 on Jan. 7, 2009, which Examination Report is dated Sep. 7, 2011, and claims as pending for EP Application No. 07755392.3 as of Sep. 7, 2011.
Office Action for JP Application No. 2009-505495 filed Apr. 13, 2007, unpublished as of Aug. 3, 2012, which Office Action is dated May 8, 2012, and claims as pending for JP Application No. 2009-505495 as of May 8, 2012.
Office Action for MX Application No. MX/A/2008/013266 filed Apr. 13, 2007, unpublished as of Aug. 7, 2012, which Office Action is dated Aug. 7, 2012, and claims as pending for MX Application No. MX/A/2008/013266 as of Aug. 7, 2012.
Office Action for U.S. Appl. No. 11/787,212, filed Apr. 13, 2007, published as 2008-0175719 on Jul. 24, 2008, which Office Action is dated May 26, 2010, and claims as pending for U.S. Appl. No. 11/787,212 as of May 26, 2010.
Office Action for U.S. Appl. No. 11/787,212, filed Apr. 13, 2007, published as 2008-0175719 on Jul. 24, 2008, which Office Action is dated Feb. 7, 2011, and claims as pending for U.S. Appl. No. 11/787,212 as of Feb. 7, 2011.
Office Action for U.S. Appl. No. 11/787,213, filed Apr. 13, 2007, published as 2008-0058697 on Mar. 6, 2008, which Office Action is dated Mar. 18, 2010, and claims as pending for U.S. Appl. No. 11/787,213 as of Mar. 18, 2010.
Office Action for U.S. Appl. No. 11/787,112, filed Apr. 13, 2007, published as US 2007-253463 on Nov. 1, 2007, which Office Action is dated Nov. 21, 2008, and claims as pending for U.S. Appl. No. 11/787,112 as of Nov. 21, 2008.
Written Opinion for PCT/US2007/009107 mailed Aug. 17, 2007.
International Preliminary Report on Patentability for Application No. PCT/US2007/009107 mailed Oct. 23, 2008.
Partial European Search Report for EP Application No. 11150584.8 filed Oct. 10, 2008, published as EP 2319551 on May 11, 2011, which Search Report is dated Mar. 30, 2011, and claims as pending for EP Application No. 11150584.8 as of Mar. 30, 2011.
Extended European Search Report for EP Application No. 11150584.8 filed Oct. 10, 2008, published as EP 2319551 on May 11, 2011, which Search Report is dated Jul. 26, 2011, and claims as pending for EP Application No. 11150584.8 as of Jul. 26, 2011.
International Search Report and Written Opinion for Application No. PCT/US2008/011663 mailed Feb. 20, 2009.

International Preliminary Report on Patentability for Application No. PCT/US2008/011663 mailed Apr. 22, 2010.
Invitation to Pay Additional Fees for International Application No. PCT/US2009/000433 (published as WO 2009/094179), mailed Jun. 4, 2009.
International Search Report and Written Opinion for International Application No. PCT/US2009/000433 (published as WO 2009/094179), mailed Sep. 25, 2009.
International Preliminary Report on Patentability for Application No. PCT/US2009/000433 mailed Aug. 5, 2010.
Office Action for EP Application No. 08730761.7 filed Feb. 26, 2008, published as EP 2131893 on Dec. 16, 2009, which Office Action is dated Jul. 26, 2013, and claims as pending for EP Application No. 08730761.7 as of Jul. 26, 2013.
Office Action for U.S. Appl. No. 11/871,821, filed Oct. 12, 2007, published as US 20080240929 on Oct. 2, 2008, which Office Action is dated Sep. 23, 2009, and claims as pending for U.S. Appl. No. 11/871,821 as of Sep. 23, 2009.
International Search Report and Written Opinion for Application No. PCT/US2008/055021 mailed Jul. 23, 2008.
International Preliminary Report on Patentability for Application No. PCT/US2008/055021 dated Sep. 11, 2009.
Office Action for U.S. Appl. No. 11/871,828, filed Oct. 12, 2007, published as US 2008-0208111 on Aug. 28, 2008, which Office Action is dated Mar. 11, 2010, and claims as pending for U.S. Appl. No. 11/871,828 as of Mar. 11, 2010.
Office Action for U.S. Appl. No. 11/871,828, filed Oct. 12, 2007, published as US 2008-0208111 on Aug. 28, 2008, which Office Action is dated Nov. 26, 2010, and claims as pending for U.S. Appl. No. 11/871,828 as of Nov. 26, 2010.
Office Action for U.S. Appl. No. 12/730,197, filed Mar. 23, 2010, published as US 2010-0327849 on Dec. 30, 2010, which Office Action is dated Nov. 17, 2011, and claims as pending for U.S. Appl. No. 12/730,197 as of Nov. 17, 2011.
International Search Report and Written Opinion for International Application No. PCT/US2010/054772 mailed May 9, 2011.
International Preliminary Report on Patentability for International Application No. PCT/US2010/054772 issued May 1, 2012.
Invitation to Pay Additional Fees for PCT Application No. PCT/US2012/039369 mailed Sep. 27, 2012.
Office Action for U.S. Appl. No. 13/480,454, filed May 24, 2012, published as US 2013-0020237 on Jan. 24, 2013, which Office Action is dated Dec. 24, 2014, and claims as pending for U.S. Appl. No. 13/480,454 as of Dec. 24, 2014.
Bengtsson et al., Haemo dialysis software architecture design experiences. Proceedings of the 1999 International Conference on Software Engineering. ACM New York, NY. 1999:516-525.
Choppy et al., Architectural patterns for problem frames. IEE Proceedings: Software. Aug. 2005;152(4): 190-208.
Gentilini et al., Multitasked closed-loop control in anesthesia. IEEE Eng Med Biol Mag. Jan.-Feb. 2001;20(1):39-53.
Harel, Statecharts: A visual formalism for complex systems. Science of Computer Programming 1987;8:231-274.
Krasner et al., A cookbook for using the model-view-controller user interface paradigm in smalltalk-80. JOOP. Aug. 1988;1(3):26-49.
Misra, The basics of hemodialysis equipment. Hemodial Int. Jan. 2005;9(1):30-6.
Smith, Temperature Correction in Conductivity Measurements. Limnology and Oceanography. 1962;7(3):330-334.
Office Action for AU Application No. 2014200376 filed Jan. 22, 2014, which Office Action is dated Mar. 27, 2015, and claims as pending for AU Application No. 2014200376 as of Mar. 27, 2015.
Extended European Search Report for EP Application No. 13150786.5 filed Apr. 13, 2007, which Search Report is dated Mar. 28, 2013, and claims as pending for EP Application No. 13150786.5 as of Mar. 28, 2013.
Office Action for AU Application No. 2008312005 filed Oct. 10, 2008, which Office Action is dated Jan. 9, 2013, and claims as pending for AU Application No. 2008312005 as of Jan. 9, 2013.
Office Action for CA Application No. 2702385 filed Apr. 12, 2010, which Office Action is dated Nov. 20, 2014, and claims as pending for CA Application No. 2702385 as of Nov. 20, 2014.

(56) References Cited

OTHER PUBLICATIONS

Office Action for CN Application No. 20880121285.7 filed Oct. 10, 2008, published as CN 101986776, which Office Action is dated Oct. 10, 2012, and claims as pending for CN Application No. 20880121285.7 as of Oct. 10, 2012.
Office Action for CN Application No. 20880121285.7 filed Oct. 10, 2008, published as CN 101986776, which Office Action is dated Aug. 14, 2013, and claims as pending for CN Application No. 20880121285.7 as of Aug. 14, 2013.
Office Action for CN Application No. 20880121285.7 filed Oct. 10, 2008, published as CN 101986776, which Office Action is dated May 14, 2014, and claims as pending for CN Application No. 20880121285.7 as of May 14, 2014.
Examination Report for EP Application No. 08838971.3 filed Oct. 10, 2008, published as EP 2197513 on Jun. 23, 2010, which Examination Report is dated Jun. 21, 2013, and claims as pending for EP Application No. 08838971.3 as of Jun. 21, 2013.
Examination Report for EP Application No. 11150584.8 filed Jan. 11, 2011, published as EP 2319551 on May 11, 2011, which Examination Report is dated Oct. 16, 2012, and claims as pending for EP Application No. 11150584.8 as of Oct. 16, 2012.
Office Action for JP Application No. 2010-528896 filed Oct. 10, 2008, which Office Action is dated Feb. 26, 2013, and claims as pending for JP Application No. 2010-528896 as of Feb. 26, 2013.
Office Action for KR Application No. 10-2010-7010384 filed May 11, 2010, which Office Action is dated Oct. 30, 2014, and claims as pending for KR Application No. 10-2010-7010384 as of Oct. 30, 2014.
International Search Report and Written Opinion for Application No. PCT/US2009/000439 mailed Jun. 3, 2009.
International Preliminary Report on Patentability for Application No. PCT/US2009/000439 mailed Aug. 5, 2010.
Examination Report for EP Application No. 08730761.7 filed Feb. 26, 2008, published as EP 2131893 on Dec. 16, 2009, which Examination Report is dated Sep. 23, 2011, and claims as pending for EP Application No. 08730761.7 as of Sep. 23, 2011.
Office Action for AU Application No. 2012327182 filed Apr. 12, 2013, which Office Action is dated Jun. 30, 2014, and claims as pending for AU Application No. 2012327182 as of Jun. 30, 2014.
Invitation to Pay Additional Fees for PCT/US2012/063336 filed Nov. 2, 2012, which Invitation to Pay Additional Fees is dated Feb. 21, 2013, and claims as pending for PCT/US2012/063336 as of Feb. 21, 2013.
International Search Report and Written Opinion for PCT/US2012/063336 mailed Sep. 20, 2013.
International Preliminary Report on Patentability for PCT/US2012/063336 mailed May 15, 2014.
Office Action for JP Application No. 2015-021182 filed Feb. 5, 2015, which Office Action is dated Jan. 5, 2016, and claims as pending for JP Application No. 2015-021182 as of Jan. 5, 2016.
Examination Report for EP Application No. 08730848.2 filed Feb. 27, 2008, published as EP 2131890 on Dec. 16, 2009, which Examination Report is dated Aug. 19, 2016, and claims as pending for EP Application No. 08730848.2 as of Aug. 19, 2016.

SENSOR APPARATUS SYSTEMS, DEVICES AND METHODS

CROSS-REFERENCE TO RELATED APPLICATIONS

This application is a continuation of U.S. patent application Ser. No. 13/619,266, filed Sep. 14, 2012 and issued as U.S. Pat. No. 8,992,075 on Mar. 31, 2015, and entitled Sensor Apparatus Systems, Devices and Methods, which is a continuation of U.S. patent application Ser. No. 12/038,474, filed Feb. 27, 2008 and issued as U.S. Pat. No. 8,491,184 on Jul. 23, 2013, and entitled Sensor Apparatus Systems, Devices and Methods, which is a continuation-in-part of patent application Ser. No. 11/871,821, filed Oct. 12, 2007, now abandoned, and entitled Sensor Apparatus Systems, Devices and Methods, which claims priority from the following United States Provisional Patent Applications, all of which are hereby incorporated herein by reference in their entireties:

U.S. Provisional Patent Application No. 60/904,024 entitled Hemodialysis System and Methods filed on Feb. 27, 2007; and U.S. Provisional Patent Application No. 60/921,314 entitled Sensor Apparatus filed on Apr. 2, 2007.

This application is also related to the following United States Patent Applications, which are hereby incorporated herein by reference in their entireties: U.S. patent application Ser. No. 11/871,712, filed Oct. 12, 2007 and issued as U.S. Pat. No. 8,317,492 on Nov. 27, 2012, entitled Pumping Cassette; U.S. patent application Ser. No. 11/871,787, filed Oct. 12, 2007 and entitled Pumping Cassette; U.S. patent application Ser. No. 11/871,793, filed Oct. 12, 2007 and issued as U.S. Pat. No. 8,888,470 on Nov. 18, 2014, and entitled Pumping Cassette; U.S. patent application Ser. No. 11/871,803, filed Oct. 12, 2007 and issued as U.S. Pat. No. 7,967,022 on Jun. 28, 2011 and entitled Cassette System Integrated Apparatus; U.S. patent application Ser. No. 11/871,828, filed Oct. 12, 2007 and issued as U.S. Pat. No. 8,366,655 on Feb. 5, 2013, and entitled Peritoneal Dialysis Sensor Apparatus, Systems, Devices and Methods; U.S. patent application Ser. No. 12/038,648, filed Feb. 27, 2008 and issued as U.S. Pat. No. 8,042,563 on Oct. 25, 2011 and entitled Cassette System Integrated Apparatus; and U.S. patent application Ser. No. 12/072,908, filed Feb. 27, 2008 and issued as U.S. Pat. No. 8,246,286 on Aug. 21, 2012 and entitled Hemodialysis System and Methods.

TECHNICAL FIELD

The present invention relates to sensor systems, devices, and methods, and more particularly to systems, devices, and methods for sensors, sensor apparatus, and sensor apparatus systems.

BACKGROUND ART

In many applications, the temperature of a media, whether a solid, liquid or gas, is determined. One method is introducing a temperature sensor apparatus or probe to the medium being measured. For accuracy, close proximity of the sensor to the subject media is desired. However, this method may lead to contamination of the sensor apparatus and/or the fluid. Additional problems with harsh media or problems with the accuracy of the device used exist.

The concentration of a known compound in a media, whether fluid or otherwise, can be determined through measuring the conductivity of the fluid. Determining the conductivity of a material can also provide useful information such as the composition or presence of a particular compound in a material or irregularities in the conductive material between conductivity sensing probes. The presence, absence or variation of conductivity can also be a useful determinant of anomalies in a system.

There is a need for an apparatus that can both sense the temperature and the conductivity of a fluid or other media. There is a desire for a combination temperature and conductivity sensor that avoid contamination with the subject media and is compact. Also, there is a desire for an accurate temperature sensing device.

Additionally, there is a need for an accurate measurement apparatus to measure the temperature, conductivity, and/or other condition of a subject media while avoiding contamination between with the measurement apparatus and the subject media. There is also a need for an accurate measurement apparatus that can measure the temperature, conductivity, and/or other condition of a subject media where such subject media is contained in and/or flowing through a disposable component such that part or all of the sensor apparatus can be reused and need not be disposed of along with the disposable component.

SUMMARY OF THE INVENTION

In accordance with one aspect of the invention there is provided a sensor apparatus system for determining one or more properties of a subject fluid in a cassette, the system comprising a probe housing; a thermal sensor in said probe housing having a sensing end and a connector end; a probe tip thermally coupled to said sensing end of the thermal sensor and attached to said probe housing, the probe tip adapted for thermal coupling with an inner surface of a well installed in a cassette; and at least two leads connected to said connector end of said thermal sensor, whereby thermal energy is transferred from said well to said thermal sensor and whereby temperature information is conveyed through said leads. In various alternative embodiments, the sensing probe may further include a third lead attached to one of the probe housing, the thermal sensor, and the probe tip for permitting conductivity sensing. Alternatively, the sensing probe may further include a conductivity sensor attached to one of the probe housing, the thermal sensor, and the probe tip for permitting conductivity sensing; and a third lead attached to the conductivity sensor for transmitting conductivity information. A urethane resin may be included between said probe tip and said probe housing. The probe tip may include a flange for mating with the housing.

In various alternative embodiments of the sensor apparatus system described above, thermal epoxy may be included between said thermal sensor and said probe tip. The probe tip may be copper, steel, or a metal including at least one of silver, copper, steel, and stainless steel. In various embodiments, the housing may be plastic or metal. The housing may include a flange disposed about said probe housing, and a spring may be used in conjunction with the flange. The housing may include an integrated flexible member.

Some embodiments of this aspect of the present invention include a well of a predetermined size and shape. The well mates with the probe and the probe tip is thermal coupled to said well.

In accordance with one aspect of the present invention the well includes a hollow housing of a thermally conductive material. The housing has an outer surface and an inner surface. The inner surface is a predetermined shape so as to form a mating relationship with a sensing probe. The mating thermally couples the inner surface with a sensing probe.

Some embodiments of this aspect of the present invention include a predetermined volume of thermal grease on the inner surface of the well.

In accordance with one aspect of the present invention, method for determining temperature and conductivity of a subject media in a cassette is described. The method includes the following steps: installing at least one well in a cassette; thermally coupling a well and a sensing probe such that temperature and conductivity can be determined; transferring thermal and conductivity signals through at least 3 leads from the sensing probe; and determining temperature and conductivity using the signals.

In accordance with another aspect of the present invention, a method for detecting air in a fluid line contained in a cassette is described. The method includes the following steps: installing at least one well in a cassette; thermally coupling at least two wells located in a fluid line to sensing probes such that temperature and conductivity can be determined; transferring conductivity signals through at least 3 leads from the sensing probes; determining conductivity for each sensing probe; calculating the difference of conductivity from each sensing probe; and determining if the difference exceeds a threshold.

In accordance with another aspect of the invention there is provided apparatus comprising a fluid conduit in a cassette including a well for at least one of transmitting temperature and permitting conductivity sensing of fluid passing through the conduit, wherein the well is adapted for interconnection with a sensor.

In various alternative embodiments, the apparatus may be configured so that a portion of the well comes into contact with fluid in the conduit or so that no portion of the well comes into contact with fluid in the conduit. The fluid conduit in the cassette may include plastic tubing or metal tubing.

In various embodiments, the cassette containing the fluid line comprises a rigid body overlaid on one or more sides with a flexible diaphragm. In various embodiments the flexible diaphragm cassette includes one or more pump chambers and/or one or more value stations. In various embodiments, one or more wells are positioned on the edge of the cassette. In certain of these embodiments, one or more wells are positioned on the bottom edge of the cassette.

In various embodiments, the cassette has a rigid front and/or back plate. One or more wells may be installed in the rigid cassette. Alternatively, one or more sensor leads may be installed in the rigid cassette. In various embodiments, the rigid cassette may contain one or more pod pumps.

The cassette and the well may be integrally formed from the same material.

Alternatively, the well may be coupled to the cassette, e.g., using at least one of press fit connection, flexible tabs, adhesive, ultrasonic weld, and a retaining plate and fastener. An o-ring may be disposed between the well and the fluid conduit. The o-ring may include one of a round cross-section, a square cross-section, and an X-shaped cross-section. The well may include a groove to receive a portion of the o-ring. A portion of the well in contact with the conduit may be flexible so as to deform the conduit and may include a plurality of cuts to provide such flexibility.

In accordance with another aspect of the invention there is provided a fluid pumping apparatus comprising at least one pump and a well for at least one of transmitting temperature and permitting conductivity sensing of fluid passing through the conduit, wherein the well is adapted for interconnection with a sensor. In various alternative embodiments, the at least one pump may include at least one pod pump and may include a pair of pod pumps. The at least one pump and the well may be integrated into a cassette.

In accordance with another aspect of the invention there is provided a sensing system comprising at least one sensing probe and at least one well installed in a cassette, the well in communication with the sensing probe for at least one of thermal sensing and conductivity sensing.

In accordance with another aspect of the invention there is provided a sensor manifold comprising a cassette and at least one sensing probe for at least one of thermal sensing and conductivity sensing. In various embodiments, the sensor manifold contains two or more fluid paths and two or more sensing probes for at least one of thermal sensing and conductivity sensing. In various embodiments, the sensor manifold is passive with respect to controlling the flow of the fluid in the fluid paths within the cassette. In such embodiments, the sensor manifold may be free from valves and pumping mechanisms. In various embodiments, the sensor manifold may comprise a cassette with a rigid front and/or back plate and a mid-plate. In various embodiments, the sensor manifold may comprise electrical circuits connected to the sensing probes. In certain of these embodiments, the sensor manifold may comprise a printed circuit board.

These aspects of the invention are not meant to be exclusive or comprehensive and other features, aspects, and advantages of the present invention are possible and will be readily apparent to those of ordinary skill in the art when read in conjunction with the following description, the appended claims, and the accompanying drawings.

BRIEF DESCRIPTION OF THE DRAWINGS

The foregoing features of the invention will be more readily understood by reference to the following detailed description, taken with reference to the accompanying drawings, wherein.

It should be noted that the foregoing figures and the elements depicted therein are not necessarily drawn to consistent scale or to any scale. Unless the context otherwise suggests, like elements are indicated by like numerals.

DETAILED DESCRIPTION OF SPECIFIC EMBODIMENTS

Figure 1A:
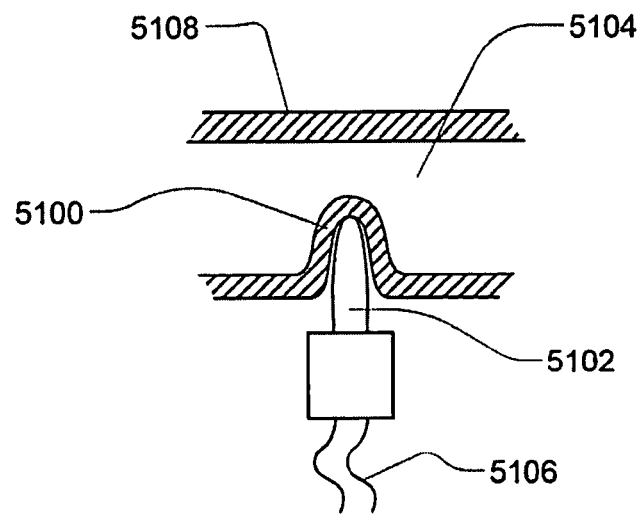
FIGS. 1A and 1B are embodiments of the sensing apparatus where the thermal well is a continuous part of the fluid line.

Definitions. As used in this description and the accompanying claims, the following terms shall have the meanings indicated, unless the context otherwise requires:

"Spheroid" means any three-dimensional shape that generally corresponds to a oval rotated about one of its principal axes, major or minor, and includes three-dimensional egg shapes, oblate and prolate spheroids, spheres, and substantially equivalent shapes.

"Hemispheroid" means any three-dimensional shape that generally corresponds to approximately half a spheroid.

"Spherical" means generally spherical.

"Hemispherical" means generally hemispherical.

"Fluid" shall mean a substance, a liquid for example, that is capable of being pumped through a flow line. Blood is a specific example of a fluid.

A "patient" includes a person or animal from whom, or to whom, fluid is pumped, whether as part of a medical treatment or otherwise.

"Subject media" is any material, including any fluid, solid, liquid or gas, that is in contact directly with a sensing probe or indirectly via thermal wells, sensor extension pins, and other such devices for transferring information regarding one or more characteristics of such subject media to one or more sensors.

Various aspects of the present invention are described below with reference to various exemplary embodiments. It should be noted that headings are included for convenience and do not limit the present invention in any way.

Various embodiments of sensors, including thermal and/or conductivity sensors, are described. Such thermal/conductivity sensors can be used in a wide variety of applications and are by no means limited to thermal/conductivity measurements of fluids or to thermal/conductivity measurements in any particular context. Additionally, various embodiments of systems, devices, and methods for sensor interface, including direct sensor contact, sensor interface through the use of a thermal well, or otherwise with various disposable and reusable components are described. Such systems, devices, and methods for sensor interface can be used with a wide variety of sensors and in a wide variety of applications. Such systems, devices, and methods for sensor interface are by no means limited to use with the various sensor embodiments or for use in any particular context.

1. Thermal Wells

In one exemplary embodiment, a thermal well is used to accommodate a sensor probe, such as a temperature sensing probe. The thermal well comes into direct contact with a subject media (e.g., a liquid such as blood or dialysate) and the sensing probe does not. Based on heat transfer dictated in large part by the thermodynamic properties of the thermal well and sensing probe construction, the sensing probe can determine the properties of the subject media without coming into direct contact with the subject media. The accuracy and efficiency of the sensor apparatus arrangement depends on many factors including, but not limited to: construction, material and geometry of both the probe and the thermal well.

Figure 1B:
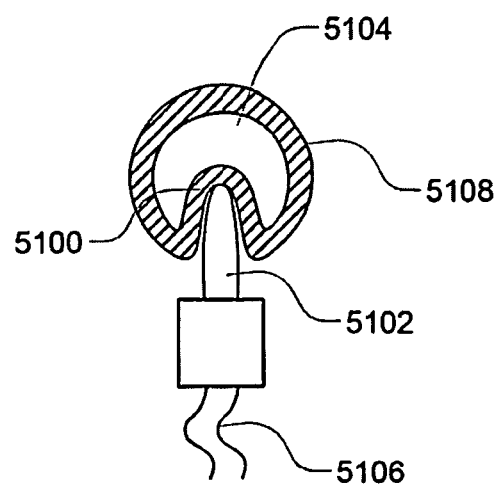

Referring now to FIGS. 1A and 1B, two embodiments of the sensor apparatus which includes the thermal well 5100 and the sensing probe 5102, are shown in relation to a fluid line 5108. In these embodiments, the thermal well 5100 is integrated into the fluid line 5108. However, in other embodiment, some described below, the thermal well 5100 is not completely integrated into the fluid line 5108, i.e., the thermal well 5100 can be made from different materials as compared with the fluid line 5108. In alternate embodiments, the thermal well 5100 is not integrated into any fluid line but can be integrated into anything or nothing at all. For example, in some embodiments, the thermal well 5100 can be integrated into a container, chamber, machine, protective sleeve, fluid pump, pump cassette, disposable unit, manifold, or other assembly, sub-assembly, or component. For purposes of the description, an exemplary embodiment is described for illustrative purposes. The exemplary embodiment includes the embodiment where the thermal well 5100 is in a fluid line. However, the sensor apparatus and the thermal well can be used outside of a fluid line.

Referring now to FIG. 1A, a side view showing a thermal well 5100 formed in a fluid line 5108 which provides the space 5104 for subject media to flow through, and a sensing probe 5102 is shown. Data from the sensing probe is transmitted using at least one lead 5106. An end view of FIG. 1A is shown in FIG. 1B.

In this embodiment, the thermal well 5100 is one piece with the fluid line 5108. The total area of the thermal well 5100 can vary. By varying the geometry of the thermal well 5100, the variables, including, but not limited to, the thermal conductivity characteristic of the thermal well 5100 and thus, the heat transfer between the thermal well 5100 and the sensing probe 5102 will vary. As described in more detail below, the material construction of the thermal well 5100 is another variable in the sensor apparatus.

In some embodiments, the fluid line 5108 is made from a material having a desired thermal conductivity. This material may vary depending on the purpose. The material can be anything including, but not limited to, any plastic, ceramic, metals or alloys of metals or combinations thereof.

Figure 2A:
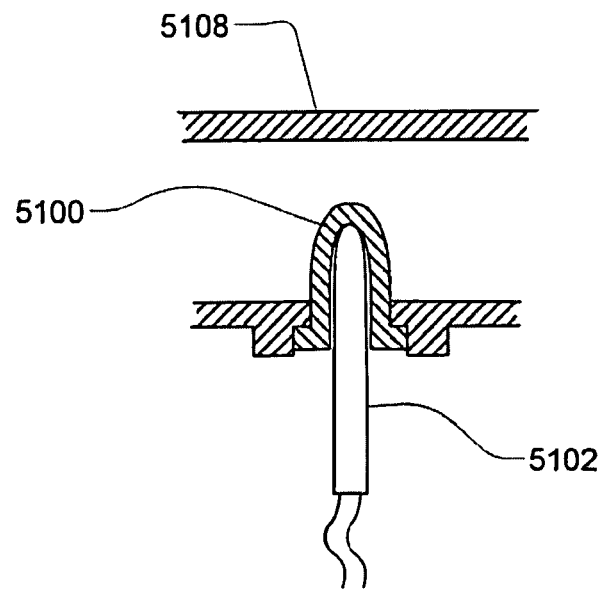
FIGS. 2A and 2B are embodiments of the sensing apparatus where the thermal well is a separate part from the fluid line.
Figure 2B:
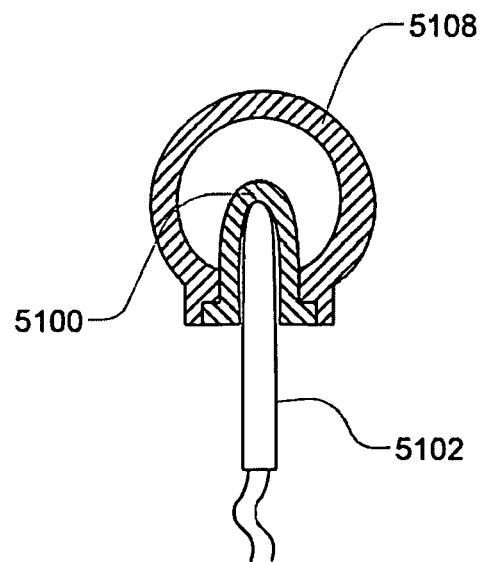

Referring now to FIGS. 2A and 2B, in these embodiments, the fluid line 5108 and the thermal well 5100 are separate parts. In some embodiments, the fluid line 5108 and the thermal well 5100 are made from different materials.

FIGS. 1A-1B and FIGS. 2A-2B show relatively simple embodiments of the sensor apparatus. Thus, for these embodiments, the sensing apparatus includes a thermal well 5100 and a sensing probe 5102 where the thermal well either is integrated as one continuous part with the fluid line 5108 or is a separate part from the fluid line 5108. However, many embodiments of the sensor apparatus are contemplated. Much of the various embodiments include variations on the materials and the geometries of the thermal well 5100 and/or the sensing probe 5102. These variations are dictated by multiple variables related to the intended use for the sensor apparatus. Thus, the subject media and the constraints of the desired sensor, for example, the accuracy, time for results and the fluid flow and subject media characteristics are but a sampling of the various constraints that dictate the embodiment used. In most instances, each of the variables will affect at least one part of the embodiment of the sensor apparatus.

Thus, multiple variables affect the various embodiments of the sensor apparatus, these variables include but are not limited to: 1) geometry of the thermal well; 2) material composition of the thermal well; 3) material composition of the sensing probe; 4) desired flow rate of the subject media; 5) length and width of the thermal well; 6) desired accuracy of the sensing probe; 7) wall thicknesses; 8) length and width of the sensing probe; 9) cost of manufacture; 10) subject media composition and characteristics including tolerance for turbulence; 11) geometry of sensing probe; and 12) desired speed of readings.

In the foregoing, various embodiments of the sensor apparatus are described. The description is intended to provide information on the affect the variables have on the sensor apparatus embodiment design. However, these are but exemplary embodiments. Many additional embodiments are contemplated and can be easily designed based on the intended use of the sensor apparatus. Thus, by changing one or more of the above mentioned partial list of variables, the embodiment of the sensor apparatus may vary.

Figure 3A:
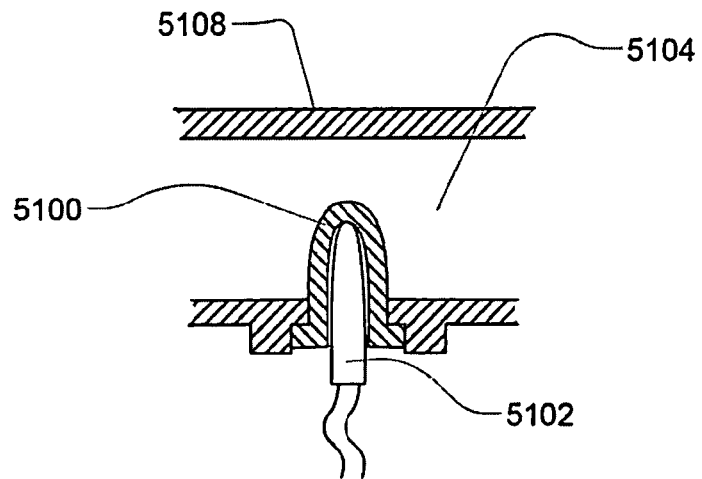
FIGS. 3A and 3B are embodiments of the sensing apparatus showing various lengths and widths of the thermal well.
Figure 3B:
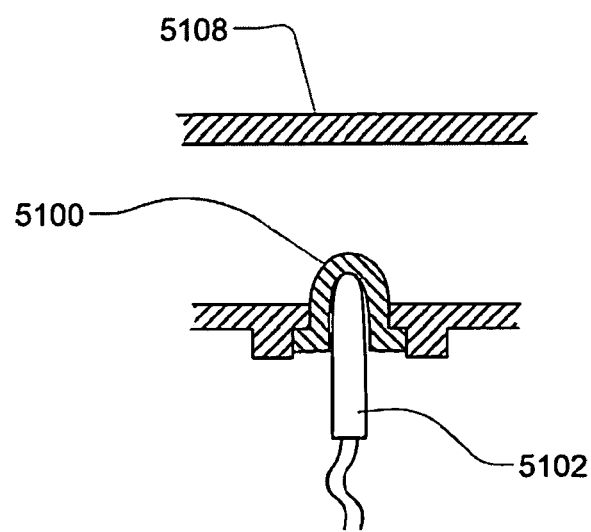

Referring now to FIGS. 3A and 3B, two embodiments of the thermal well 5100 are shown as different parts from the fluid line 5108. These embodiments show two geometries of the thermal well 5100. In FIG. 3A, the geometry includes a longer thermal well 5100. In FIG. 3B, the thermal well 5100 geometry is shorter. The length and width of the thermal well 5100 produce varying properties and accuracies of the thermal conductivity between the thermal well 5100 and the sensing probe 5102. Depending on the use of the sensor apparatus, the thermal well 5100 geometry is one variable.

Referring now to FIG. 3A, the longer thermal well 5100 generally provides a greater isolation between the subject media temperature in the fluid line 5104 and the ambient temperature. Although the longer thermal well 5100 geometry shown in FIG. 3A may be more accurate, the embodiment shown in FIG. 3B may be accurate enough for the purpose at hand. Thus, the length and width of the thermal well 5100 can be any length and width having the desired or tolerable accuracy characteristics. It should be understood that two extremes of length are shown in these embodiments; however, any length is contemplated. The description herein is meant to explain some of the effects of the variables.

Still referring to FIGS. 3A and 3B, the longer thermal well 5100 shown in FIG. 3A may impact the fluid flow of the subject media in the fluid line 5108 to a greater degree than the embodiment shown in FIG. 3B. It should be understood that the length of the thermal well 5100 may also impact the turbulence of the fluid flow. Thus, the length and width of the thermal well 5100 may be changed to have greater or lesser impact on the fluid flow and turbulence of the fluid, while mitigating the other variables.

The shape of the thermal well 5100 is also a variable. Any shape desired is contemplated. However, the shape of the thermal well 5100, as with the other variables, is determined in part based on the intended use of the sensor apparatus. For purposes of description, an exemplary embodiment is described herein. However, the shape in the exemplary embodiment is not meant to be limiting.

Figure 4:
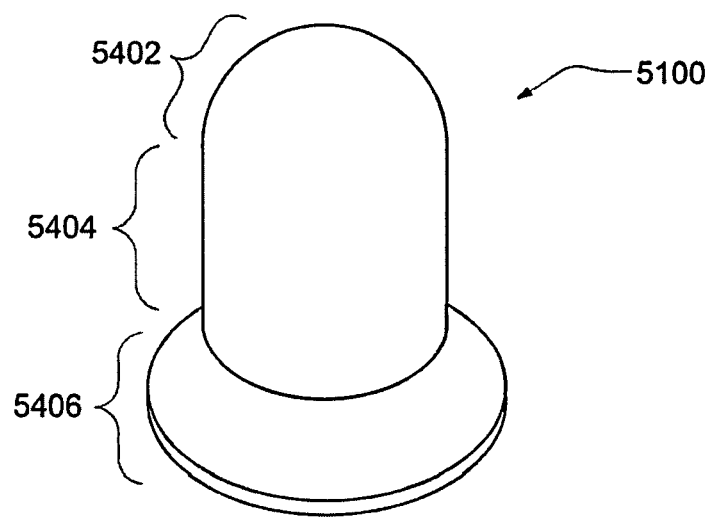
FIG. 4 is a pictorial view of a thermal well according to one embodiment of the sensing apparatus.

Referring now FIG. 4 for purposes of description, the thermal well 5100 has been divided into 3 zones. The top zone 5402 communicates with the sensing probe (not shown); the middle zone 5404 provides the desired length of the thermal well 5100. As described above, the length may dictate the level of protrusion into the fluid path. The length is dictated in part by the desired performance characteristics as discussed above. The middle zone 5404 also isolates the top zone 5402 from the ambient. The middle zone 5404 may also serve to locate, fasten or seal the thermal well 5100 into the fluid line (shown as 5108 in FIGS. 1A-1B).

The bottom zone 5406, which in some embodiments may not be necessary (see FIG. 7K) thus, in these embodiments, the middle zone 5404 and the bottom zone 5406 may be a single zone. However, in the exemplary embodiment, the bottom zone 5406 is shaped to aid in press fitting the thermal well into an area in the fluid line and may locate and/or fasten the thermal well 5100 into the fluid line 5108. In other embodiments, zone 5406 may be formed to facilitate various joining methods (see FIGS. 7A-7J, 7L-7S).

Figure 5:
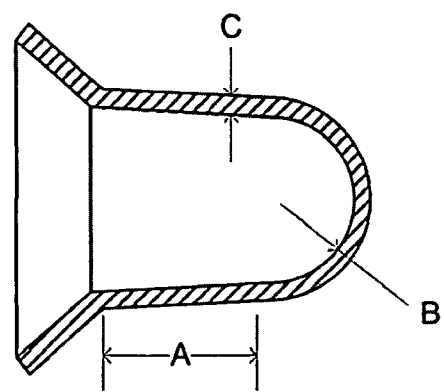
FIG. 5 is a cross sectional view of an exemplary embodiment of the thermal well.

Referring now to FIG. 5 a cross section of the exemplary embodiment of the thermal well 5100 is shown. The dimensions of the exemplary embodiment of the thermal well 5100 include a length A of approximately 0.113 inches (with a range from 0-0.379 inches), a radius B of approximately 0.066 inches and a wall thickness C ranging from approximately 0.003-0.009 inches. These dimensions are given for purposes of an exemplary embodiment only. Depending on the variables and the intended use of the sensing apparatus, the thermal well 5100 dimensions may vary, and the various embodiments are not necessarily proportional.

In some embodiments, the wall thickness can be variable, i.e., the wall thickness varies in different locations of the thermal well. Although these embodiments are shown with variable thicknesses in various locations, this is for description purposes only. Various embodiments of the thermal well may incorporate varying wall thickness in response to variables, these varying wall thicknesses can be "mixed and matched" depending on the desired properties of the sensing apparatus. Thus, for example, in some embodiments, a thinner zone 5404 may be used with thinner zone 5406 and vice-versa. Or, any other combination of "thinner" and "thicker" may be used. Also, the terms used to describe the wall thicknesses are relative. Any thickness desired is contemplated. The figures shown are therefore for descriptive purposes and represent two embodiments where many more are contemplated.

Figure 6A:
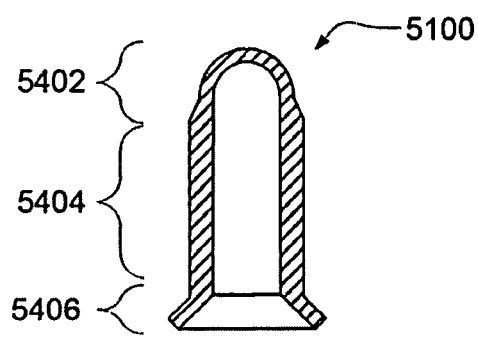
FIGS. 6A and 6B show section views of embodiments of thermal wells having variable wall thickness.
Figure 6B:
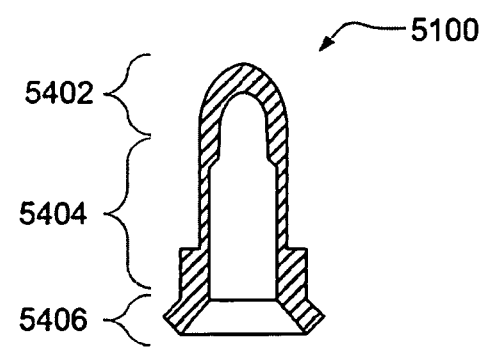

Referring now to FIGS. 6A and 6B, zone 5402 can be thicker or thinner as desired. The thinner zone 5402, amongst other variables, generally provides for a faster sensing time while a thicker zone may be useful for harsh environments or where sensor damping is desired. Zone 5404 may be thicker, amongst other variables, for greater strength or thinner for, amongst other variables, greater isolation from ambient. Zone 5406 can be thinner or thicker depending on the fastening method used.

Figure 7A:
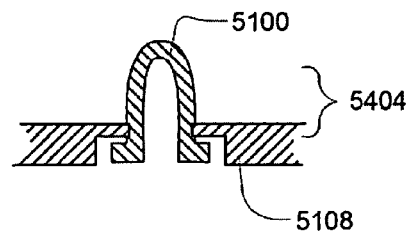
FIGS. 7A-7S are sectional views of various embodiments of the thermal well embedded in a fluid line.
Figure 7B:
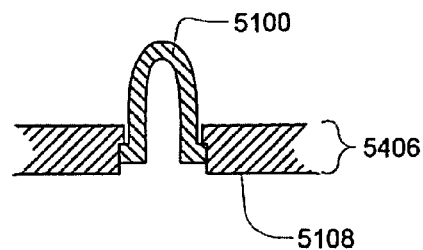
Figure 7C:
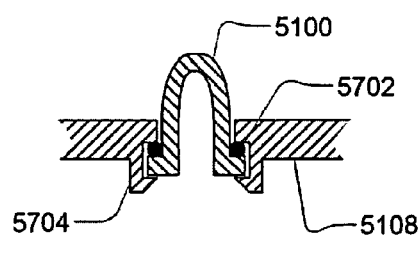
Figure 7D:
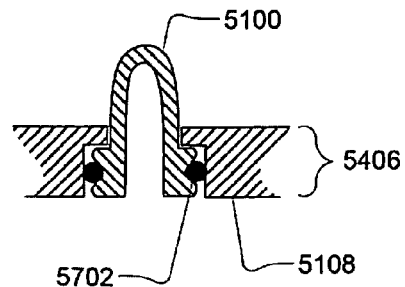
Figure 7E:
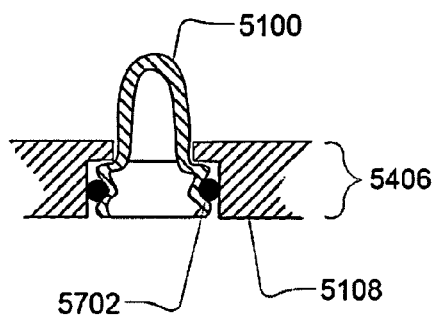

The thermal well 5100, in practice, can be embedded into a fluid line 5108, as a separate part from the fluid line 5108. This is shown and described above with respect to FIGS. 2A-2B. Various embodiments may be used for embedding the thermal well 5100 into the fluid line 5108. Although the preferred embodiments are described here, any method or process for embedding a thermal well 5100 into a fluid line 5108 can be used. Referring now to FIGS. 7A-7S, various configurations for embedding the thermal well 5100 into the fluid line 5108 are shown. For these embodiments, the thermal well 5100 can be made from any materials, including but not limited to, plastic, metal, ceramic or a combination thereof. The material may depend in some part on the compatibility with the intended subject media. The fluid line 5108, in these embodiments, may be made from plastic, metal, or any other material that is compatible with the subject media.

Referring first to FIG. 7A, the thermal well 5100 is shown press fit into the fluid line 5108 using the zone 5404 (shown in FIG. 4). In FIG. 7B, the thermal well 5100 is shown press fit into the fluid line 5108 using the zone 5406. Referring now to FIG. 7C, the thermal well 5100 is shown retained in the fluid line 5108 with flexible tabs 5704, an O-ring is also provided. Referring now to FIG. 7D, the thermal well 5100 is shown inserted into the fluid line 5108 with an O-ring 5702. The thermal well 5100 is also shown as an alternate embodiment, where the thermal well 5100 zone 5406 includes an O-ring groove. The O-ring groove can be cut, formed, spun, cast or injection molded into the thermal well, or formed into the thermal well 5100 by any other method. FIG. 7E shows a similar embodiment to that shown in FIG. 7D, however, the O-ring groove is formed in zone 5406 rather than cut, molded or cast as shown in FIG. 7D.

Figure 7F:
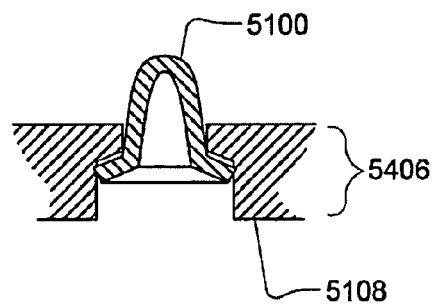
Figure 7G:
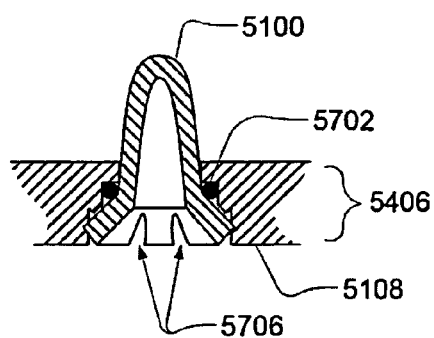

Referring now to FIG. 7F, the thermal well 5100 is shown press fit into the fluid line 5108, zone 5406 includes flexibility allowing the edge of zone 5406 to deform the material of the fluid line 5108. Referring now to FIG. 7G, the thermal well 5100 includes cuts 5706 on the zone 5406 providing flexibility of the zone 5406 for assembly with the fluid line 5108. An O-ring 5702 is also provided. Although two cuts are shown, a greater number or fewer cuts are used in alternate embodiments.

Figure 7H:
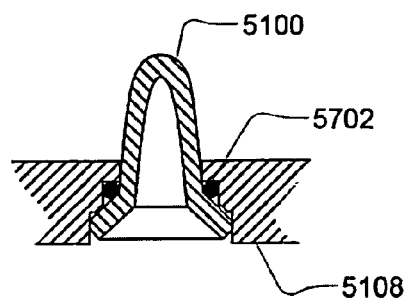
Figure 7I:
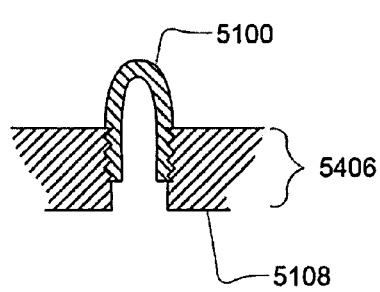

Referring now to FIG. 7H, the embodiment shown in FIG. 7F is shown with the addition of an O-ring 5702. Referring to FIG. 7I, the thermal well 5100 is shown insert molded in the fluid line 5108. Zone 5406 is formed to facilitate or enable assembly by insert molding.

Figure 7J:
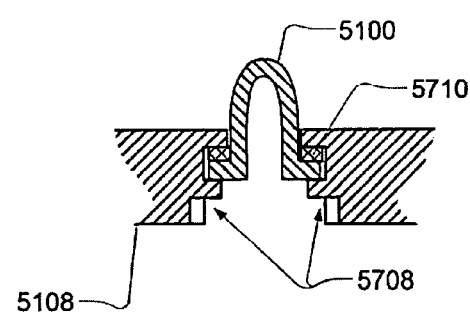

FIG. 7J shows an embodiment where the thermal well 5100 is heat staked 5708 to retain the thermal well 5100 in the fluid line 5108. In some embodiments of FIG. 7J, an O-ring 5710 is also included. In this embodiment, the O-ring 5710 has a rectangular cross section. However, in alternate embodiments, the O-ring may have a round or X-shaped cross section. Likewise, in the various embodiments described herein having an O-ring, the O-ring in those embodiments can have a round, rectangular or X-shaped cross section, or any cross sectional shape desired.

Figure 7K:
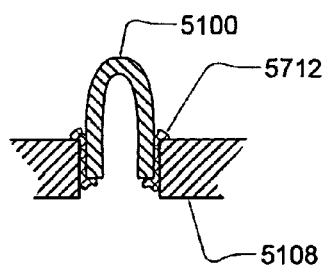

Referring now to FIG. 7K, the thermal well 5100 is retained in the fluid line 5108 by adhesive 5712. The adhesive can be any adhesive, but in one embodiment, the adhesive is a UV curing adhesive. In alternate embodiments, the adhesive may be any adhesive that is compatible with the subject media. In this embodiment, the thermal well 5100 is shown without a zone 5406.

Figure 7L:
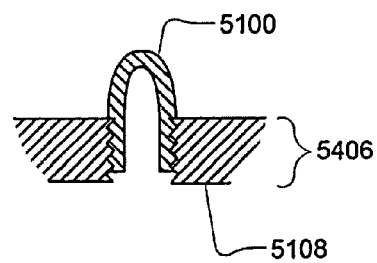

Referring now to FIG. 7L, thermal well 5100 is shown ultrasonically welded in the fluid line 5108. The zone 5406 is fabricated to enable joining by ultrasonic welding.

Figure 7M:
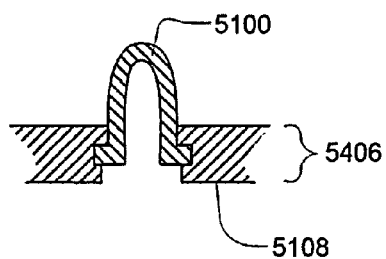

Referring now to FIG. 7M, a thermal well 5100 is shown insert molded in the fluid line 5108. Zone 5406 is a flange for the plastic in the fluid line 5108 to flow around. In the embodiment shown, the flange is flat, however, in other embodiments; the flange may be bell shaped or otherwise.

Figure 7N:
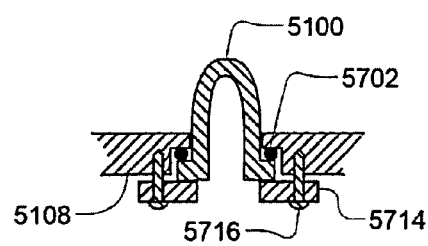

Referring now to FIG. 7N, the thermal well 5100 is shown retained in the fluid line 5108 by a retaining plate 5714 and a fastener 5716. O-ring 5702 is also shown.

Figure 7O:
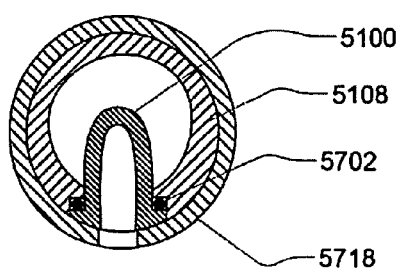
Figure 7P:
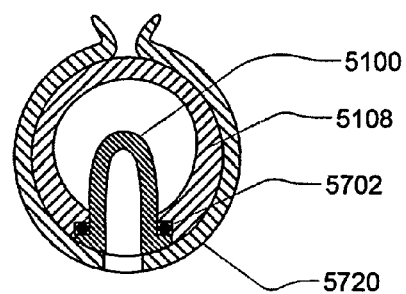

Referring now to FIGS. 7O-7P, an end view is shown of a thermal well 5100 that is retained in a fluid line 5108 by a retaining ring 5718 (FIG. 7O) or in an alternate embodiment, a clip 5720 (FIG. 7P). O-ring 5702 is also shown.

Figure 7Q:
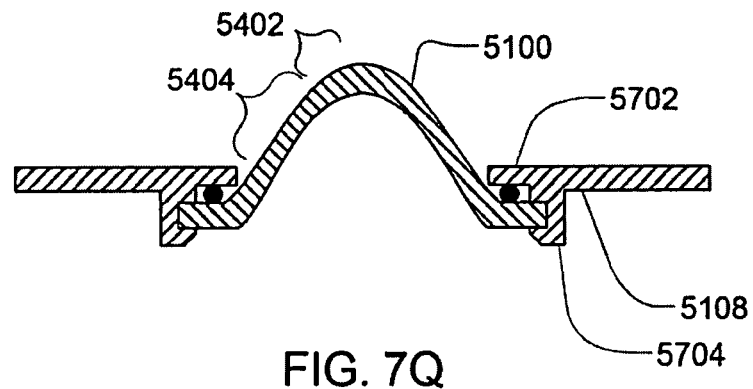

Referring now to FIG. 7Q, the embodiment of FIG. 7C is shown with an alternate embodiment of the thermal well 5100. In this embodiment of the thermal well 5100 the referred to as zone 5404 in FIG. 4 includes a taper that may allow for easier alignment with a sensing probe, better isolation of zone 5402 from the ambient and better flow characteristics in the fluid path. The thermal well 5100 is shown retained in the fluid line 5108 using flexible tabs 5704. An O-ring is also provided.

Figure 7R:
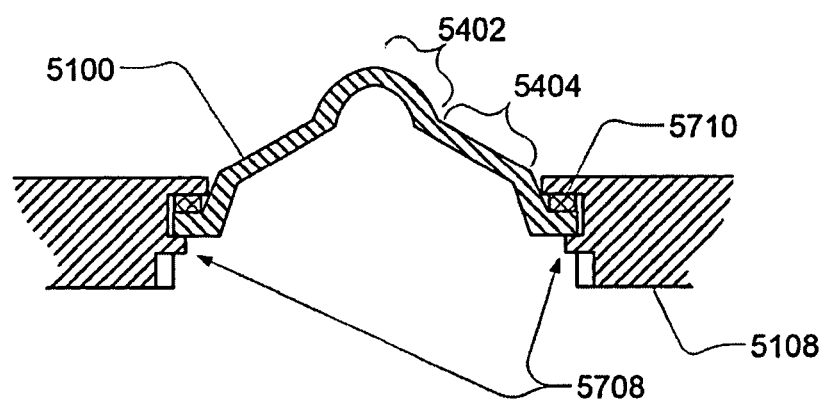
Figure 7S:
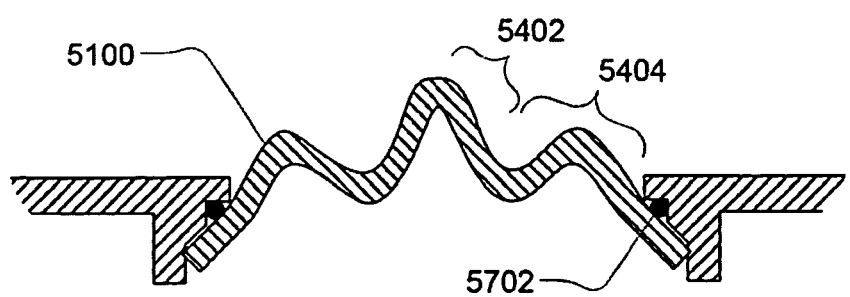

FIG. 7R shows the embodiment of FIG. 7J with an alternate embodiment of the thermal well 5100. The thermal well 5100 shown in this embodiment has a taper in zone 5404 that may allow for easier alignment with a sensing probe, may allow better isolation of zone 5402 from the ambient and may allow better flow characteristics in the fluid path. Zone 5402 provides a hemispherical contact for effective thermal coupling with a thermal probe. The thermal well 5100 is heat staked 5708 to retain the thermal well 5100 in the fluid line 5108. In some embodiments of FIG. 7R, an O-ring 5710 is also included. In this embodiment, the O-ring 5710 has a rectangular cross section. However, in alternate embodiments, the O-ring can have a round or X-shaped cross section.

Referring now to FIG. 7S, the embodiment of FIG. 7H is shown with an alternate embodiment of the thermal well 5100. FIG. 7S is shown with the addition of an O-ring 5702. In this embodiment of the thermal well 5100 zone 5404 (as shown in FIG. 4) has convolutions that may allow better isolation of zone 5402 from the ambient. While several geometries have been shown for zone 5404, many others could be shown to achieve desired performance characteristics.

2. Sensing Probes

Various embodiments of systems, devices, and methods for sensor interface, including direct sensor contact, sensor interface through the use of a thermal well, or otherwise with various disposable and reusable components are described. Such systems, devices, and methods for sensor interface can be used with a wide variety of sensors and in a wide variety of applications. Such systems, devices, and methods for sensor interface are by no means limited to use with the various sensor embodiments or for use in any particular context.

Figure 8:
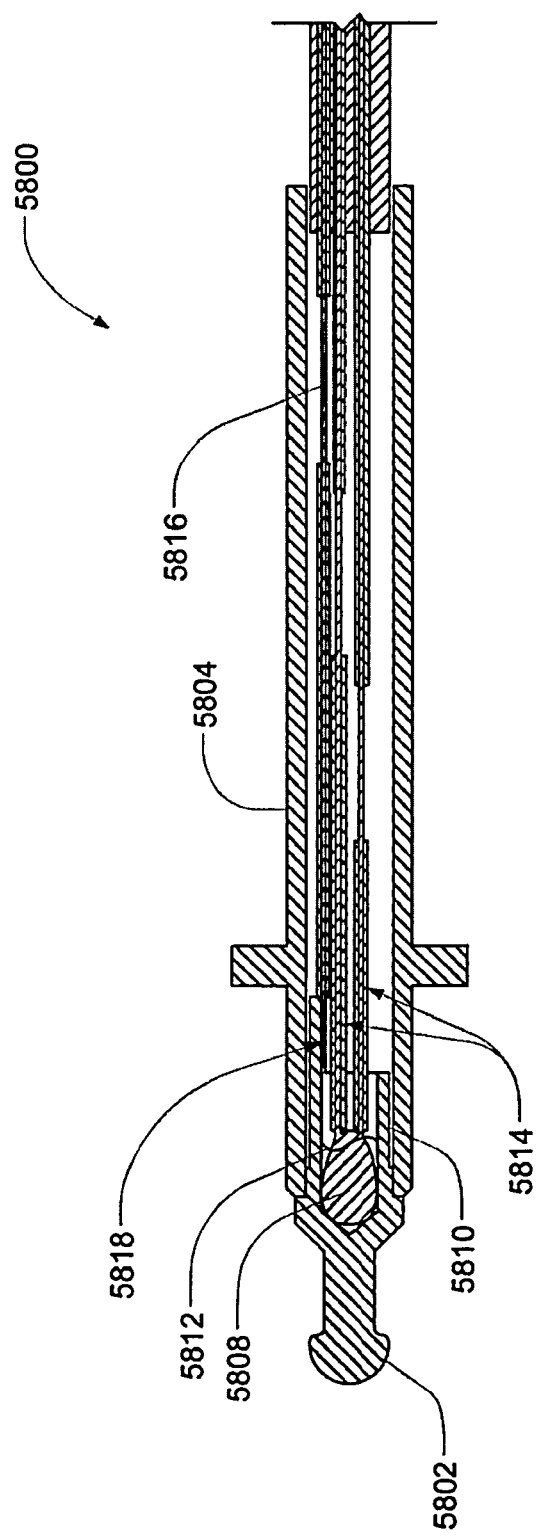
FIG. 8 is a section side view of one embodiment of the sensing probe.

Referring now to FIG. 8, a sectional view of an exemplary embodiment of a sensing probe 5800 is shown. The housing 5804 is a hollow structure that attaches to the tip 5802. The tip is made of a highly thermally conductive material. The housing 5804, in the exemplary embodiment, is made from a thermally insulative material. In some embodiments, the housing is made of a thermally and electrically insulative material. In the exemplary embodiment, the housing 5804 is made of plastic which is a thermally insulative and electrically insulative material. The tip 5802 either contacts the subject media directly, or else is mated with a thermal well.

In the exemplary embodiment, the tip 5802 is attached to the housing 5804 using a urethane resin or another thermal insulator in between (area 5807) the tip 5802 and the housing 5804. Urethane resin additionally adds structural support. In alternate embodiments, other fabrication and joining methods can be used to join the tip 5802 to the housing 5804.

The tip 5802 of the sensing probe 5800 is made of a thermally conductive material. The better thermally conductive materials, for example, copper, silver and steel, can be used, however, depending on the desired use for the sensing probe and the subject media; the materials may be selected to be durable and compatible for the intended use. Additionally, factors such as cost and ease of manufacture may dictate a different material selection. In one exemplary embodiment, the tip 5802 is made from copper. In other embodiments, the material can be an alloy of copper or silver, or either solid or an alloy of any thermally conductive material or element, including but not limited to metals and ceramics. However, in the exemplary embodiments, the tip 5802 is made from metal.

In the exemplary embodiment, the tip 5802 is shaped to couple thermally with a thermal well as described in the exemplary embodiment of the thermal well above. In the exemplary embodiment as well as in other embodiments, the tip 5802 may be shaped to insulate the thermal sensor 5808 from the ambient. In the exemplary embodiment, the tip 5802 is made from metal.

In alternate embodiments a non-electrically conductive material is used for the tip. These embodiments may be preferred for use where it is necessary to electrically insulate the thermal well from the probe. In another alternate embodiment, the tip 5802 may be made from any thermally conductive ceramic.

In the exemplary embodiment, the thermal sensor 5808 is located in the housing and is attached to the interior of the tip 5802 with a thermally conductive epoxy 5812. In the exemplary embodiment, the epoxy used is THERMALBOND, however, in other embodiments; any thermal grade epoxy can be used. However, in alternate embodiments, thermal grease may be used. In alternate embodiments, an epoxy or grease is not used.

The thermal sensor 5808, in the exemplary embodiment, is a thermistor. The thermistor generally is a highly accurate embodiment. However in alternate embodiments, the thermal sensor 5808 can be a thermocouple or any other temperature sensing device. The choice of thermal sensor 5808 may again relate to the intended use of the sensing apparatus.

Figure 9:
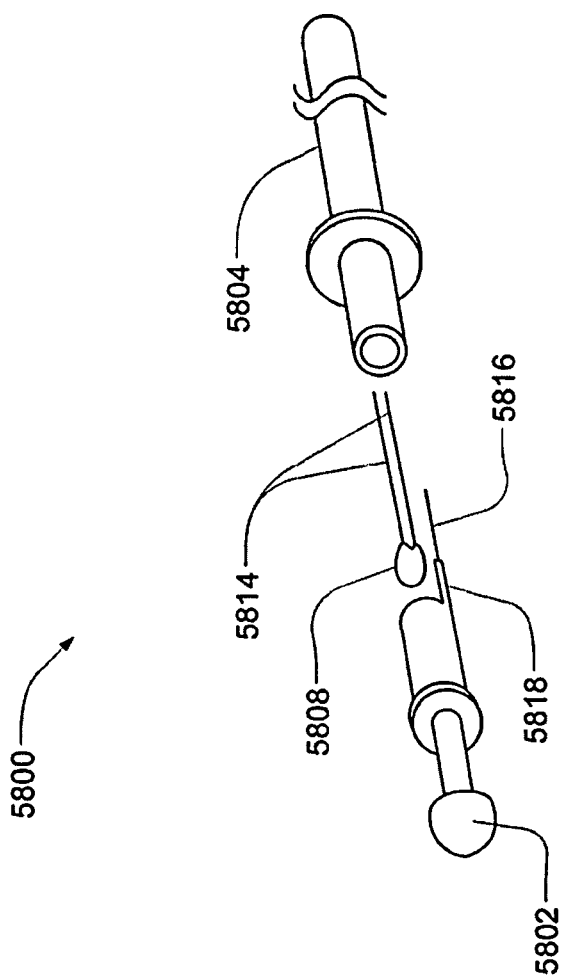
FIG. 9 is an exploded view of the embodiment shown in FIG. 8.

Leads 5814 from the thermal sensor 5808 exit the back of the housing 5804. These leads 5814 attach to other equipment used for calculations. In the exemplary embodiment, a third lead 5816 from the tip 5802 is also included. This third lead 5816 is attached to the tip on a tab 5818. The third lead 5816 is attached to the tip 5802 because in this embodiment, the tip 5802 is metal and the housing is plastic. In alternate embodiments, the housing 5804 is metal, thus the third lead 5816 may be attached to the housing 5804. Thus, the tip 5802, in the exemplary embodiment, includes a tab 5818 for attachment to a lead. However, in alternate embodiments, and perhaps depending on the intended use of the sensing apparatus, the third lead 5816 may not be included. Also, in alternate embodiments where a third lead is not desired, the tip 5802 may not include the tab 5818. Referring now to FIG. 9, an exploded view of the sensing probe 5800 is shown.

Figure 10:
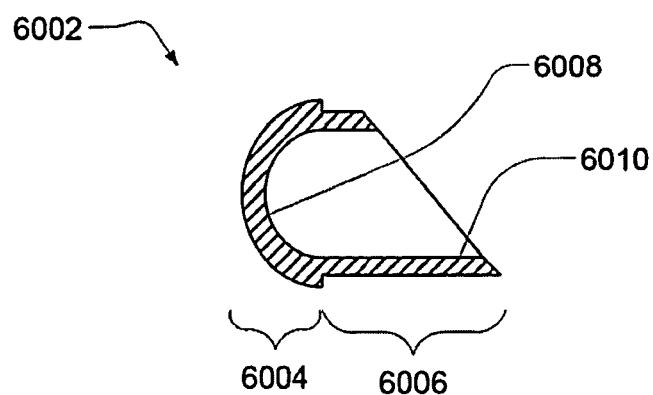
FIG. 10 is a sectional view of an alternate embodiment of the tip of the sensing probe.

Referring now to FIG. 10 an alternate embodiment of the exemplary embodiment is shown. In this embodiment, the tip 6002 of the sensing probe is shown. The tip 6002 includes a zone 6004 that will contact either a subject media to be tested or a thermal well. A zone 6006 attaches to the sensor probe housing (not shown). An interior area 6008 accommodates the thermal sensor (not shown). In this embodiment, the tip 6002 is made from stainless steel. However, in other embodiments, the tip 6002 can be made from any thermally conductive material, including but not limited to: metals (including copper, silver, steel and stainless steel), ceramics or plastics.

Figure 11A:
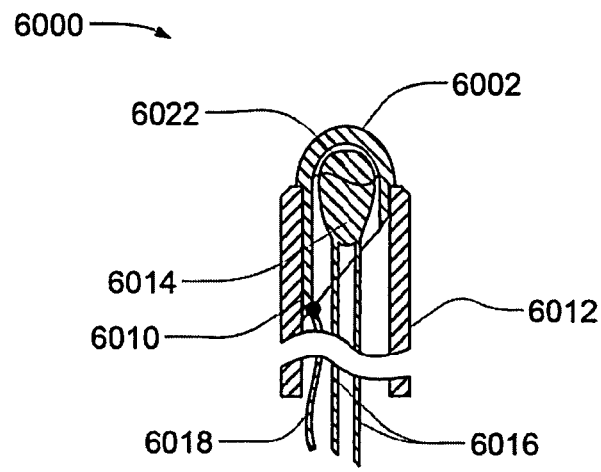
FIG. 11A is an alternate embodiment of the sensing probe.
Figure 11B:
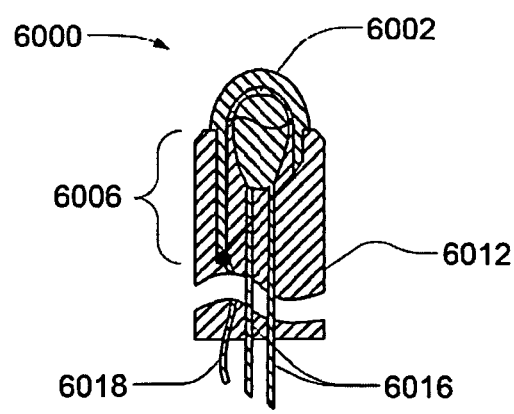
FIG. 11B is an alternate embodiment of the sensing probe.

In the exemplary embodiment, zone 6006 includes a tab 6010. A third lead (as described with respect to FIG. 8, 5816) attaches from the tab 6010. Referring next to FIGS. 11A and 11B, the sensing probe 6000 is shown including the tip 6002 and the housing 6012. In one embodiment, the housing 6012 is made from any thermally insulative material, including but not limited to, plastic. In one embodiment, the housing 6012 is press fit to the tip 6002, glued or attached by any other method. In one embodiment, the thermal sensor 6014 is thermally coupled to the tip 6002 with thermal grade epoxy or, in alternate embodiments, thermal grease 6022. Two leads 6016 from the thermal sensor 6014 extend to the distal end of the housing. In some embodiments, a third lead 6018 is attached to the tip 6002 from the tab 6010. As discussed above, in some embodiments where the third lead is not desired, the tip 6002 does not include a tab 6010.

Referring now to FIG. 11B, an alternate embodiment of the sensing probe 6000 is shown. In this embodiment, the housing 6012 is a plastic molded over zone 6006 of the tip 6002 and the leads 6016, and in some embodiments, a third lead 6018.

Figure 12:
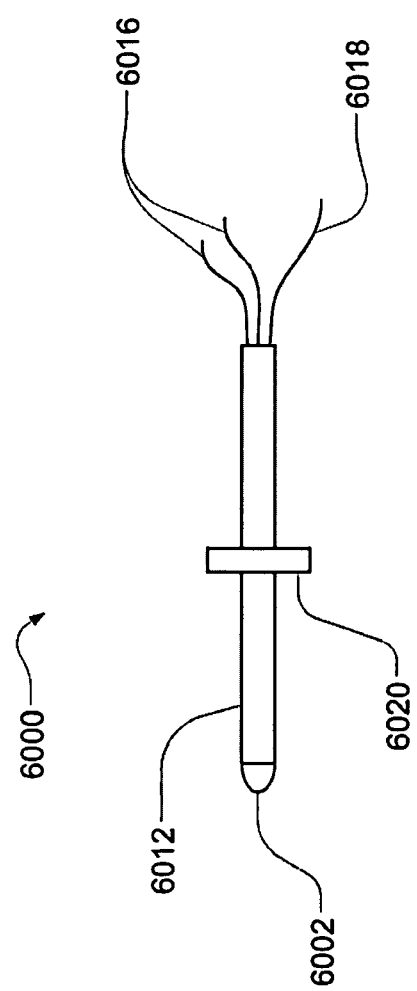
FIG. 12 is a side view of an alternate embodiment of the sensing probe.

Referring now to FIG. 12, a full side view of one embodiment of the sensing probe 6000 shown in FIGS. 10-11B is shown. The sensing probe 6000 includes a housing 6012, a tip 6002 and the leads 6016, 6018. Flange 6020 is shown. In some embodiment, flange 6020 is used to mount and/or attachment to equipment.

Figure 13A:
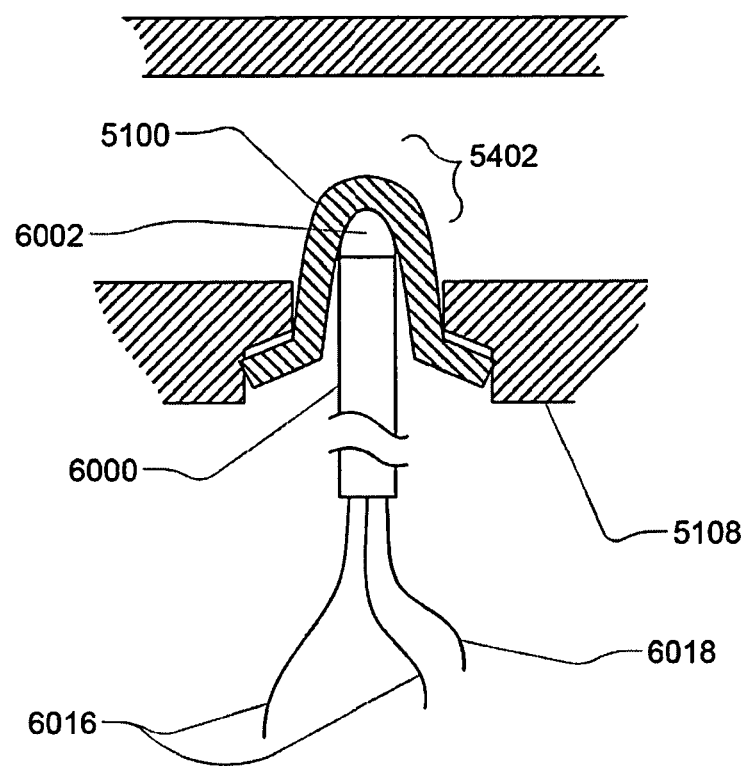
FIG. 13A is a section view of a sensing probe coupled to a thermal well.
Figure 13B:
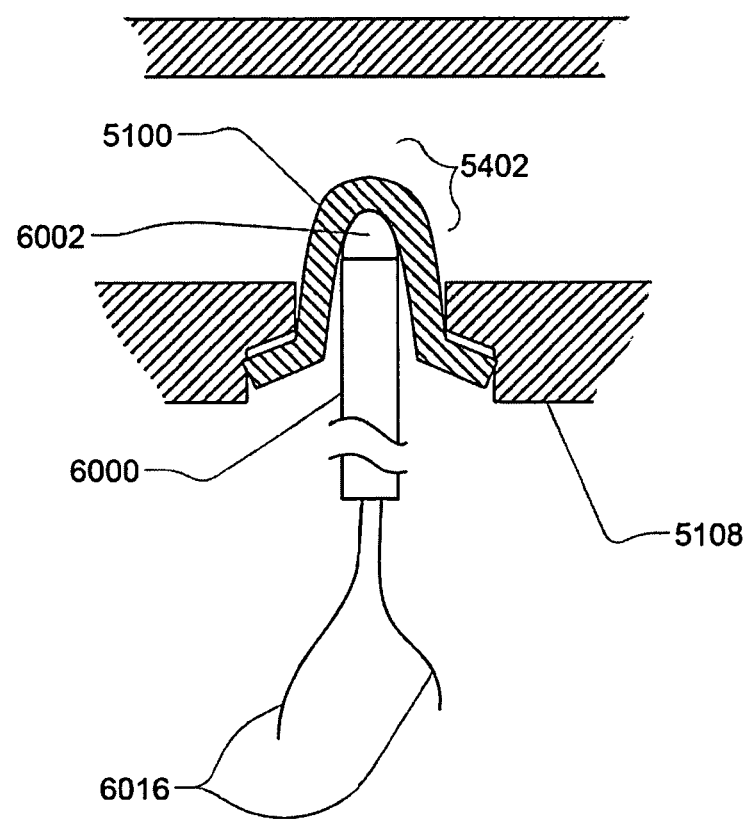
FIG. 13B is an alternate embodiment of the sensing probe shown in FIG. 13A.

Referring now to FIG. 13A, the sensing probe 6000 shown in FIGS. 10-12, is shown coupled to a thermal well 5100 which is fastened into a fluid line 5108. In the embodiment as shown, two leads 6016 are shown at the distal end of the sensing probe 6000. And, in some embodiments, a third lead 6018 is also incorporated into the sensing probe 6000. FIG. 13B shows an alternate embodiment where the sensing probe 6000 includes two leads 6016 but does not include the third lead 6018.

Referring now to both FIGS. 13A and 13B, the tip 6002 of the sensing probe 6000 is in direct contact with the thermal well 5100. Referring back to FIG. 4 and still referring to FIGS. 13A and 13B the thermal well 5100 includes a zone 5402. The thermal well 5100 is hollow, and the inner part of zone 5402 is formed such that it will be in mating contact with the sensing probe tip 6002. As shown in this embodiment, the thermal well 5100 is designed to have a mating geometry with the sensing probe 6000. Thus, the geometry of the thermal well 5100 may depend on the geometry of the tip 6002 of the sensing probe 6000 and vice-versa. In some embodiments, it may be desirable that the sensing probe 6000 does not have a tight fit or a perfect mate with the thermal well 5100.

Figure 14A:
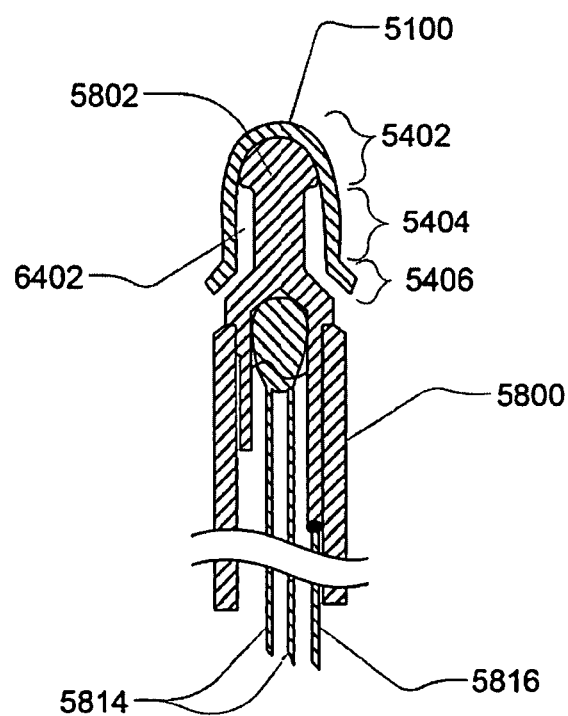
FIG. 14A is a section view of a sensing probe as shown in FIG. 8 coupled to a thermal well.
Figure 14B:
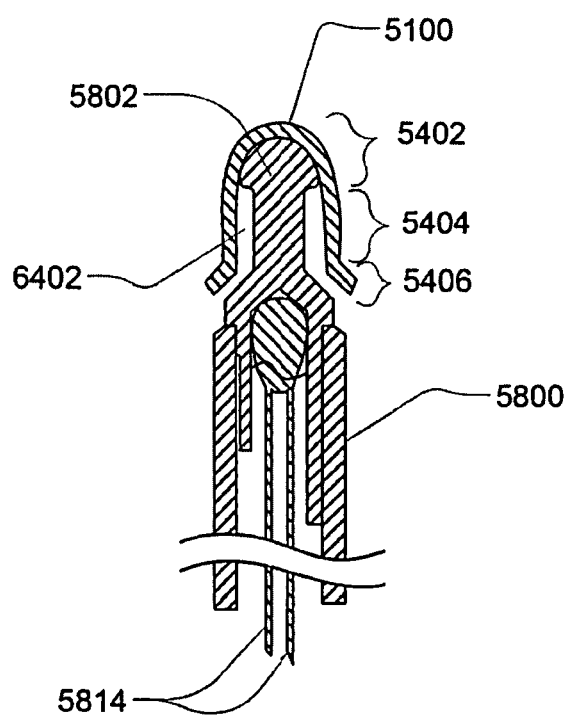
FIG. 14B is an alternate embodiment of the sensing probe shown in FIG. 14A.

Referring now to FIG. 14A, one embodiment of the sensing probe 5800 (as shown in FIG. 8) is shown coupled to a thermal well 5100 which is fastened into a fluid line 5108. In the embodiment as shown, two leads 5814 are shown at the distal end of the sensing probe 5800. In some embodiments, a third lead 5816 is also incorporated into the sensing probe 5800. FIG. 14B shows an alternate embodiment where the sensing probe 5800 includes two leads 5814 but does not include the third lead 5816.

Referring now to both FIGS. 14A and 14B, the tip 5802 of the sensing probe 5800 is in direct contact with the thermal well 5100. Referring back to FIG. 4 and still referring to FIGS. 14A and 14B, the thermal well 5100 includes a zone 5402. The thermal well 5100 is hollow, and the inner part of zone 5402 is formed such that it will be in mating contact with the sensing probe tip 5802. As shown in this embodiment, the thermal well 5100 is designed to have a mating geometry with the sensing probe 5800. Thus, the geometry of the thermal well 5100 depends on the geometry of the tip 5802 of the sensing probe 5800 and vice-versa.

Figure 15:
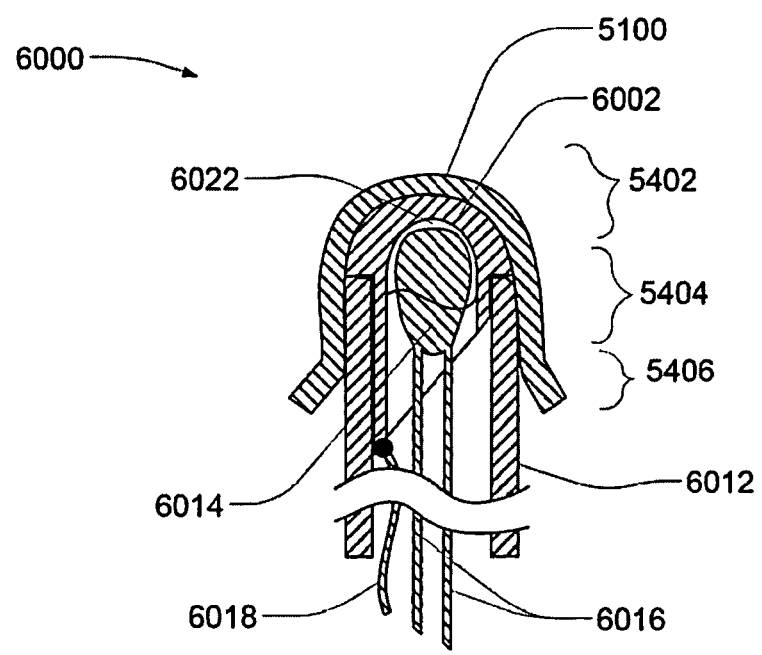
FIG. 15 is a sectional view of one exemplary embodiment of the sensor apparatus.

3. Sensor Apparatus and Sensor Apparatus Systems 3.1. Sensor Apparatus and Sensor Apparatus Systems Utilized in Connection with a Fluid Line For purposes of description of the sensor apparatus, the sensor apparatus is described with respect to exemplary embodiments. The exemplary embodiments are shown in FIGS. 13A, 13B, and FIG. 15, with alternate exemplary embodiments in 14A and 14B. In alternate embodiments of the sensor apparatus, the sensing probe can be used outside of the thermal well. However, the sensor apparatus has already been described herein alone. Thus, the description that follows describes one embodiment of the exemplary embodiment of the sensor apparatus which includes, for this purpose, a sensing probe and a thermal well.

Referring now to FIG. 15, in an exemplary embodiment, the sensing probe 6000 shown in FIG. 13A and the thermal well 5100 are shown coupled and outside of a fluid line. As described above, the thermal well 5100 can be in a fluid line, a protective sleeve, any disposable, machine, chamber, cassette or container. However, for purposes of this description of the exemplary embodiment, the thermal well 5100 is taken to be anywhere where it is used to determine thermal and/or conductive properties (FIG. 13A) of a subject media.

A subject media is in contact with the outside of zone 5402 of the thermal well 5100. Thermal energy is transferred from the subject media to the thermal well 5100 and further transferred to the tip 6002 of the sensing probe 6000. Thermal energy is then conducted to the thermal sensor 6014. The thermal sensor 6014 communicates via leads 6016 with equipment that can determine the temperature of the subject media based on feedback of the thermal sensor 6014. In embodiments where conductivity sensing is also desired, lead 6018 communicates with equipment that can determine the conductivity of the subject media. With respect to determining the conductivity of the subject media, in addition to the lead 6018, a second electrical lead/contact (not shown) would also be used. The second lead could be a second sensor apparatus as shown in FIG. 15, or, alternatively, a second probe that is not necessarily the same as the sensor apparatus shown in FIG. 15, but rather, any probe or apparatus capable of sensing capacitance of the subject media, including, an electrical contact.

Heat transfer from the tip 6002 to the thermal sensor 6014 may be improved by the use of a thermal epoxy or thermal grease 6022.

Referring now to FIGS. 14A and 14B, in the alternate exemplary embodiment, whilst the sensing probe 5800 is coupled to the thermal well 5100, the tip 5802, having the geometry shown, forms an air gap 6402 between the inner zones 5404 and 5406 of the thermal well 5100 and the tip 5802. The air gap 6402 provides an insulative barrier so that only the top of the sensing tip of 5802 is in communication with the top zone 5402 of the thermal well 5100.

The sensing probe 5800 and thermal well 5100 are shown coupled and outside of a fluid line. As described above, the thermal well 5100 can be in a fluid line, a protective sleeve, disposable unit, machine, non-disposable unit, chamber, cassette or container. However, for purposes of this description of the exemplary embodiment, the thermal well 5100 is taken to be anywhere where it is used to determine thermal and/or conductive properties (FIG. 14A) of a subject media.

A subject media is in contact with the outside of zone 5402 of the thermal well 5100. Thermal energy is transferred from the subject media to the thermal well 5100 and further transferred to the tip 5802 of the sensing probe 5800. Thermal energy is then conducted to the thermal sensor 5808. The thermal sensor 5808 communicates via leads 5814 with equipment that can determine the temperature of the subject media based on feedback of the thermal sensor 5808. In embodiments where conductivity sensing is also desired, lead 5816 communicates with equipment that can determine the conductivity of the subject media. With respect to determining the conductivity of the subject media, in addition to the lead 5816, a second electrical lead (not shown) would also be used. The second lead could be a second sensor apparatus as shown in FIG. 14A, or, alternatively, a second probe that is not necessarily the same as the sensor apparatus shown in FIG. 14A, but rather, any probe or apparatus capable of sensing capacitance of the subject media, including, an electrical contact.

Heat transfer from the tip 5802 to the thermal sensor 5808 can be improved by the use of a thermal epoxy or thermal grease 5812.

Figure 16:
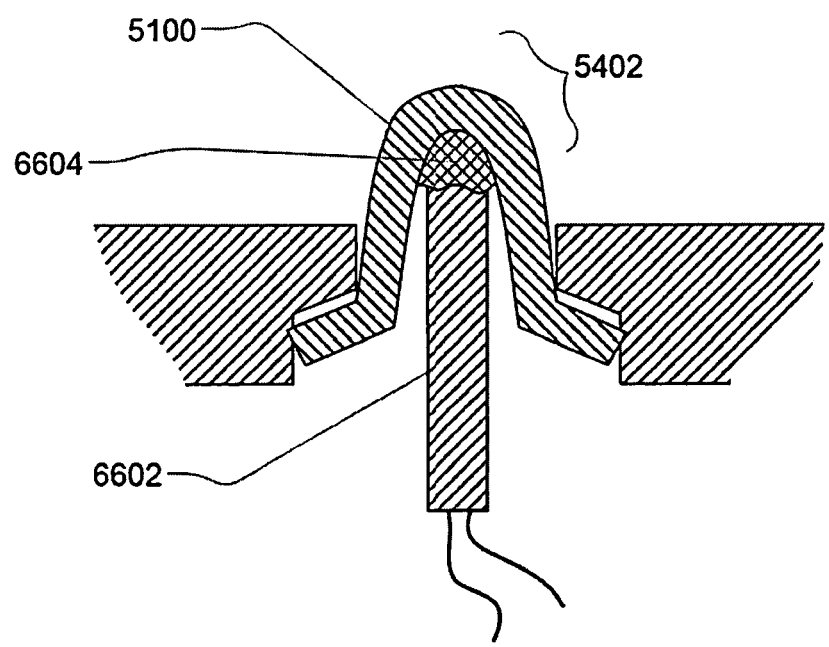
FIG. 16 shows an alternate embodiment of a sensing probe coupled to a thermal well.

Referring now to FIG. 16, an alternate embodiment showing a sensing probe 6602 coupled to a thermal well 5100 is shown. For purposes of this description, any embodiment of the sensing probe 6602 and any embodiment of the thermal well 5100 can be used. In this embodiment, to increase the thermal coupling between the tip of the sensing probe 6602 and the thermal well 5100, thermal grease 6604 is present at the interface of the tip of the sensing probe 6602 and the inner zone 5402 of the thermal well 5100. In one embodiment, the amount of thermal grease 6604 is a volume sufficient to only be present in zone 5402. However, in alternate embodiments, larger or smaller volumes of thermal grease can be used.

Figure 17:
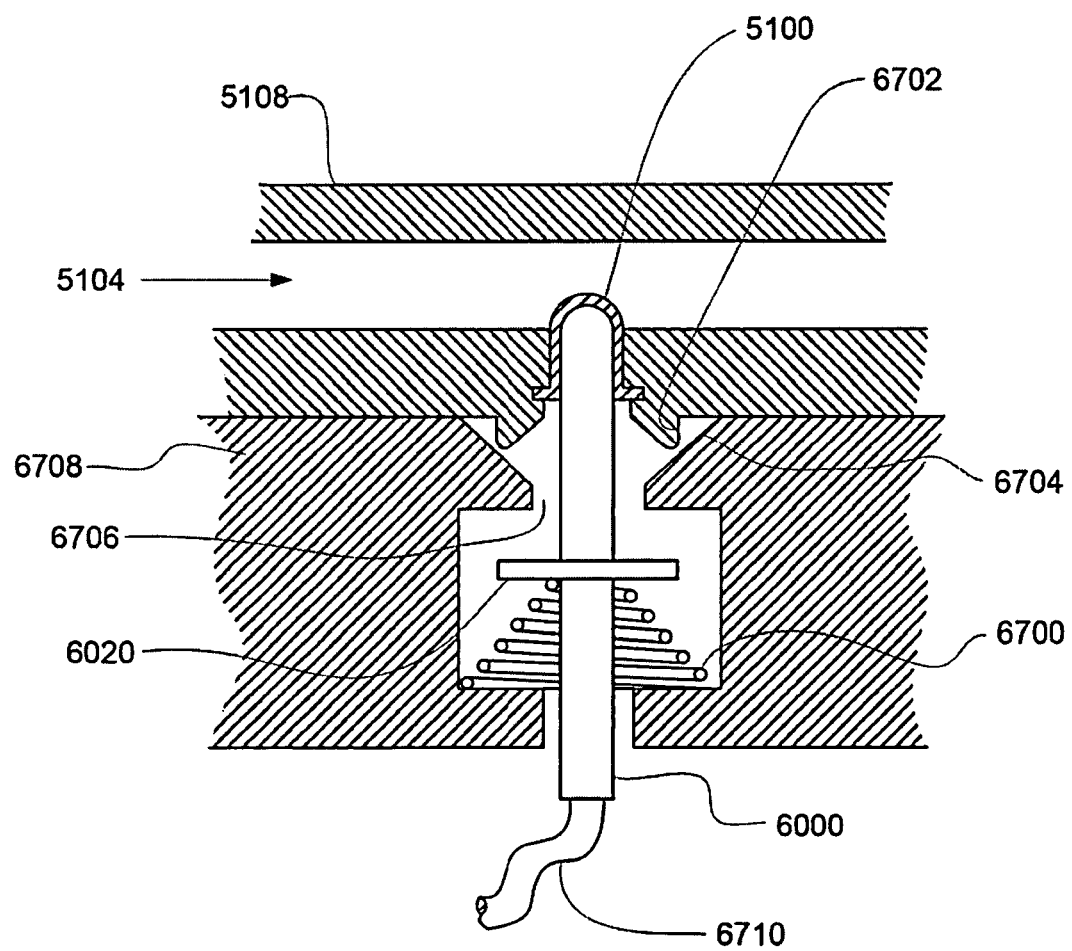
FIG. 17 is a section view of one embodiment of a sensing probe coupled to a thermal well and suspended by a spring.

Referring now to FIG. 17, a sensor apparatus system is shown. In the system, the sensor apparatus is shown in a device containing a fluid line 5108. The sensor apparatus includes the sensing probe 6000 and the thermal well 5100. In this embodiment, the thermal well 5100 and fluid line 5108 is a disposable portion and the sensing probe 6000 is a reusable portion. Also in the reusable portion is a spring 6700. The spring 6700 and sensing probe 6000 are located in a housing 6708. The housing 6708 can be in any machine, container, device or otherwise. The spring 6700 can be a conical, a coil spring, wave spring, or urethane spring.

In this embodiment, the thermal well 5100 and the sensing probe 6000 may include alignment features 6702, 6704 that aid in the thermal well 5100 and sensing probe 6000 being aligned. The correct orientation of the thermal well 5100 and the sensing probe 6000 may aid in the mating of the thermal well 5100 and the sensing probe 6000 to occur. The configuration of the space 6706 provides the sensing probe 6000 with space for lateral movement. This allows the sensing probe 6000 to, if necessary; move laterally in order to align with the thermal well 5100 for mating.

The sensing probe 6000 is suspended by a spring 6700 supported by the flange 6020. The spring 6700 allow vertical movement of the sensing probe 6000 when the thermal well 5100 mates with the sensing probe 6000. The spring 6700 aids in establishing full contact of the sensing probe 6000 and the thermal well 5100.

The fluid line 5108 can be in any machine, container, device or otherwise. The fluid line 5108 contains a fluid path 5104. A subject media flows through the fluid path 5104 and the thermal well 5100, located in the fluid line 5108 such that the thermal well 5100 has ample contact with the fluid path 5104 and can sense the temperature properties and, in some embodiments, the conductive properties of the subject media. The location of the thermal well 5100 in the fluid path 5104, as described in more detail above, may be related to the desired accuracy, the subject media and other considerations.

The spring 6700 and sensing probe 6000 assembly, together with the space 6706 in the housing 6708 may aid in alignment for the mating of the sensing probe 6000 and the thermal well 5100. The mating provides the thermal contact so that the thermal well 5100 and the sensing probe 6000 are thermally coupled.

A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 18:
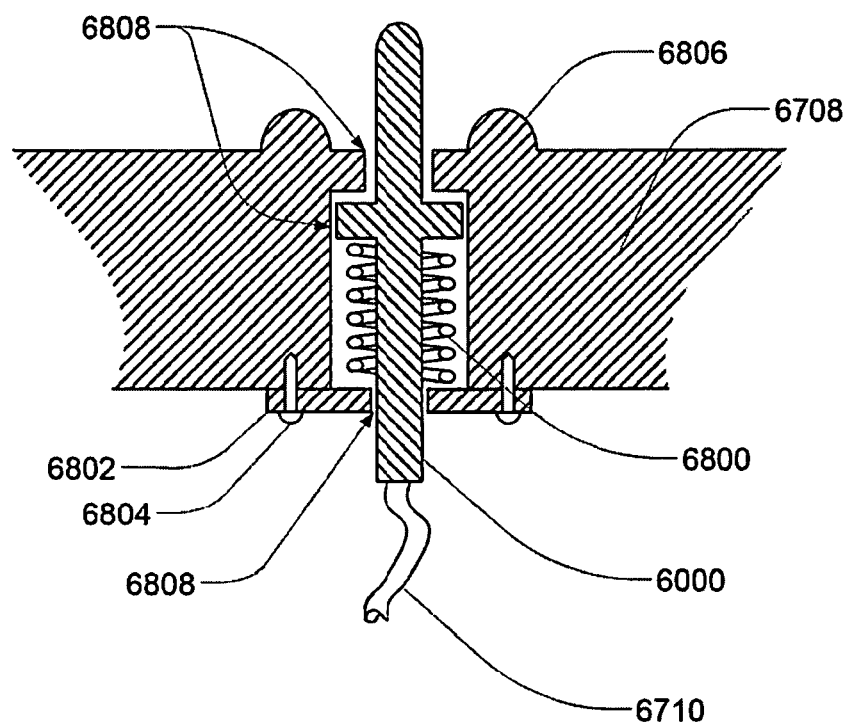
FIG. 18 is a section view of one embodiment of a sensing probe in a housing.

Referring now to FIG. 18, an alternate embodiment of the system shown in FIG. 17 is shown. In this embodiment, the sensing probe 6000 is suspended by a coil spring 6800. A retaining plate 6802 captures the coil spring 6800 to retain the spring 6800 and sensing probe 6000. In one embodiment, the retaining plate 6802 is attached to the housing 6708 using screws. However, in alternate embodiments, the retaining plate 6802 is attached to the housing 6708 using any fastening method including but not limited to: adhesive, flexible tabs, press fit, and ultrasonic welding. Aligning features 6806 on the housing 6708 aid in alignment of the sensing probe 6000 to a thermal well (not shown). Lateral movement of the sensing probe 6000 is provided for by clearance in areas 6808 in the housing 6708. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 19:
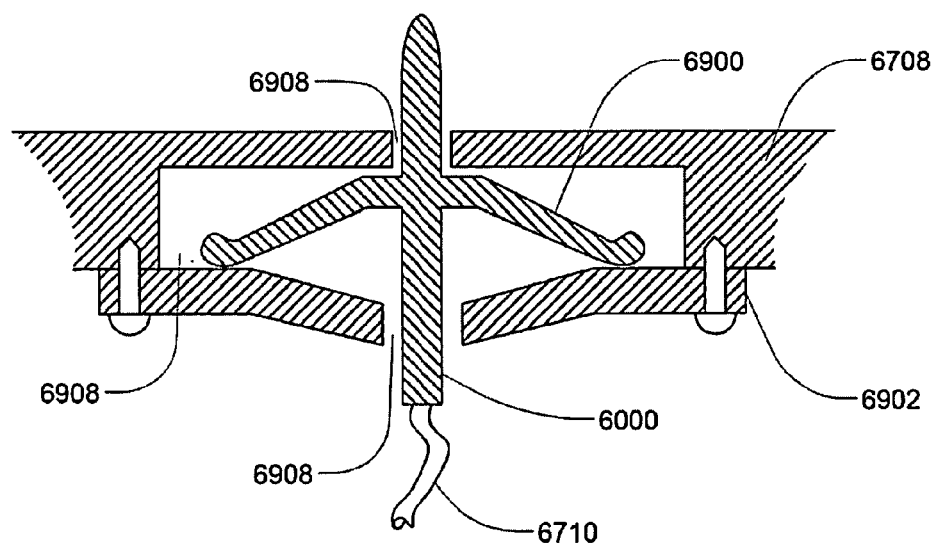
FIG. 19 is a section view of one embodiment of a sensing probe in a housing.

Referring now to FIG. 19, a sensing probe 6000 is shown in a housing 6708. In these embodiments, an alternate embodiment of a spring, a flexible member 6900, is integrated with the sensing probe 6000 to allow vertical movement of the sensing probe 6000 within the housing 6708. A retaining plate 6902 captures the flexible member 6900 to retain the flexible member 6900 and sensing probe 6000. In one embodiment, the retaining plate 6902 is attached to the housing 6708 using screws. However, in alternate embodiments, the retaining plate 6902 is attached to the housing 6708 using any fastening method including but not limited to: adhesive, flexible tabs, press fit, and ultrasonic welding.

Lateral movement of the sensing probe 6000 is provided for by clearance in areas 6908 in the housing 6708. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

Figure 20:
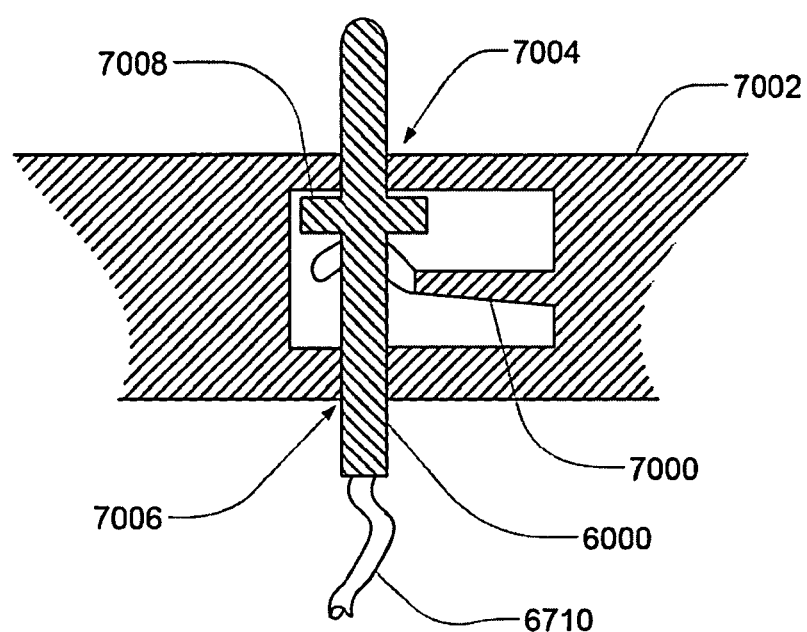
FIG. 20 is a section view of one embodiment of a sensing probe in a housing.

Referring now to FIG. 20, an alternate embodiment of a sensing probe 6000 in a housing 7002 is shown. In this embodiment, flexible member 7000 is attached or part of the housing 7002, provides for vertical movement of the sensing probe 6000. In this embodiment, the openings 7004, 7006 in housing 7002 are sized such that the sensing probe 6000 experiences limited lateral movement. Flexible member 7000 acts on the flange 7008 on the sensing probe 6000. A wire 6710 is shown. The wire contains the leads. In some embodiments, there are two leads. Some of these embodiments are temperature sensing. In other embodiments, the wire contains three or more leads. Some of these embodiments are for temperature and conductivity sensing.

The flange, as shown and described with respect to FIGS. 12, 17, 20, can be located in any area desired on the sensing probe 6000. In other embodiments, the sensing probe may be aligned and positioned by other housing configurations. Thus, the embodiments of the housing shown herein are only some embodiments of housings in which the sensor apparatus can be used. The sensor apparatus generally depends on being located amply with respect to the subject media. The configurations that accomplish this can vary depending on the subject media and the intended use of the sensing apparatus. Further, in some embodiments where the thermal well is not used, but rather, the sensing probe is used only. The housing configurations may vary as well.

The sensing apparatus, in some embodiments, is used to sense conductivity. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Figure 21:
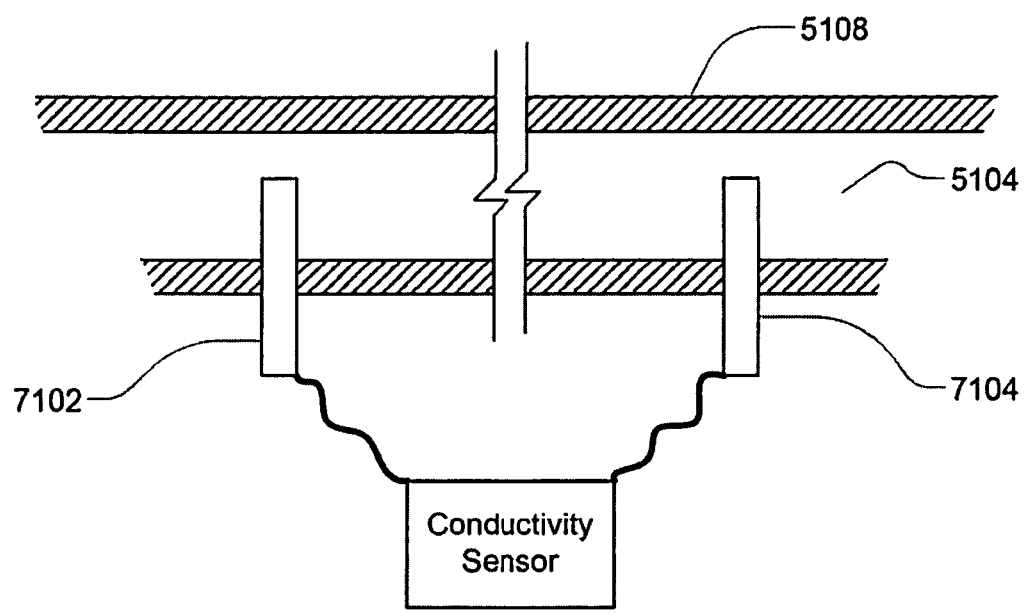
FIG. 21 is a side view of a fluid line including two sensors.

Referring now to FIG. 21, for conductivity sensing, at least two sensors 7102, 7104 are located in an area containing the subject media. In the embodiment shown, the area containing the subject media is a fluid path 5104 inside a fluid line 5108. The conductivity sensors 7102, 7104 can be one of the various embodiments of sensing probes as described above, or one of the embodiments of the sensor apparatus embodiments (including the thermal well) as described above. However, in other embodiments, only one of the sensors is one of the embodiments of the sensor apparatus or one of the embodiments of the sensing probe, and the second sensor is any electrical sensor known in the art. Thus, in the systems described herein, conductivity and temperature can be sensed through using either one of the sensor apparatus or one of the sensor probes as described herein and a second capacitance sensor, or one of the sensor apparatus or one of the sensor probes as described herein and an electrical sensor.

Figure 22:
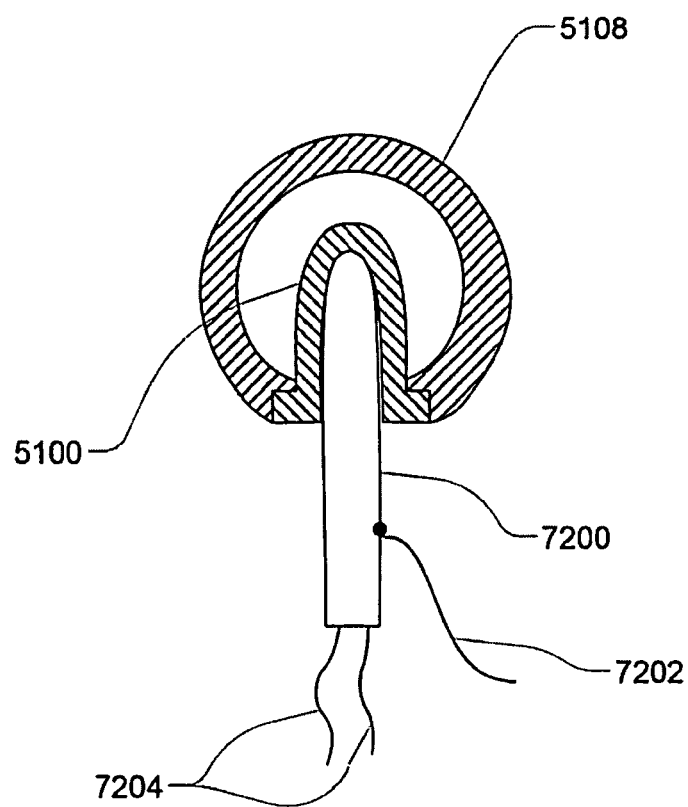
FIG. 22 is a section view of a fluid line with a sensor apparatus.

Referring now to FIG. 22, an alternate embodiment of a sensor apparatus including a sensing probe 7200 and a thermal well 5100 is shown in a fluid line 5108. In this embodiment, the sensing probe 7200 is constructed of a metal housing. The thermal well 5100 is also constructed of metal. The thermal well 5100 and the sensing probe 7200 can be made from the same metal or a different metal. The metal, in the preferred embodiment, is a conductive metal, which may include stainless steel, steel, copper and silver. A lead 7202 is attached to the sensing probe 7200 housing for conductivity sensing. The thermal sensing leads 7204 are attached to a thermal sensor located inside the sensing probe 7200 housing. In this embodiment, therefore, the third lead 7202 (or the lead for conductivity sensing) can be attached anywhere on the sensing probe 7200 because the sensing probe 7200 is constructed of metal. In the previously described embodiments, where the sensing probe housing was constructed of plastic, and the sensing tip constructed of metal, the third lead for conductivity sensing was attached to the sensing tip.

A known volume of subject media may be used to determine conductivity. Thus, two sensors may be used and the volume of fluid between the two sensors can be determined. Conductivity sensing is done with the two electrical contacts (as described above), where one or both can be the sensor apparatus. The volume of subject media between the two contacts is known.

Conductivity sensing is done by determining the conductivity from each of the sensors and then determining the difference. If the difference is above a predetermined threshold, indicating an abnormal difference in conductivity between the first and second sensor (the designations "first" and "second" being arbitrary), then it can be inferred that air may be trapped in the subject media and a bubble detection alarm may be generated to indicate a bubble. Thus, if there is a large decrease in conductivity (and likewise, a large increase in resistance) between the first and second sensor, air could be trapped and bubble presence may be detected.

Leaks in a machine, system, device or container may be determined using the conductivity sensing. Where a sensing apparatus is in a machine, device or system, and that sensing apparatus senses conductivity, in one embodiment, a lead from the sensor apparatus (or electrical contacts) to an analyzer or computer machine may be present.

In some embodiments, the analyzer that analyzes the electrical signals between the contacts is connected to the metal of the machine, device, system or container. If the analyzer senses an electrical signal from the machine, then a fluid leak may be inferred.

3.2. Sensor Apparatus and Sensor Apparatus Systems Utilized in Connection with a Fluid Cassette The cassette embodiments shown and described in this description include exemplary and some alternate embodiments. However, any variety of cassettes are contemplated that include similar or additional functionality. As well, the cassettes may have varying fluid paths and/or valve placement and may utilize pumping functions, valving functions, and/or other cassette functions. All of these embodiments are within the scope of the invention.

3.2.1. Flexible Membrane Fluid Cassette

Fluid cassettes, including flexible membrane fluid cassettes of the types described in U.S. Pat. No. 5,350,357 issued Sep. 27, 1994 and entitled Peritoneal Dialysis Systems And Methods Employing A Liquid Distribution And Pumping Cassette That Emulates Gravity Flow; U.S. Pat. No. 5,755,683 issued May 26, 1998 and entitled Cassette For Intravenous-Line Flow-Control System; U.S. Pat. No. 6,223,130 issued Apr. 24, 2001 entitled Apparatus And Method For Detection Of A Leak In A Membrane Of A Fluid Flow Control System; U.S. Pat. No. 6,234,997 issued May 22, 2001 entitled System And Method For Mixing And Delivering Intravenous Drugs; U.S. Pat. No. 6,905,479 issued Jun. 14, 2005 entitled Pumping Cartridge Having An Integrated Filter And Method For Filtering A Fluid With The Cartridge; and U.S. patent application Ser. No. 10/412,658 filed Apr. 10, 2003 entitled System And Method For Delivering A Target Volume Of Fluid; and Ser. No. 10/696,990 filed Oct. 30, 2003 entitled Pump Cassette Bank, all of which are hereby incorporated herein by reference in their entireties, may be used in conjunction with the sensor apparatus and sensor apparatus systems described herein.

Figure 23A:
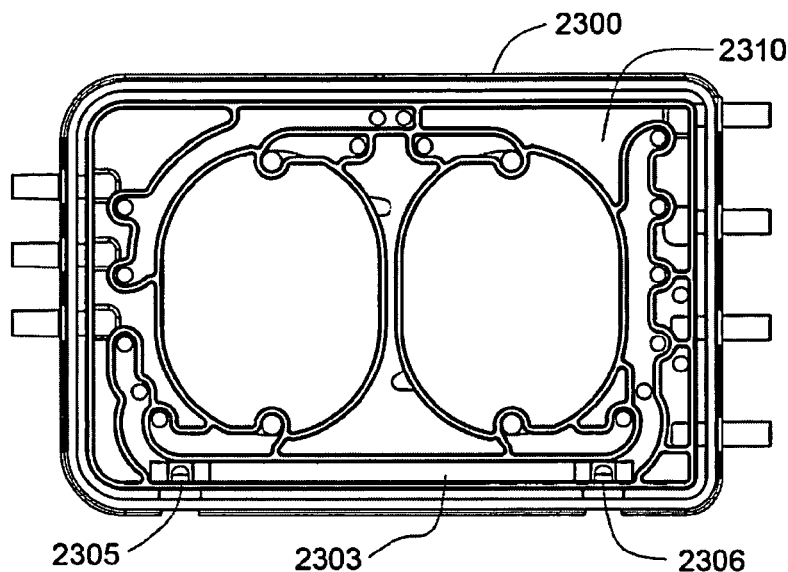
FIG. 23A is a section view of the back side of an exemplary cassette.
Figure 23B:
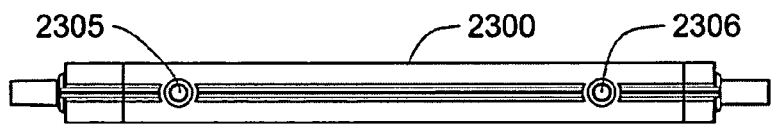
FIG. 23B is a side view of the side of an exemplary cassette.
Figure 23C:
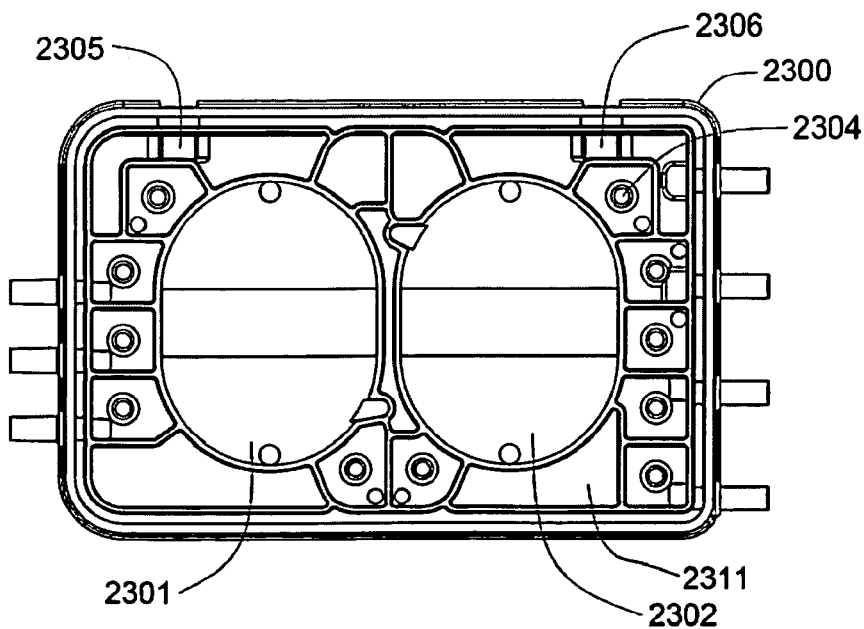
FIG. 23C is a section view of the front of an exemplary cassette.

FIGS. 23A-C show an exemplary embodiment of a flexible membrane cassette of a similar type to those generally disclosed in U.S. Pat. No. 5,350,357 and other of the patents and patent applications referenced above. FIGS. 23A-C shows back, side, and front views of exemplary cassette 2300. As FIGS. 23A-C show, the cassette 2300 includes an injection molded body having back side 2310 shown in FIG. 23A and front side 2311 shown in FIG. 23C. A flexible diaphragm (one of which is shown as 59 in FIG. 24) overlies the front side and back side of cassette 2300.

The cassette 2300 is preferably made of a rigid plastic material and the diaphragms are preferably made of flexible sheets of plastic, although many other materials may be utilized.

Exemplary cassette 2300 forms an array of interior cavities in the shapes of wells and channels. In exemplary cassette 2300, the interior cavities create multiple paths, such as fluid path 2303, to convey liquid (as FIG. 23A shows). In exemplary cassette 2300, the interior cavities also create pump chambers, such as pump chambers 2301 and 2302 (as FIG. 23C shows) and multiple valve stations, such as valve station 2304 (as FIG. 23C shows). In the exemplary cassette 2300, the valve stations, such as valve station 2304, interconnect the multiple liquid paths, such as fluid path 2303, with pump chambers 2301 and 2302 and with each other.

In certain embodiments, exemplary cassette 2300 may be utilized in conjunction with a device (not shown) that locally applies positive and negative pressure, including positive and negative fluid pressure of the type described in U.S. Pat. No. 5,350,357 and other of the patents and patent applications referenced above, on the diaphragm regions overlying the valve stations and pump chambers. While many different types of pump chambers and valves may be utilized with cassette of the types described herein (or, in certain embodiments, not included at all), exemplary pump chambers and valve stations of the type shown in FIGS. 23A-C are described in more detail in U.S. Pat. No. 5,350,357, incorporated herein. The presence, number, and arrangement of the pump chambers, liquid paths, and valve stations can vary. Additionally, alternative or additional cassette functionality may be present in a given cassette.

With further reference to FIGS. 23A-C, exemplary cassette 2300 includes sensor ports 2305 and 2306 that extend into fluid path 2303. Sensor ports 2305 and 2306 may be used to insert a sensing probe, thermal well or other sensing element to allow. Exemplary cassette 2300 shows two sensor ports per cassette, but one port, two ports, or more than two ports may be used depending on the configuration of the cassette and the type of sensor or sensors used.

Again, with reference to FIG. 23A-C, exemplary cassette 2300 is shown with sensor ports 2305 and 2306 position in the rigid body of cassette 2300. In the case of a rigid cassette body with two flexible membranes, one on either side of the rigid body, as shown in FIG. 23A-C, in one embodiment sensor ports 2305 and 2306 may be position in the rigid body portion of the cassette (as shown best in FIG. 23B). However, in other embodiments, the sensor port may extend though one or more areas of the flexible diaphragm overlying the cassette.

Figure 24:
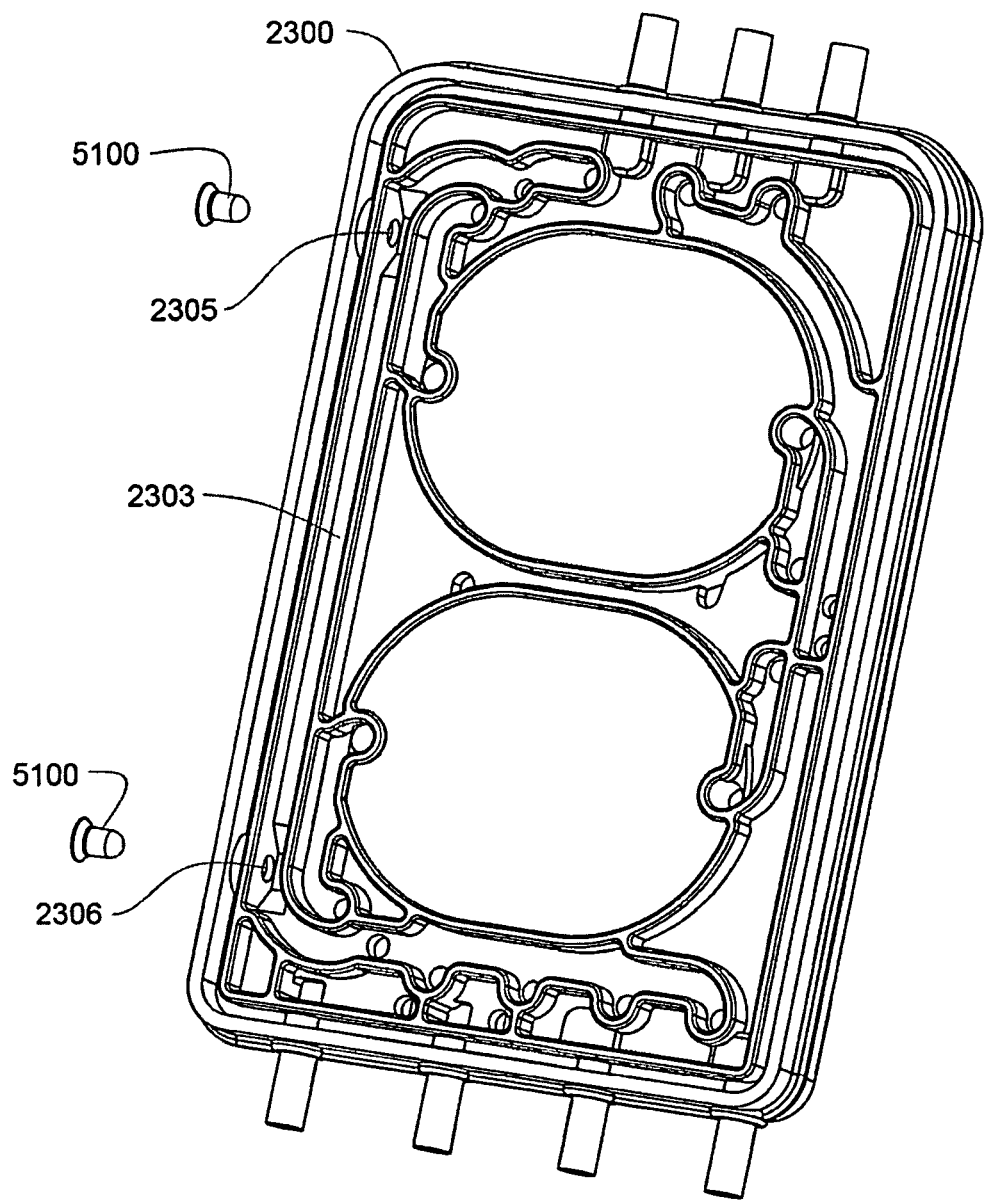
FIG. 24 is a view of an exemplary cassette and thermal wells.

Referring now to FIG. 24, exemplary cassette 2300 is shown with sensor ports 2305 and 2306 extending into fluid path 2303 such that a component placed in sensor ports 2305 and 2306 would come into direct contact with the subject media contained in or flowing through fluid path 2303. FIG. 24 additionally shows thermal wells 5100 positioned near sensor ports 2305 and 2306. In this embodiment, cassette 2300 and thermal wells 5100 are separate parts. In some embodiments, the cassette 2300 and the thermal well 5100 are made from different materials. For these embodiments, the thermal well 5100 can be made from any materials, including but not limited to, plastic, metal, ceramic or a combination thereof. The material may depend in some part on the compatibility with the intended subject media. In other embodiments, thermal well 5100 could be made from the same material as cassette 2300. In yet further embodiments, thermal well 5100 could be formed as a part of the structure of the rigid body of cassette 2300.

The length and width of the thermal well 5100 utilized with exemplary cassette 2300 can be any length and width having the desired or tolerable accuracy characteristics and which properly positions any sensor or sensing probe utilized with thermal well 5100 sufficiently in contact with the subject media contained in or flowing through fluid path 2306. The length of thermal well 5100 may impact the fluid flow of the subject media in fluid path 2303 to a certain extent. It also should be understood that the length of the thermal well 5100 may also impact the turbulence of the fluid flow. Thus, the length and width of the thermal well 5100 may be changed to have greater or lesser impact on the fluid flow and turbulence of the fluid, while mitigating the other variables.

The shape of the thermal well 5100 is also a variable. Any shape desired is contemplated. However, the shape of the thermal well 5100, as with the other variables, is determined in part based on the intended use of the sensor apparatus. For purposes of description, an exemplary embodiment is described herein. However, the shape in the exemplary embodiment is not meant to be limiting. All of the various embodiments of thermal wells described herein may be used in conjunction with cassettes, such as exemplary cassette 2300.

Figure 25:
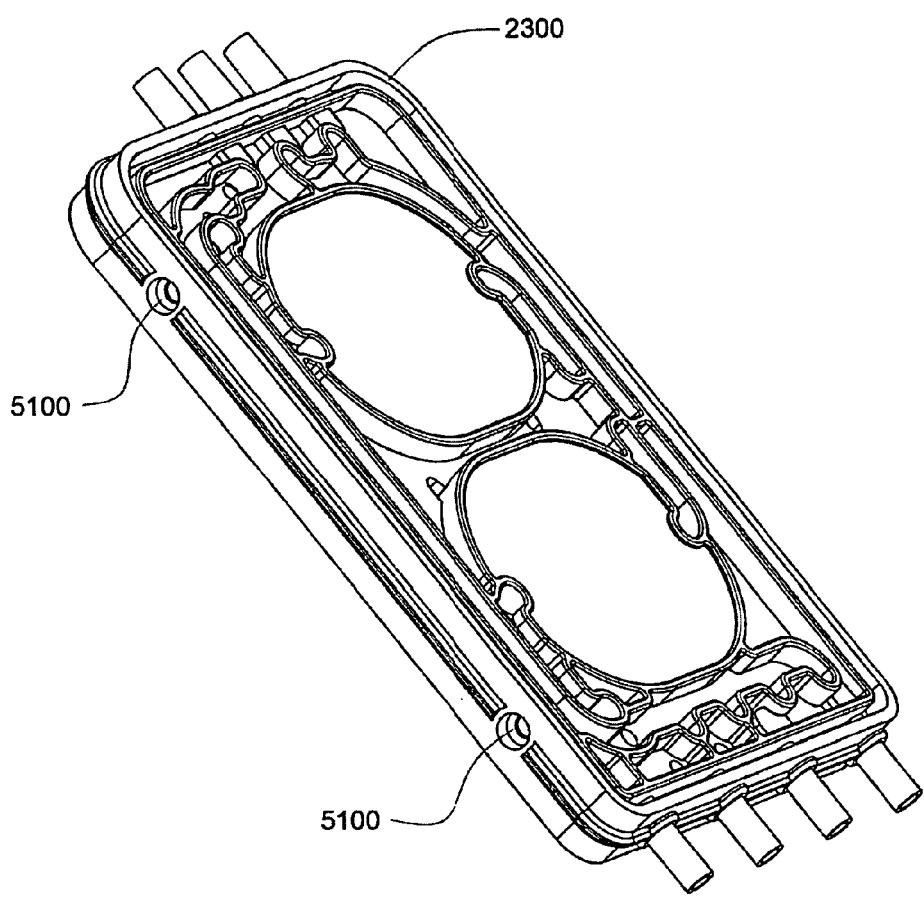
FIG. 25 is a view of an exemplary cassette with thermal wells installed.

FIG. 25 shows thermal wells 5100 installed in exemplary cassette 2300. Thermal well 5100 may be installed in exemplary cassette 2300 by use of the ways described herein, including adhesive, welding (ultrasonic and otherwise), o-ring, retaining plate, and otherwise. The thermal well 5100 used in connection with a cassette may be of various shapes and configurations. However, referring now to FIG. 4 for purposes of description, the embodiment of a thermal well 5100 shown may be utilized in conjunction with a cassette. In the exemplary embodiment shown in FIG. 4, the bottom zone 5406 is shaped to aid in press fitting the thermal well into the sensor port 2305 shown in FIGS. 23A-C and 24.

Figure 26:
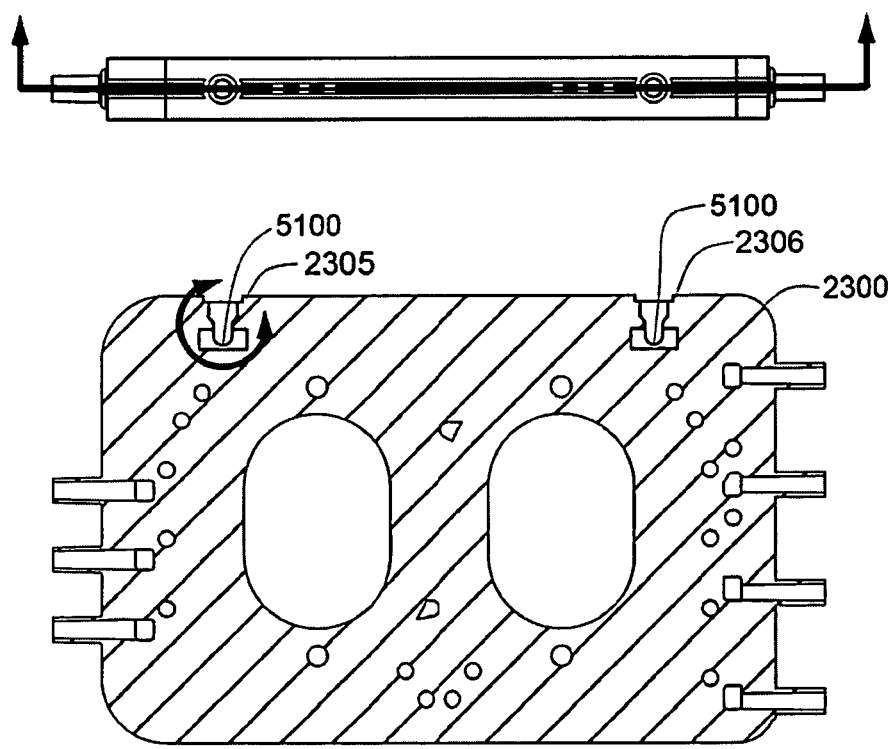
FIG. 26 is a view of the thermal wells extending into a fluid line of an exemplar cassette.

FIG. 26 further shows thermal well 5100 installed in sensor port 2305 and 2306. As may be best shown by FIG. 27, thermal well 5100 extends into fluid path 2303 so that thermal well 5100 may come into direct contact with any subject media contained in or flowing through exemplary cassette 2300.

In certain embodiments of sensor apparatus and sensor apparatus systems used in conjunction with a flexible membrane cassette, a sensing probe may be installed directly into sensing ports 2305 and 2306 (sensing ports 2305 and 2306 as shown in FIGS. 23A-C and 24). In further embodiments of sensor apparatus and sensor apparatus systems used in conjunction with a flexible membrane, a sensing probe may be used with a thermal well.

Figure 27:
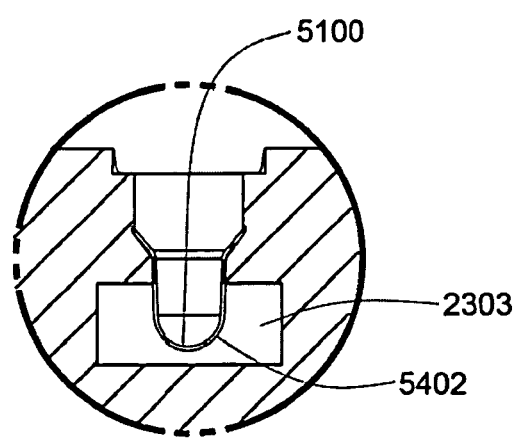
FIG. 27 is a close up certain features of FIG. 26.

As can be seen in FIG. 27, subject media is in contact with the outside of zone 5402 of the thermal well 5100. Thermal energy is transferred from the subject media to the thermal well 5100. As may be seen with reference to FIG. 13A-B, the thermal energy can them be further transferred to the tip 6002 of the sensing probe 6000. Thermal energy is then conducted to the thermal sensor 6014. The thermal sensor 6014 communicates via leads 6016 with equipment that can determine the temperature of the subject media based on feedback of the thermal sensor 6014. In embodiments where conductivity sensing is also desired, lead 6018 communicates with equipment that can determine the conductivity of the subject media. With respect to determining the conductivity of the subject media, in addition to the lead 6018, a second electrical lead/contact (not shown) would also be used. The second lead could be any probe or apparatus capable of sensing capacitance of the subject media, including, an electrical contact.

Heat transfer from the tip 6002 to the thermal sensor 6014 may be improved by the use of a thermal epoxy or thermal grease 6022.

Many different embodiments of sensing apparatus may be used in connection with a thermal well installed in a flexible cassette, including embodiments similar to those shown in FIGS. 14A-B, 15, and 16, and described above.

While several geometries have been described, many others could be shown to achieve desired performance characteristics.

In certain embodiments, exemplary cassette 2300 may be utilized in conjunction with a device (not shown) that locally applies positive and negative pressure, including positive and negative fluid pressure of the type described in U.S. Pat. No. 5,350,357 and other of the patents and patent applications referenced above, on the diaphragm regions overlying the valve stations and pump chambers. When cassette 2300 is utilized in conjunction with a pressure applying device (not shown), cassette 2300 may be connected to the device in a number of different ways and in a number of different positions. Preferably, in certain embodiments, cassette 2300 may be loaded in a device in other than a horizontal orientation, such as a vertical or substantially vertical orientation. Placement of the cassette in a vertical or substantially vertical orientation may offer certain advantages depending on the configuration of the cassette such as to avoid air entrapment and to optimize application of positive and negative pressure, including positive and negative fluid pressure of the type described in U.S. Pat. No. 5,350,357 and other of the patents and patent applications referenced above, to the cassette.

Figure 28:
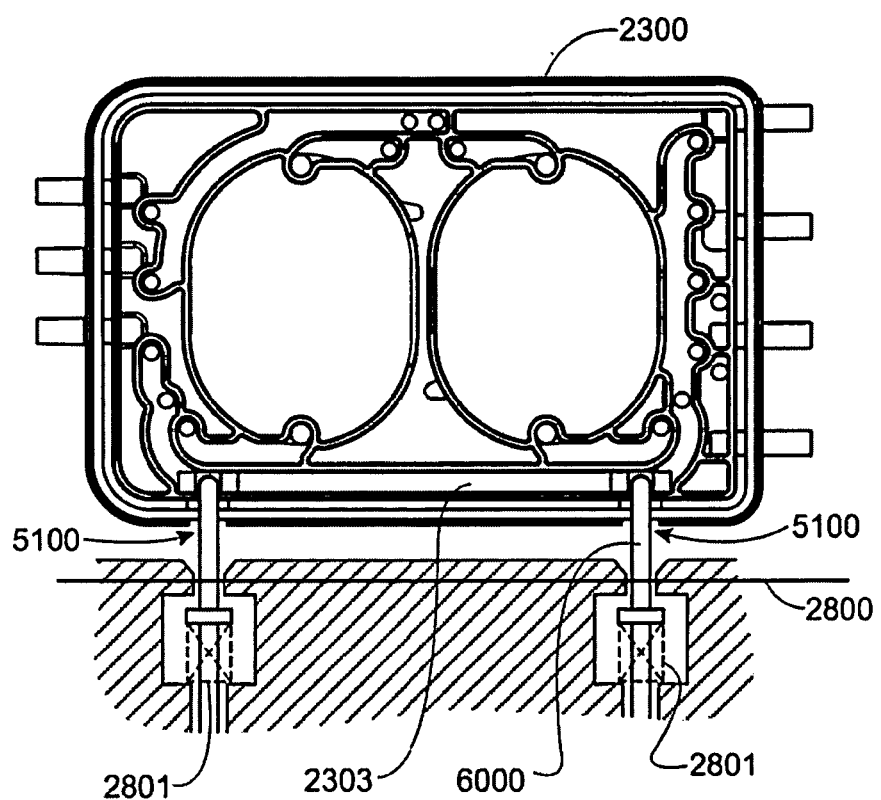
FIG. 28 is a section view of one embodiment of a sensing probe coupled to a thermal well installed in a cassette and suspended by a spring.

Referring now to FIG. 28, a sensor apparatus system of the type generally shown may be used in connection with exemplary cassette 2300. In the system, the sensor apparatus is installed in sensor ports 2305 and 2305 (not shown) extending into fluid path 2303. The sensor apparatus includes the sensing probe 6000 and the thermal well 5100. In this embodiment, the thermal well 5100 and fluid line 2303 is contained in an exemplary cassette 2300. In certain embodiments, exemplary cassette 2300 is intended to be disposable. Sensing probe 6000 is mounted in a reusable portion. Also in the reusable portion is a spring 2801. The spring 2801 and sensing probe 6000 are located in a housing 2800. The housing 2800 can be in any machine, container, device or otherwise. In certain embodiments the reusable portion in contained in or otherwise a part of a pressure applying device (as described above). The spring 2801 can be a conical, a coil spring, wave spring, or urethane spring.

In certain embodiments, the thermal well 5100 and the sensing probe 6000 may include alignment features (of the type shown in FIG. 17, 6702, 6704) that aid in the thermal well 5100 and sensing probe 6000 being aligned. The correct orientation of the thermal well 5100 and the sensing probe 6000 may aid in the mating of the thermal well 5100 and the sensing probe 6000 to occur. Referring again to FIG. 28, the configuration of the housing 2800 may provide the sensing probe 6000 with space for lateral movement. This allows the sensing probe 6000 to, if necessary; move laterally in order to align with the thermal well 5100 for mating.

In various embodiments, the sensing probe 6000 is configured with respect to the housing 2800 (as shown in FIG. 28) to facilitate engagement between the sensing probe 6000 and the thermal well 5100 and to aid in establishing full contact of the sensing probe 6000 and the thermal well 5100. Variations of the configurations generally shown in FIGS. 18-20 and described above may be used in conjunction with exemplary cassette 2300.

In other embodiments, the sensing probe may be aligned and positioned by other housing configurations. Thus, the embodiments of the housing shown herein are only some embodiments of housings in which the sensor apparatus can be used. The sensor apparatus generally depends on being located amply with respect to the subject media. The configurations that accomplish this can vary depending on the subject media and the intended use of the sensing apparatus. Further, in some embodiments where the thermal well is not used, but rather, the sensing probe is used only. The housing configurations may vary as well.

In embodiments in which cassette 2300 is loaded into a device, such as a pressure applying device, in a vertical or substantially vertical orientation, it may be preferable for sensor ports 2305 and 2306 to be positioned in the bottom edge of cassette 2300 (the bottom edge as the cassette is shown in FIG. 23A). Positioning of the sensor ports 2305 and 2306 along the bottom edge of exemplary cassette 2300 (such that sensor ports 2305 and 2306 and installed thermal wells 5100 extend into the bottom fluid line 2303 of the cassette) may facilitate engagement with the sensor apparatus as shown in FIG. 28. In certain of these embodiments, the exemplary cassette 2300 with installed thermal wells 5100 may be placed in position over sensor probes 6000, and then rotated vertically down and onto the sensor probes 6000.

The sensing apparatus, in some embodiments, is used to sense conductivity of the subject media within a fluid line within a cassette. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Referring now to FIG. 21, for conductivity sensing, at least two sensors 7102, 7104 are located in an area containing the subject media. In the embodiment shown, the area containing the subject media is a fluid path 5104 inside a fluid line 5108. The conductivity sensors 7102, 7104 can be one of the various embodiments of sensing probes as described above, or one of the embodiments of the sensor apparatus embodiments (including the thermal well) as described above.

Referring now to FIG. 28, sensing probes 6000 installed in thermal wells 5100 in sensor ports 2305 and 2306 can be used for sensing the conductivity of the subject media located between sensor ports 2305 and 2306 in fluid line 2303. However, in other embodiments, only one of the sensors is one of the embodiments of the sensor apparatus or one of the embodiments of the sensing probe, and the second sensor is any electrical sensor known in the art. Thus, in the systems described herein, conductivity and temperature can be sensed through using either one of the sensor apparatus or one of the sensor probes as described herein and a second capacitance sensor, or one of the sensor apparatus or one of the sensor probes as described herein and an electrical sensor.

3.2.2. Pod Pump Cassette

Cassettes other than the flexible membrane cassette described above may be used in conjunction with the sensor apparatus and sensor apparatus systems described herein. Cassette, such as cassettes of the types described in patent application Ser. No. 11/787,213 entitled Heat Exchange Systems, Devices and Methods which was filed on Apr. 13, 2007; patent application Ser. No. 11/787,212 entitled Fluid Pumping Systems, Devices and Methods which was filed on Apr. 13, 2007; and patent application Ser. No. 11/787,112 entitled Thermal and Conductivity Sensing Systems, Devices and Methods which was filed on Apr. 13, 2007 and issued as U.S. Pat. No. 7,794,141 on Sep. 14, 2010, all of which are hereby incorporated herein by reference in their entireties, may be used in conjunction with the sensor apparatus and sensor apparatus systems described herein. Additionally, cassettes, cassette assemblies, and manifolds of the types described in the following applications may be used in conjunction with the sensor apparatus and sensor apparatus systems described herein: U.S. patent application Ser. No. 11/871,680, filed Oct. 12, 2007 entitled Pumping Cassette; U.S. patent application Ser. No. 11/871,712, filed Oct. 12, 2007 entitled Pumping Cassette; U.S. patent application Ser. No. 11/871,787, filed Oct. 12, 2007 and entitled Pumping Cassette; U.S. patent application Ser. No. 11/871,793, filed Oct. 12, 2007 and entitled Pumping Cassette; and U.S. patent application Ser. No. 11/871,803, filed Oct. 12, 2007 and issued as U.S. Pat. No. 7,967,022 on Jun. 28, 2011 and entitled Cassette System Integrated Apparatus. Further, a variety of devices, including medical devices, such as the hemodialysis systems and methods of the types described in U.S. patent application Ser. No. 11/871,680, filed Oct. 12, 2007 entitled Pumping Cassette; U.S. patent application Ser. No. 12/072,908, filed Feb. 27, 2008 and issued as U.S. Pat. No. 8,246,826 on Aug. 21, 2012 and entitled Hemodialysis System and Methods; and U.S. patent application Ser. No. 12/038,648, filed Feb. 27, 2008 and issued as U.S. Pat. No. 8,042,563 on Oct. 25, 2011 and entitled Cassette System Integrated Apparatus, all of which are hereby incorporated herein by reference in their entireties.

In an exemplary embodiment of other cassettes used in conjunction with the sensor apparatus and sensor apparatus systems described herein, the cassette includes a top plate, a midplate and a bottom plate. In general, the top plate includes pump chambers, and potentially alternative or additional features; the midplate includes complementary fluid lines, metering pumps, valves and potentially alterative or additional features; and the bottom plate includes actuation chambers. In general, membranes are located between the midplate and the bottom plate; however, many alterative embodiments are possible. In the exemplary embodiment, the cassettes are formed by placing the membranes in their correct locations, assembling the plates in order and laser welding the plates. The cassettes may be constructed of a variety of materials. Generally, in the various exemplary embodiment, the materials used are solid and non flexible. In the preferred embodiment, the plates are constructed of polysilicone, but in other embodiments, the cassettes are constructed of any other solid material and in exemplary embodiment, of any thermoplastic.

Figure 29:
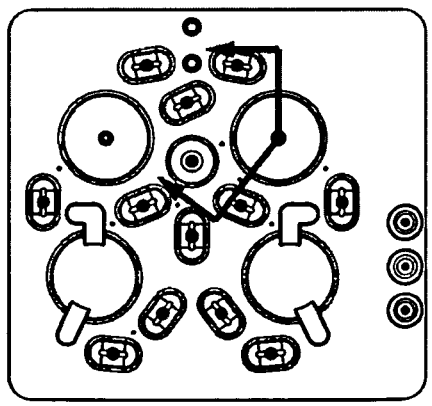
FIG. 29 is a sectional view of one embodiment of a pod-pump that is incorporated into embodiments of cassette.
Figure 29:
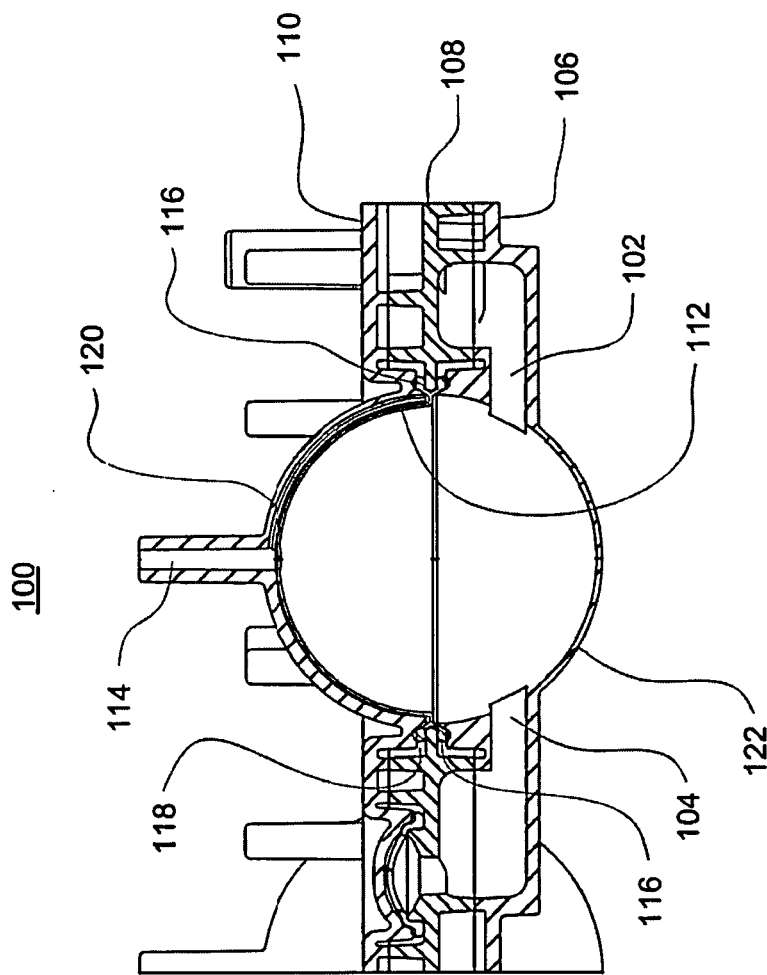

FIG. 29 is a sectional view of an exemplary pump pod 100 that is incorporated into a fluid control or pump cassette, in accordance with an exemplary embodiment of the cassette. In this embodiment, the pump pod is formed from three rigid pieces, namely a "top" plate 106, a midplate 108, and a "bottom" plate 110 (it should be noted that the terms "top" and "bottom" are relative and are used here for convenience with reference to the orientation shown in FIG. 29). The top and bottom plates 106 and 110 include generally hemispheroid portions that when assembled together define a hemispheroid chamber, which is a pump pod 100. A membrane 112 separates the central cavity of the pump pod into two chambers.

Figure 30A:
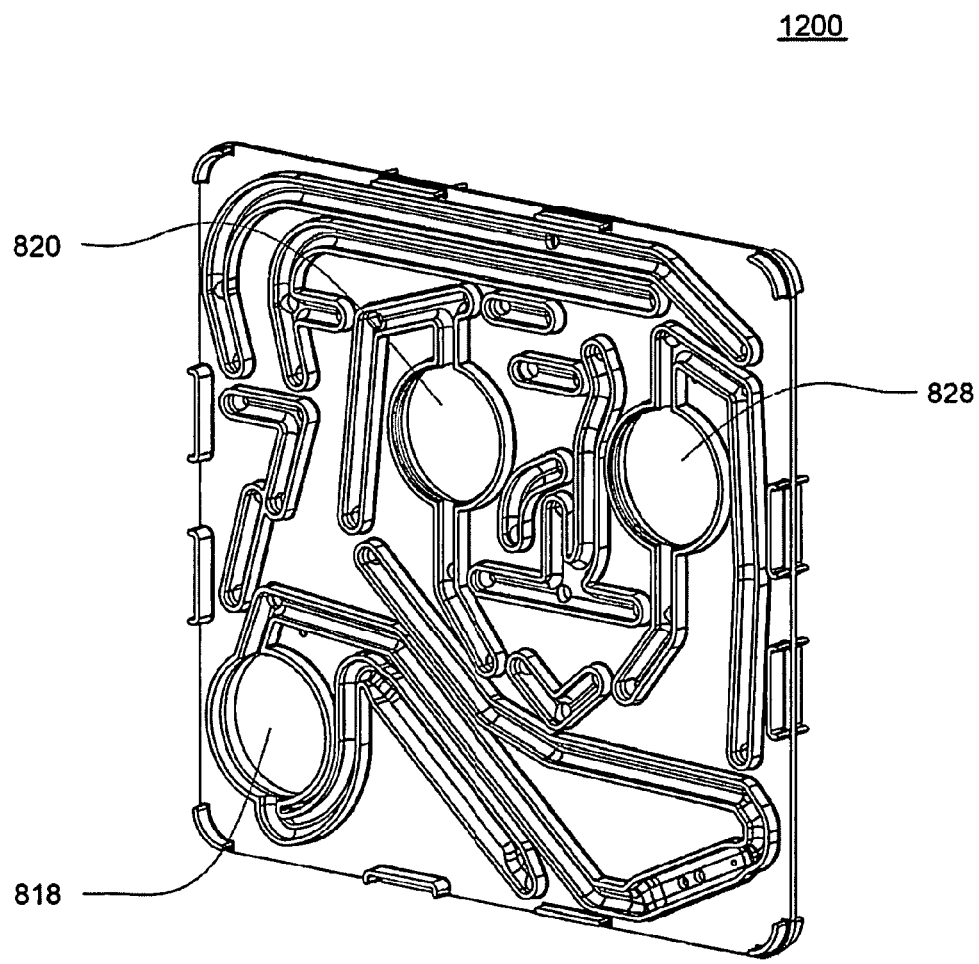
FIG. 30A is a front and isometric view of the exemplary embodiment of the fluid side of the midplate of the cassette.
Figure 30B:
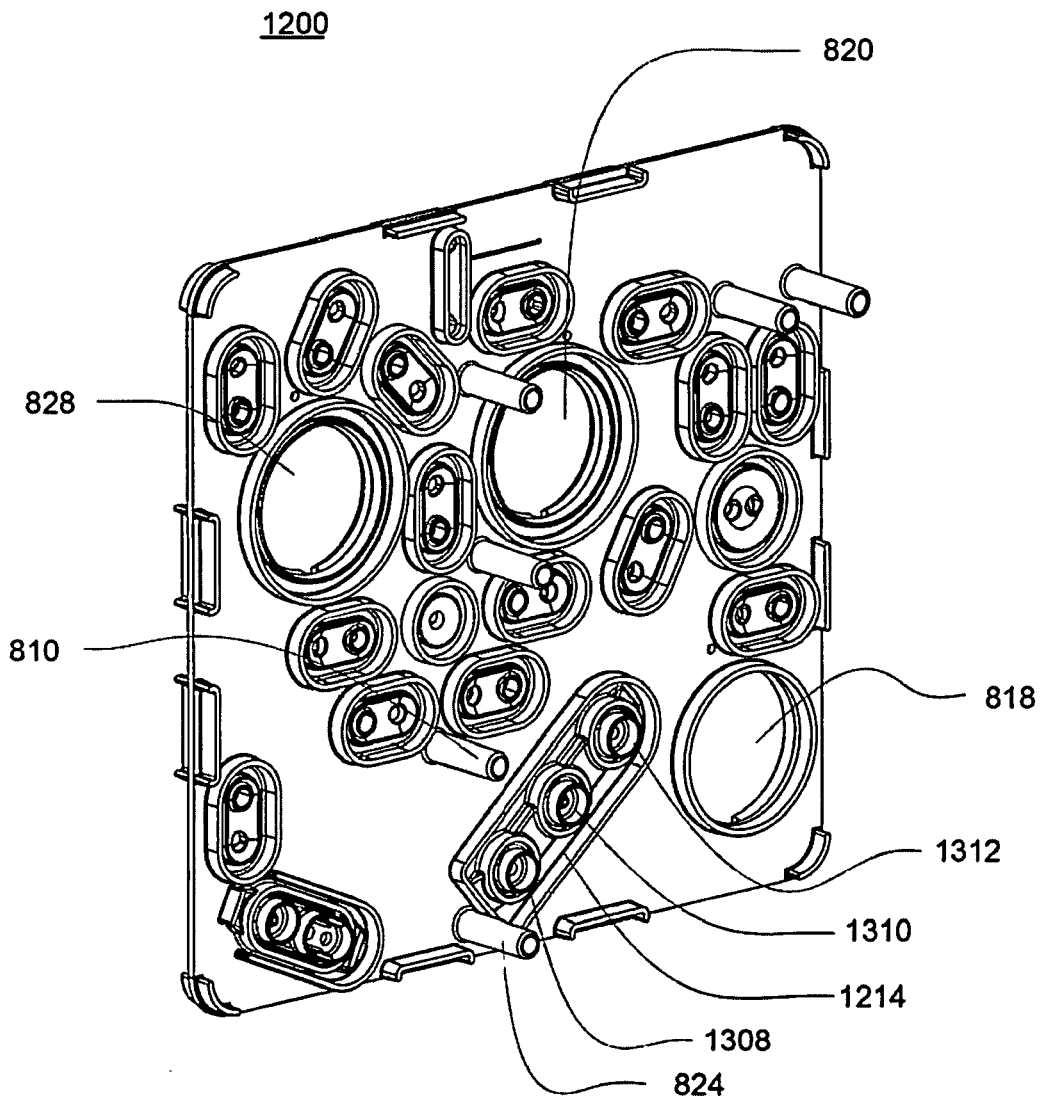
FIG. 30B is a front and isometric view of the exemplary embodiment of the air side of the midplate of the cassette.

Referring now to FIGS. 30A-B, in the exemplary embodiment of the cassette, sensors are incorporated into the cassette so as to discern various properties of subject media contained in or flowing through the cassette. In various embodiments one sensor may be included to sense temperature and/or other properties of the subject media. In another embodiment, two sensors may be included, to sense temperature and/or conductivity and/or other properties of the subject media. In yet further embodiments, three or more sensors may be included. However, in the exemplary embodiment, 6 sensors (2 sets of 3) are included. The sensors are located in the sensor block 1314, 1316. In this embodiment, a sensor block 1314, 1316 is included as an area on the cassette for a sensor(s). In the exemplary embodiment, the three sensors of the two sensor blocks 1314, 1316 are housed in respective sensor housings 1308, 1310, 1312 and 1318, 1320, 1322. In the exemplary embodiment, two of the sensor housings 1308, 1312 and 1318, 1320 accommodate a conductivity sensor and the third sensor housing 1310, 1322 accommodates a temperature sensor. The conductivity sensors and temperature sensor can be any conductivity or temperature sensor in the art. In one embodiment, the conductivity sensor elements (or sensor leads) are graphite posts. In other embodiments, the conductivity sensors elements are posts made from stainless steel, titanium, or any other material of the type typically used for (or capable of being used for) conductivity measurements. In certain embodiments, the conductivity sensors will include an electrical connection that transmits signals from the sensor lead to a sensor mechanism, controller or other device. In various embodiments, the temperature sensor can be any of the temperature sensors commonly used (or capable of being used) to sense temperature.

However, in alternate embodiments, a combination temperature and conductivity sensor is used of the types described above. In such alternate embodiments, thermal wells of the types described above may be installed in the cassette. In such embodiments, thermal well 5100 may be installed in the cassette by use of any of the ways described herein, including adhesive, welding (ultrasonic and otherwise), o-ring, retaining plate, and otherwise.

In alternate embodiments, there are either no sensors in the cassette or only a temperature sensor, only one or more conductivity sensors or one or more of another type of sensor.

Figure 31A:
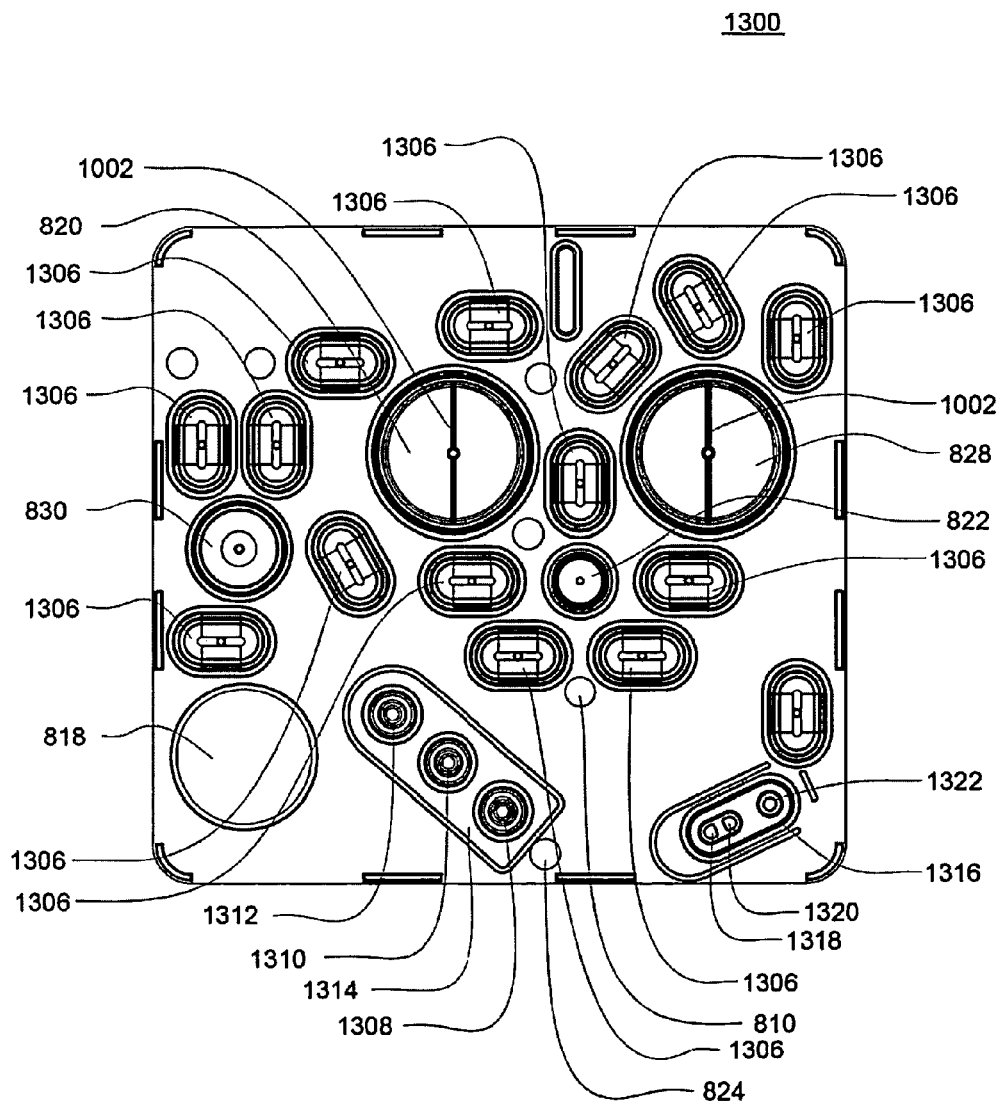
FIG. 31A is a front and isometric view of the exemplary embodiment of the inner side of the bottom plate of the cassette.

Referring now to FIGS. 31A-13B, the bottom plate 1300 is shown. Referring first to FIG. 31A, the inner or inside surface of the bottom plate 1300 is shown. The inner or inside surface is the side that contacts the bottom surface of the midplate (not shown). The bottom plate 1300 attaches to the air or actuation lines (not shown). The corresponding entrance holes for the air that actuates the pod pumps 820, 928 and valves (not shown) in the midplate can be seen 1306. Holes 810, 824 correspond to the first fluid inlet and first fluid outlet shown in FIGS. 30B, 810, 824 respectively. The corresponding halves of the pod pumps 820, 828 and mixing chamber 818 are also shown, as are the raised fluid paths 1002 for the fluid paths. The actuation holes in the pumps are also shown. Unlike the top plate, the bottom plate 1300 corresponding halves of the pod pumps 820, 828 and mixing chamber 818 make apparent the difference between the pod pumps 820, 828 and mixing chamber 818. The pod pumps 820, 828 include an air/actuation path on the bottom plate 1300, while the mixing chamber 818 has identical construction to the half in the top plate. The mixing chamber 818 mixes liquid and therefore, does not include a membrane (not shown) nor an air/actuation path. The sensor block 1310, 1316 with the three sensors housings 1308, 1310, 1312 and 1318, 1320, 1322 are also shown.

Figure 31B:
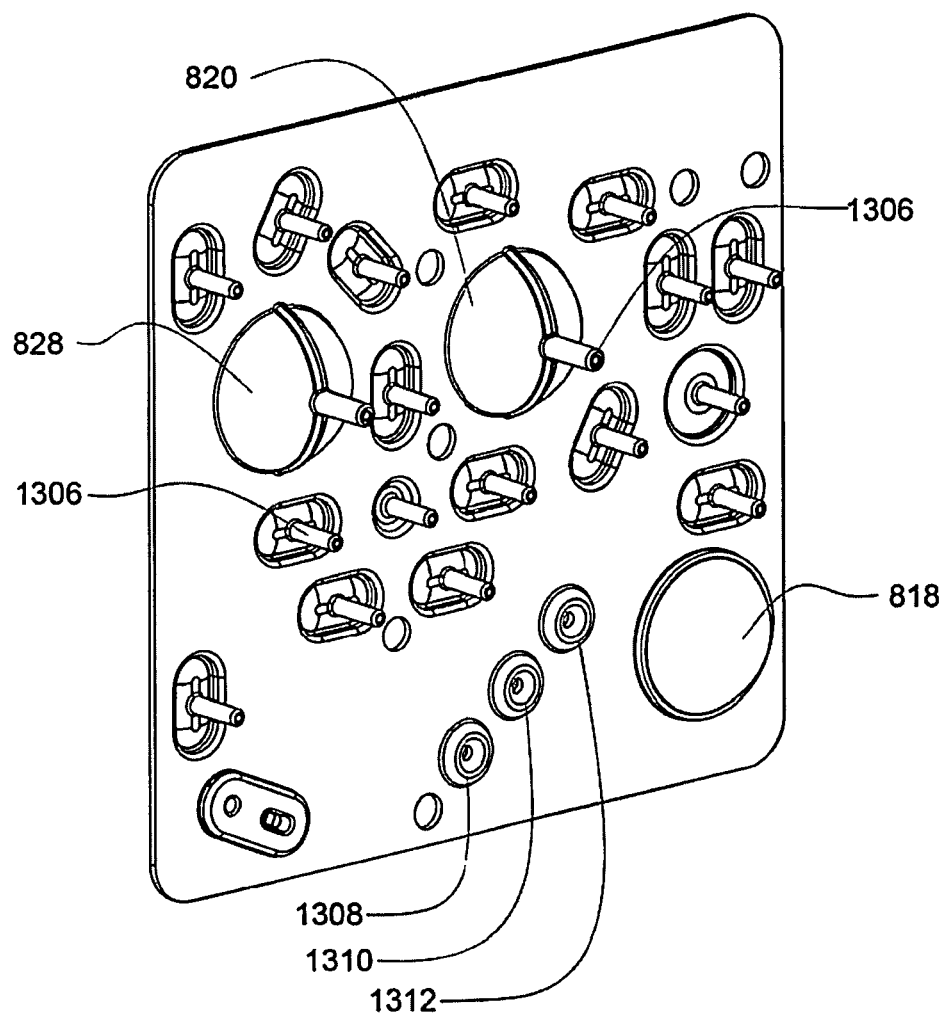
FIG. 31B is a front and isometric view of the exemplary embodiment of the outer side of the bottom plate of the cassette.
Figure 31C:
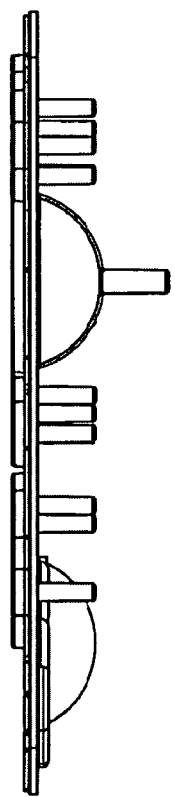
FIG. 31C is a side view of the exemplary embodiment of the midplate plate of the cassette.

Referring now to FIG. 31B, the actuation ports 1306 are shown on the outside or outer bottom plate 1300. An actuation source is connected to these actuation ports 1306. Again, the mixing chamber 818 does not have an actuation port as it is not actuated by air. Referring to FIG. 31C, a side view of the exemplary embodiment of the bottom plate 1300 is shown.

Figure 32A:
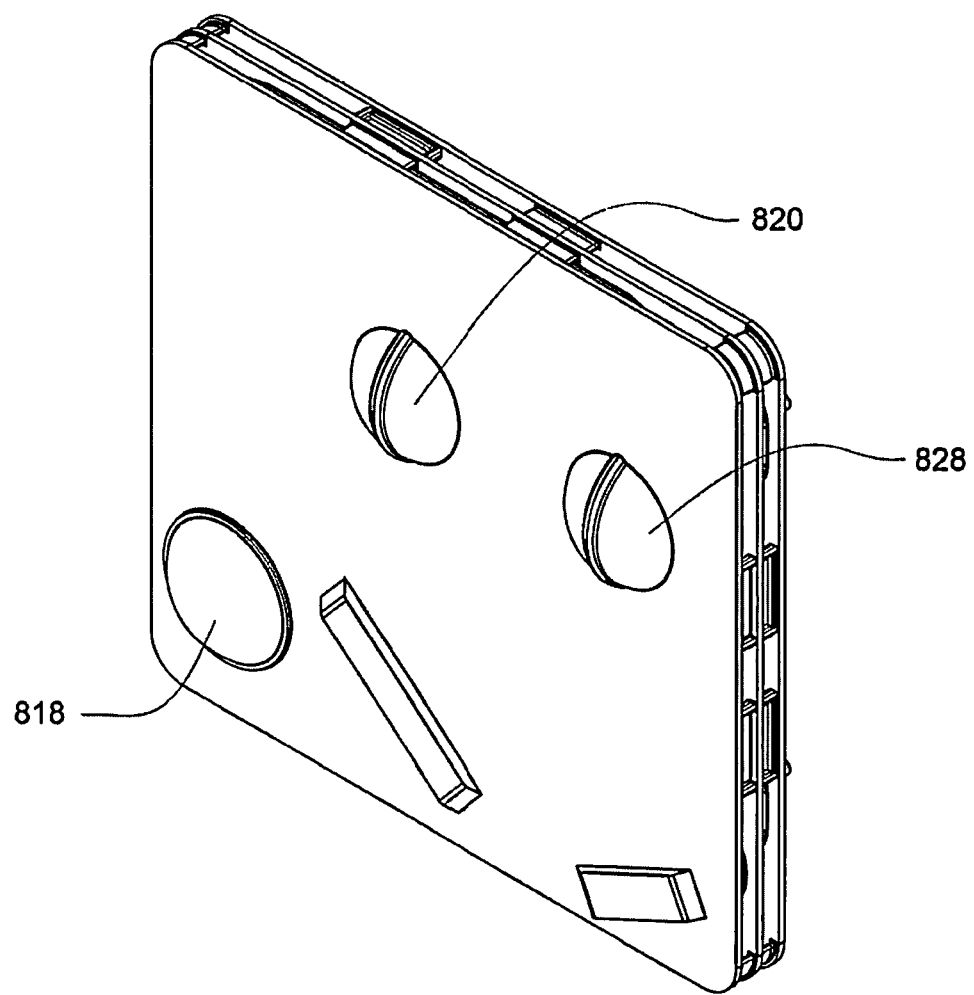
FIG. 32A is a top view of the assembled exemplary embodiment of the cassette.
Figure 32B:
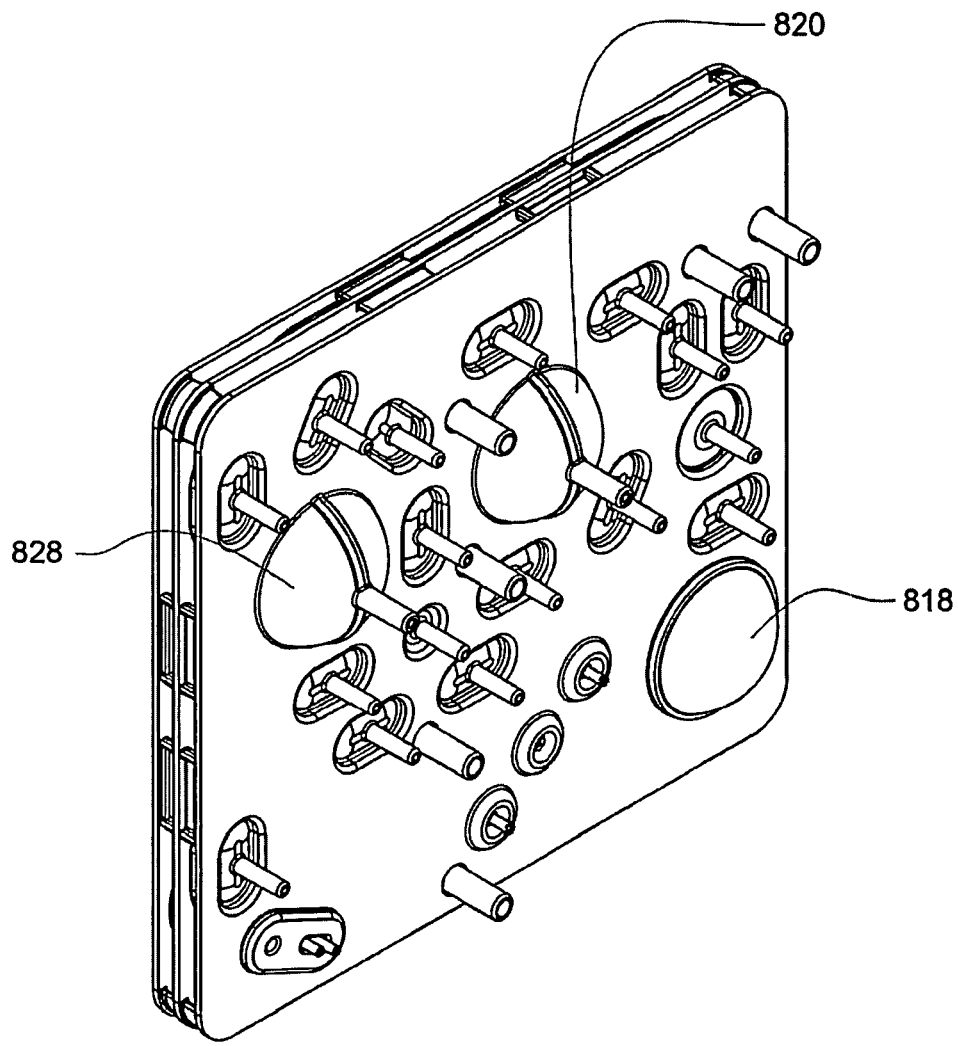
FIG. 32B is a bottom view of the assembled exemplary embodiment of the cassette.
Figure 32C:
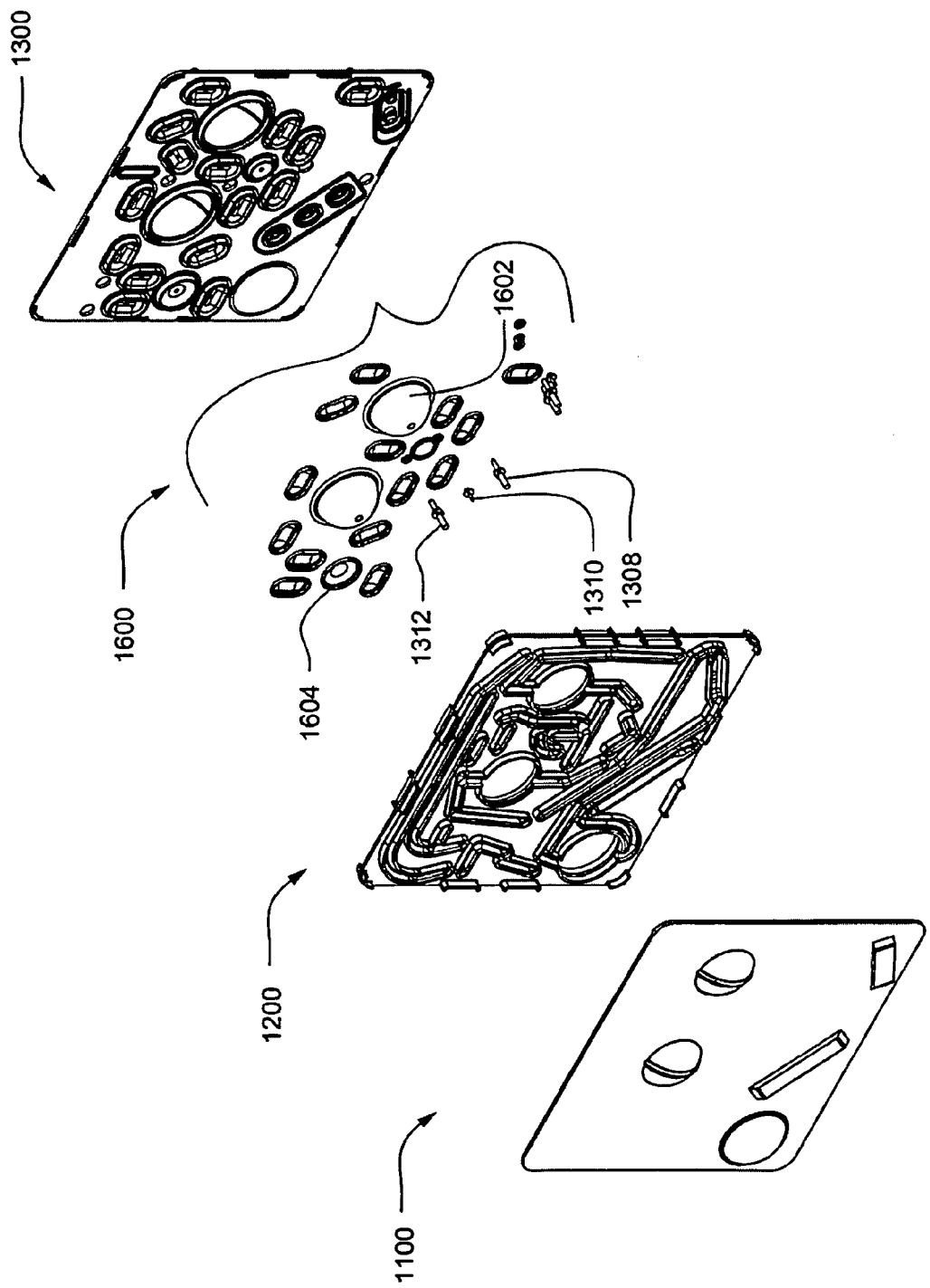
FIG. 32C is an exploded view of the assembled exemplary embodiment of the cassette.
Figure 32D:
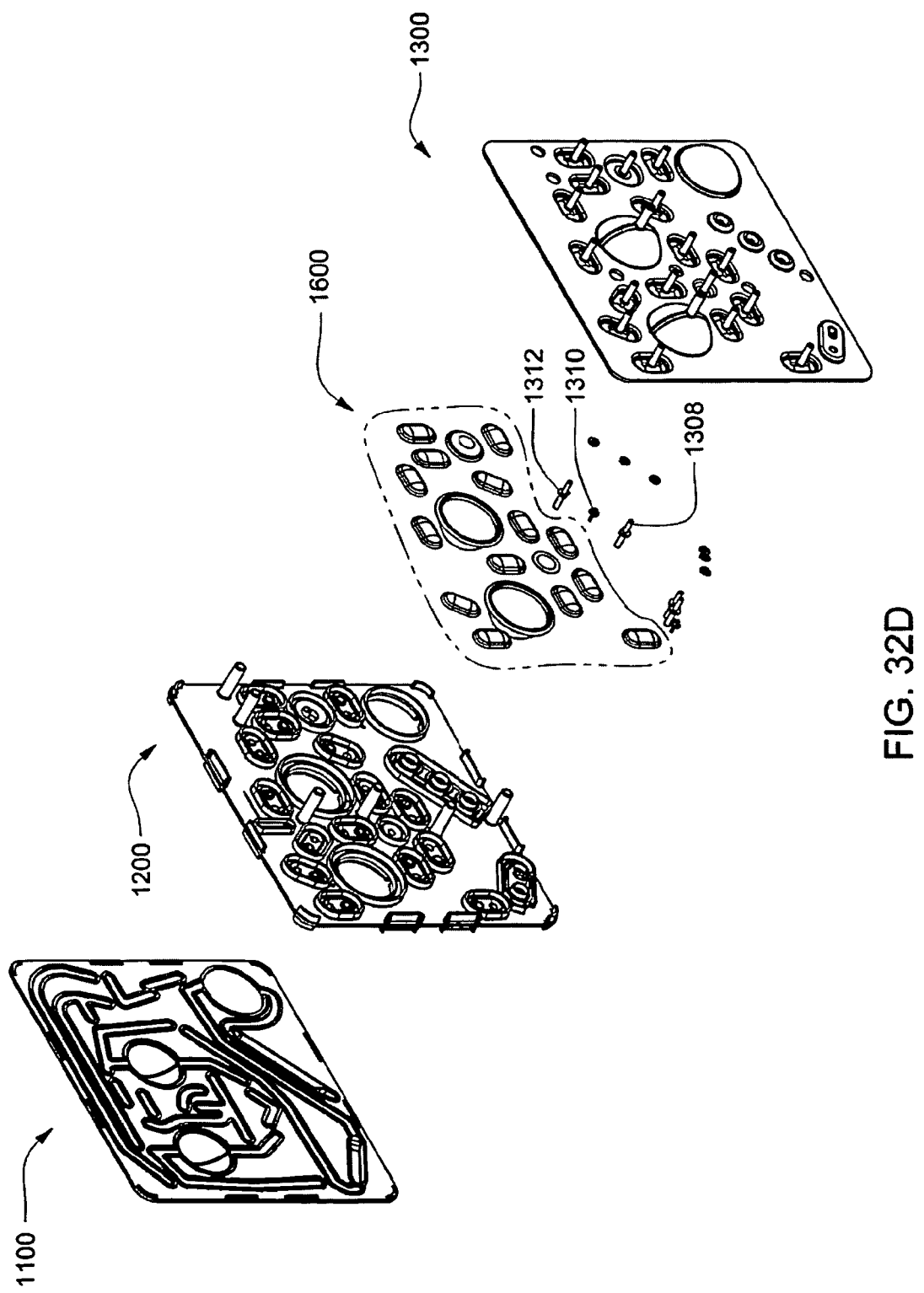
FIG. 32D is an exploded view of the assembled exemplary embodiment of the cassette.

Referring next to FIGS. 32A and 32B, the assembled exemplary embodiment of the cassette 1400 is shown. FIGS. 32C and 32D are exploded view of the exemplary embodiment of the cassette 1400. One embodiment of the conductivity sensors 1214, 1216 and the temperature sensor 1218, which make up the sensor cell 1212, are also shown in FIGS. 32C and 32D. Still referring to FIGS. 32C and 32D, the sensors are housed in sensor blocks (shown as 1314, 1316 in FIGS. 30B and 31A) which include areas on the bottom plate 1300 and the midplate 1200. O-rings seal the sensor housings from the fluid lines located on the upper side of the midplate 1200 and the inner side of the top plate 1100. However, in other embodiments, an o-ring is molded into the sensor block or any other method of sealing can be used.

Figure 33A:
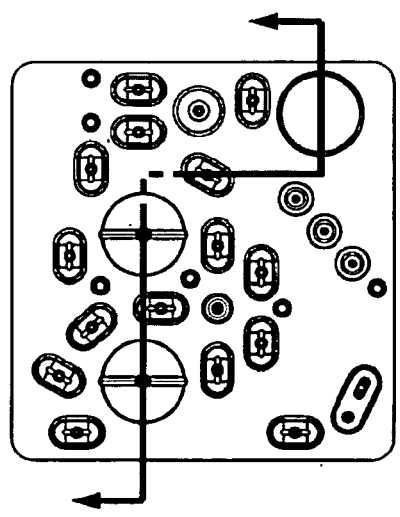
FIGS. 33A-33C show cross sectional views of the exemplary embodiment of the assembled cassette
Figure 33A:
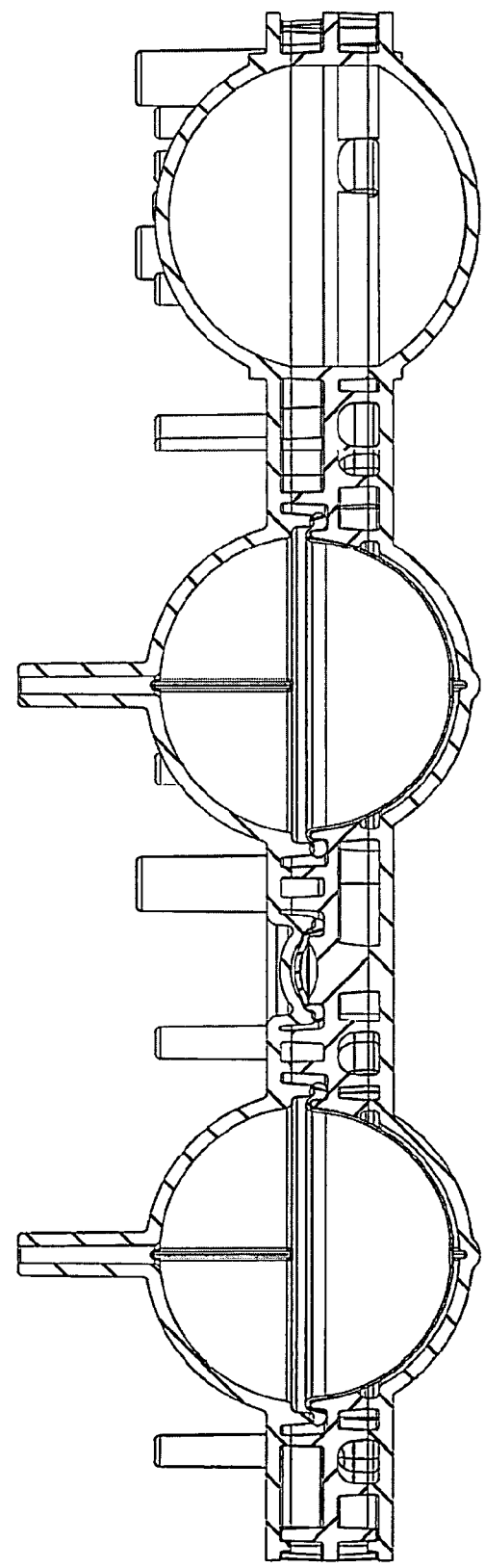
Figure 33B:
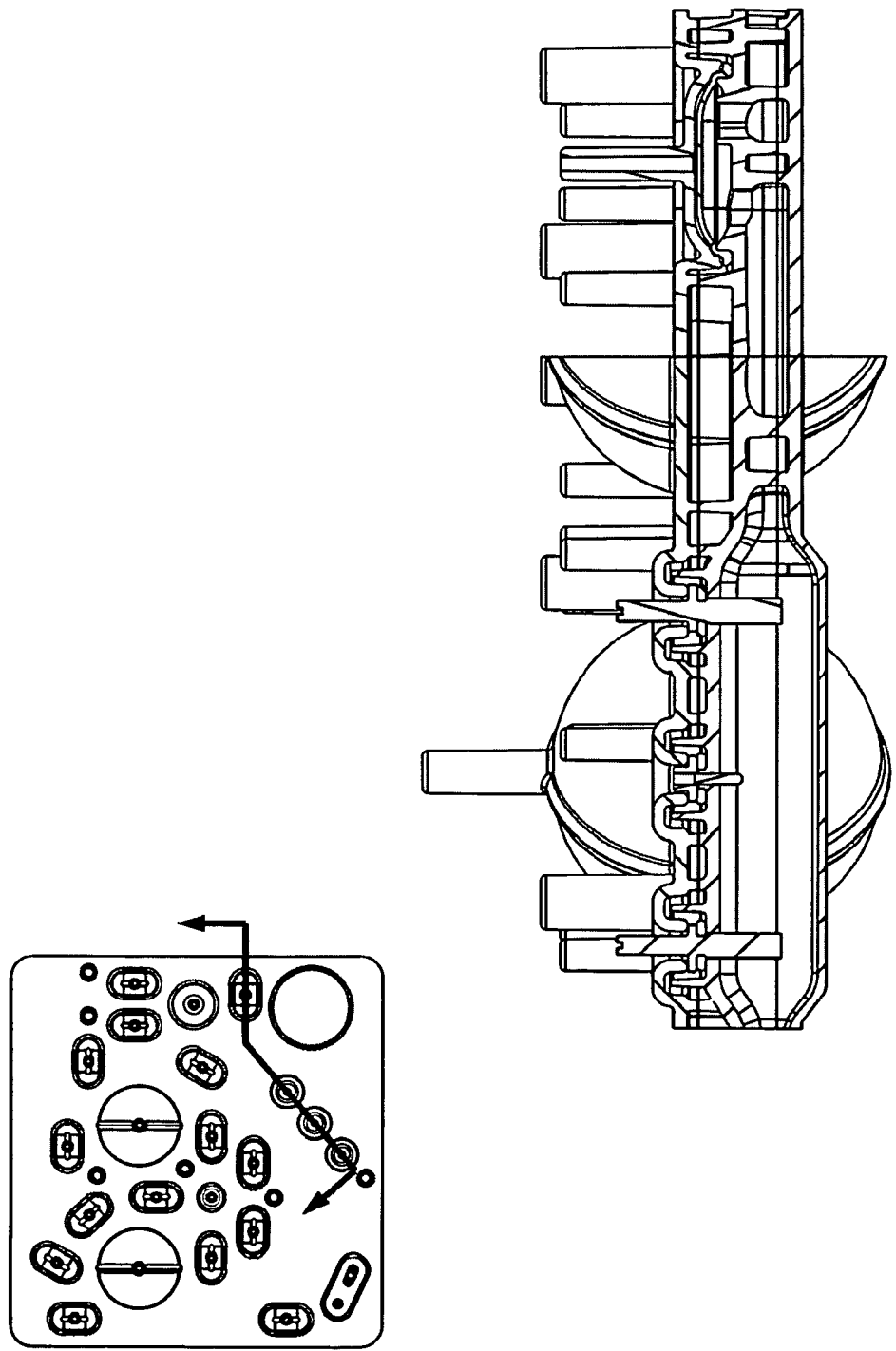
Figure 33C:
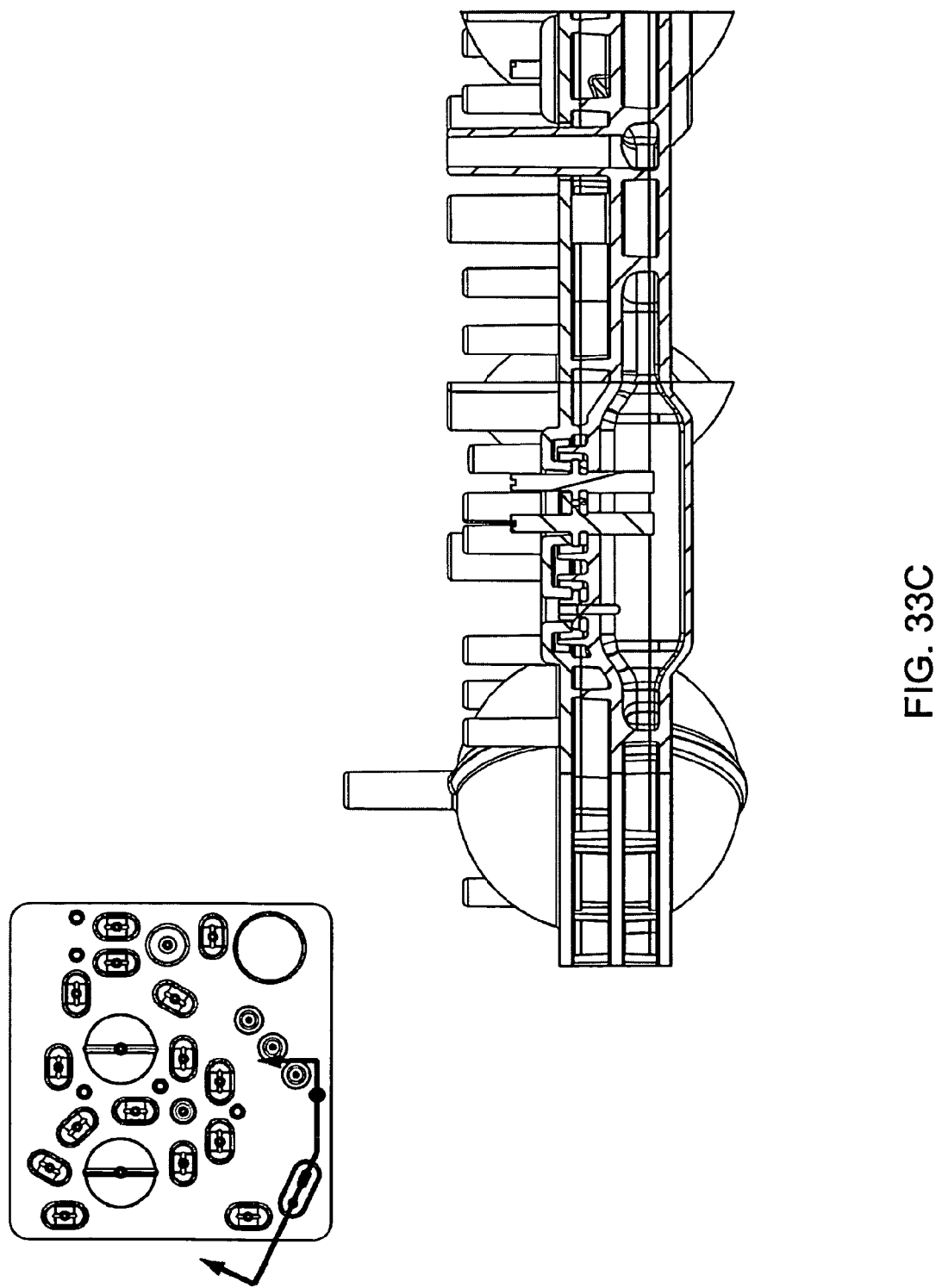

Referring now to FIGS. 33A-33C, various cross sectional views of the assembled cassette are shown. Referring now to FIG. 33B, the two conductivity sensors 1308, 1312 and the temperature sensor 1310 are shown. As can be seen from the cross section, the sensors 1308, 1310, 1312 are in the fluid line 824. Thus, the sensors 1308, 1310, 1312 are in fluid connection with the fluid line and can determine sensor data of the fluid exiting fluid outlet one 824. Still referring to FIG. 33B, a valve 826 cross section is shown.

Referring now to FIG. 33C, the two conductivity sensors 1318, 1320 and the temperature sensor 1322 are shown. As can be seen from the cross section, the sensors 1318, 1320, 1322 are in the fluid line 824. Thus, the sensors 1318, 1320, 1322 are in fluid connection with the fluid line and can determine sensor data of the fluid entering the mixing chamber (not shown in this figure).

Thus, in the exemplary embodiment, the sensors 1318, 1320, 1322 are used to collect data regarding fluid being pumped into the mixing chamber. Referring back to FIG. 30B, sensors 1308, 1310, 1312 are used to collect data regarding fluid being pumped from the mixing chamber and to the fluid outlet. However, in alternate embodiments, no sensors are or only one set, or only one type of sensor (i.e., either temperature or conductivity sensor) is used. Any type of sensor may be used and additionally, any embodiment of a temperature, a conductivity sensor or a combined temperature/conductivity sensor.

Figure 34:
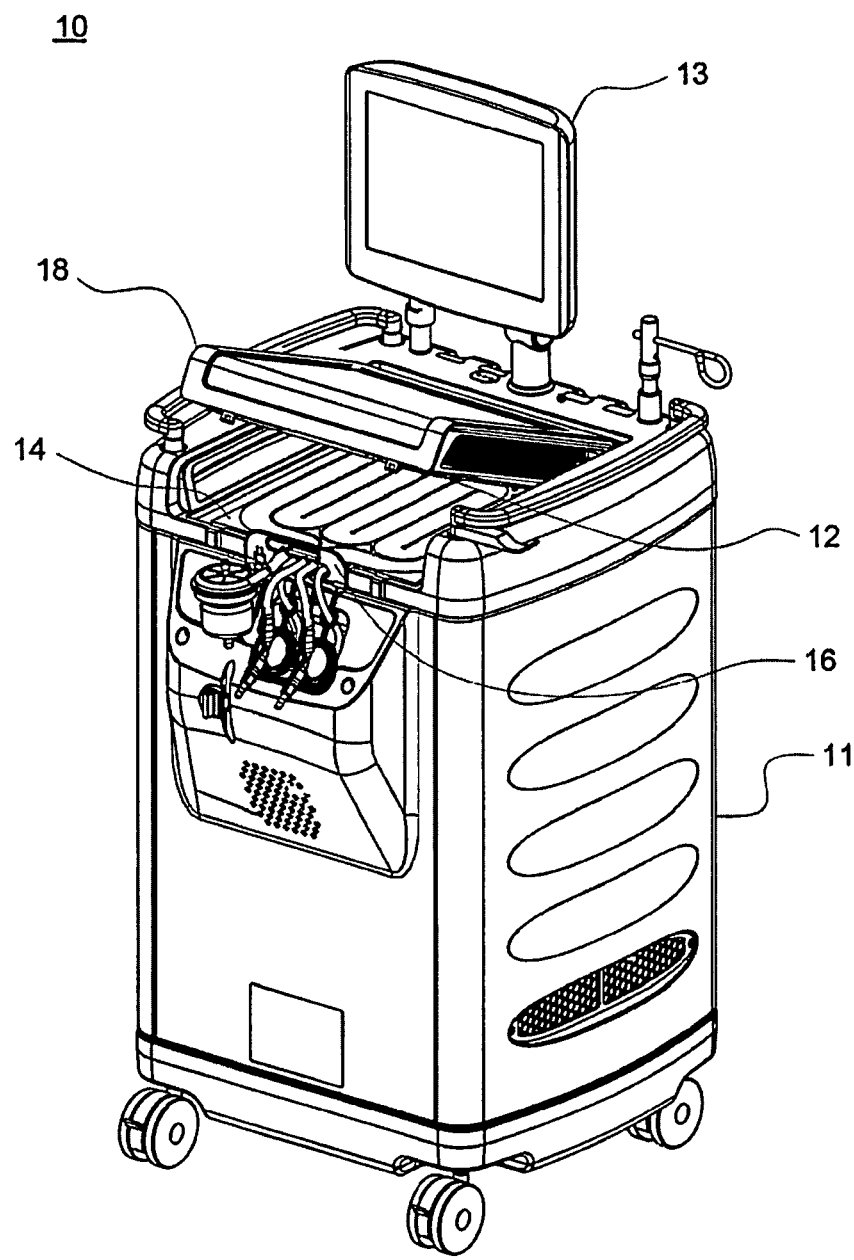
FIG. 34 is a perspective view of a system having a base unit with a disposable unit containing a manifold according to one embodiment of the invention.

3.3. Sensor Apparatus and Sensor Apparatus Systems Utilized in Connection with a Manifold FIG. 34 shows a system 10 in accordance with an exemplary embodiment of the present invention. System 10 includes a base unit 11 and a disposable unit 16 including a manifold. The disposable unit 16 is considered to be "disposable" in that it is generally discarded after a patient treatment, whereas the base unit 11 can be re-used repeatedly by simply installing a new disposable unit 16.

Figure 35:
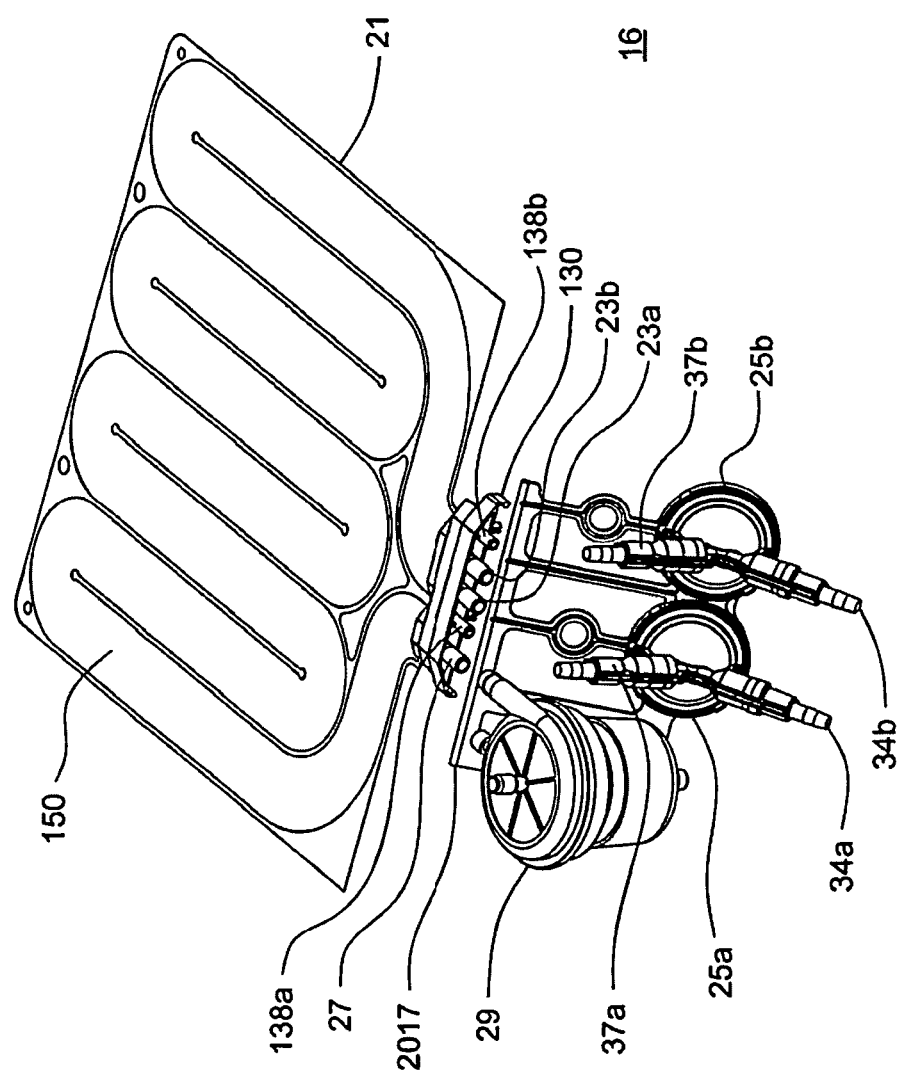
FIG. 35 is a perspective view of the disposable unit containing a manifold shown in FIG. 34.

FIG. 35 shows relevant components of a disposable unit 16, in accordance with an exemplary embodiment of the present invention. The disposable unit 16 includes, among other things, a manifold 130. The disposable unit 16 preferably also includes a handle (not shown) that is used to mechanically interconnect the above-referenced components into a cohesive unit that can be readily installed into the base unit 11, which preferably includes a manifold interface (described below) for receiving the manifold 130 and providing pneumatic and other connections. In this embodiment, the manifold 130 is integrated with the heat-exchanger bag 21 and is configured with appropriate tubing connections and supports that are used to interconnect the heat-exchanger bag 21 with the two pump pods 25a and 25b. In the embodiment shown in FIG. 35, the manifold 130 includes two flow-path inlets 23a and 23b (also referred to as "heat-exchanger bag inlets") in fluid communication with one end of the fluid path 150 and a flow-path outlet 27 (also referred to as a "heat-exchanger bag outlet") in fluid communication with the other end of the fluid path 150. In alternative embodiments, manifold 130 may be used in connection with disposable unit 16 that does not include a heat-exchanger bag or other components shown in FIG. 35.

Figure 38A:
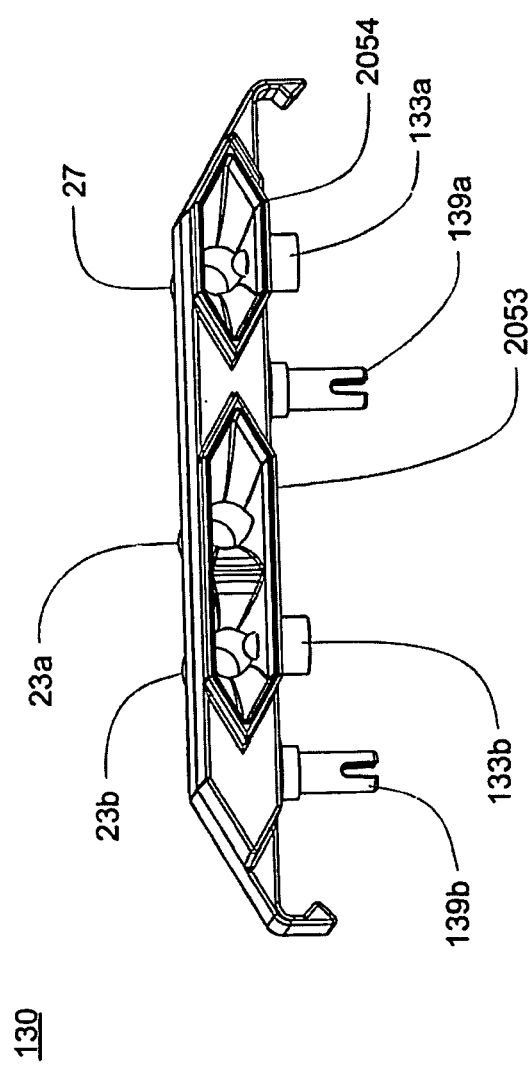
FIGS. 38A and 38B respectively show a perspective back-side view and a perspective bottom view of the manifold from FIG. 35, in accordance with an exemplary embodiment of the present invention.
Figure 38B:
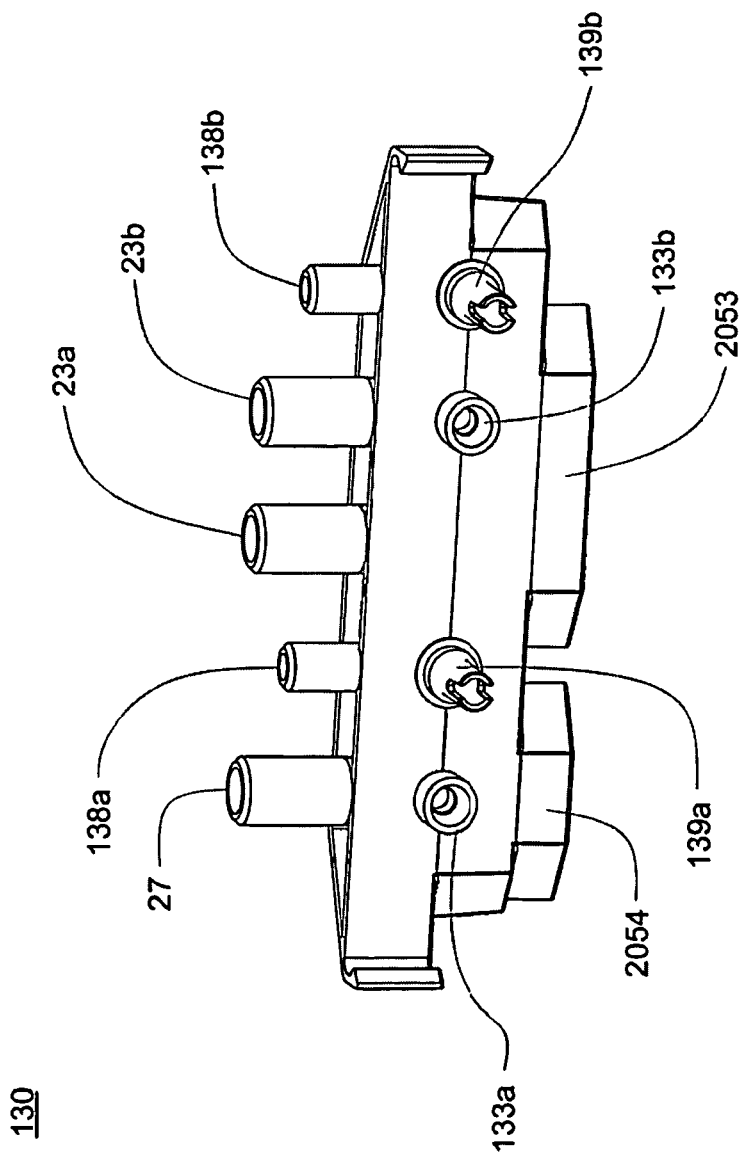

FIGS. 38A and 38B respectively show a perspective back-side view and a perspective bottom view of the manifold 130 from FIG. 35, in accordance with an exemplary embodiment of the present invention. FIG. 38A shows bag inlet and outlet connectors 2053, 2054 for connection at the inlet and outlet openings of the fluid channel 150 of the bag 21. The bag inlet connector 2053 is in fluid communication with the inlets 23a, 23b, while the bag outlet connector 2054 is in fluid communication with the outlet 27. The thermal wells 133a and 133b are shown in the outlet fluid path and the inlet fluid path, respectively.

Figure 36A:
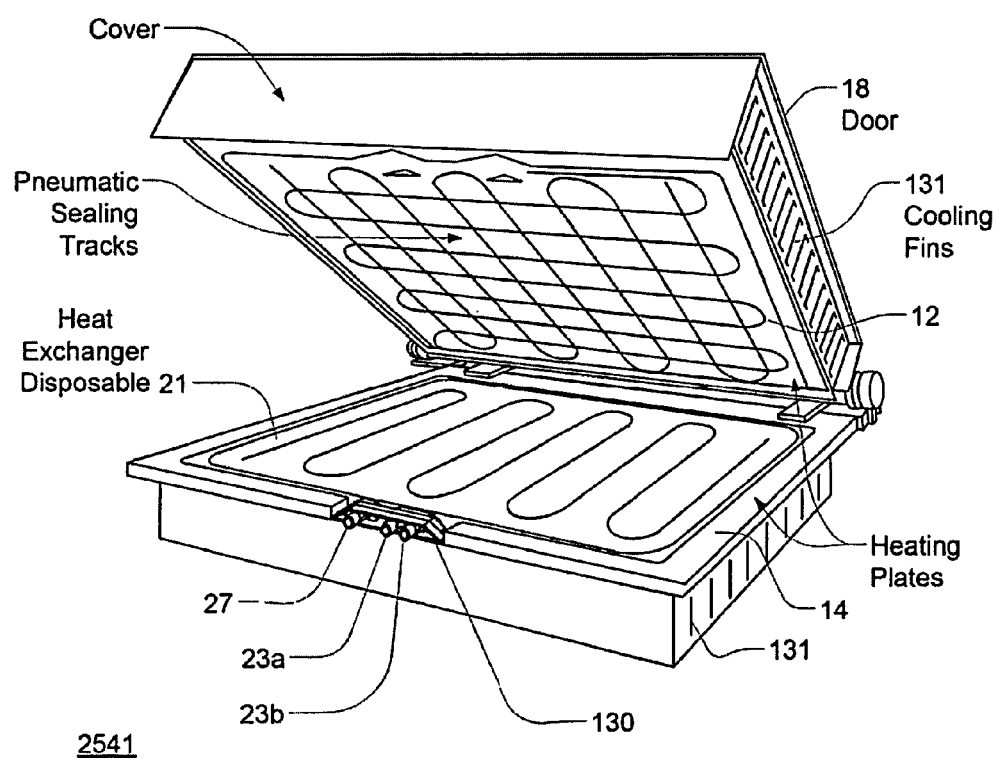
FIG. 36A is a perspective view of the components from the system of FIG. 34.
Figure 36B:
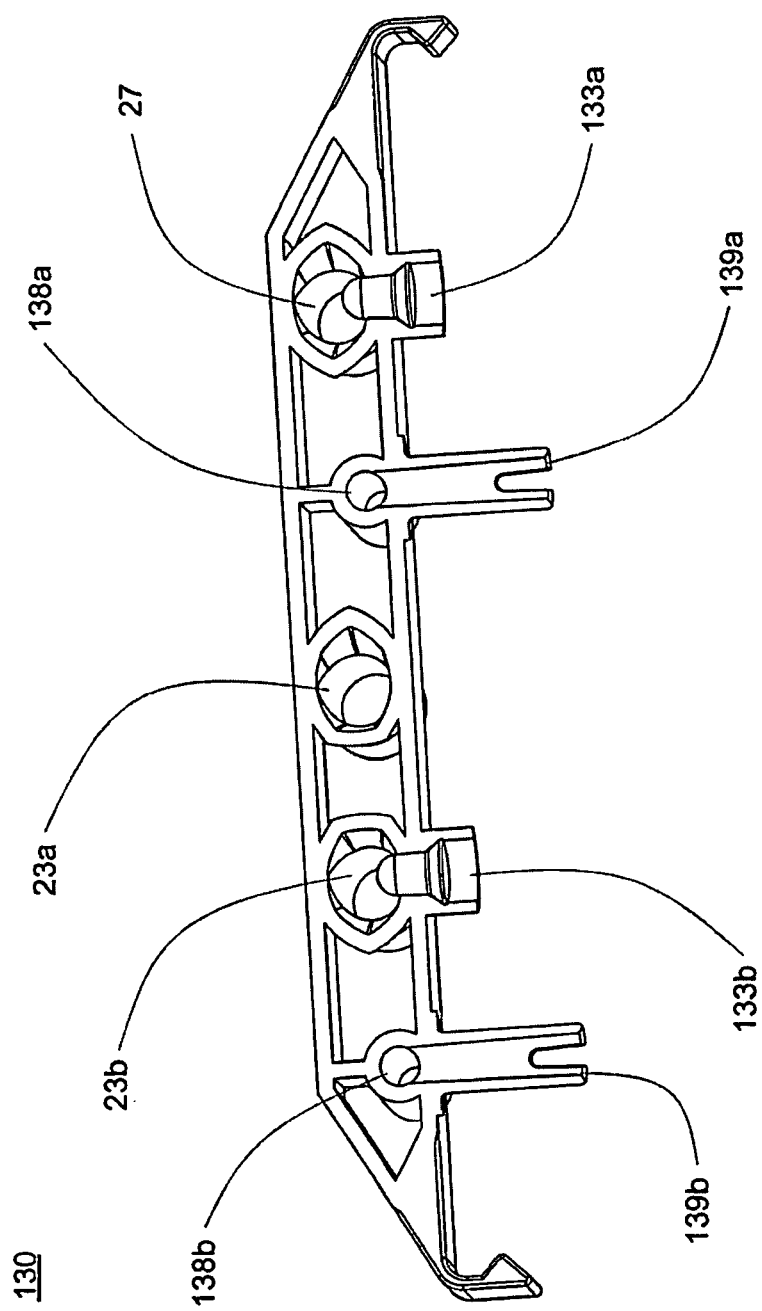
FIG. 36B is a perspective, back-side cross-sectional view of the manifold of FIGS. 35 and 38A-B, in accordance with an exemplary embodiment of the present invention.
Figure 36C:
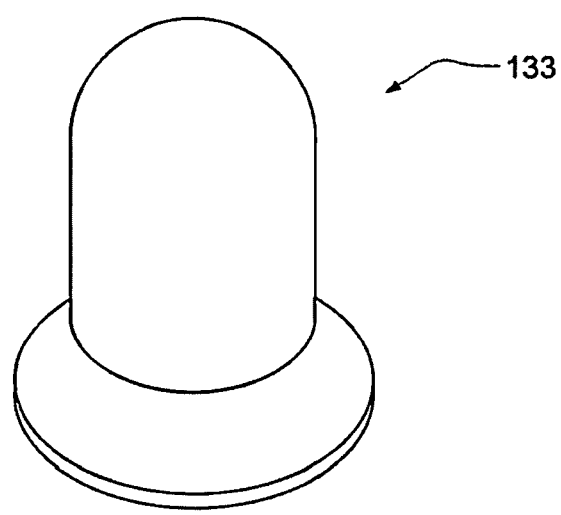
FIG. 36C shows a thermal well that may be used in the manifold of FIGS. 35, 36B, 38A and 38B in the heat-exchanger of FIG. 35, in accordance with an exemplary embodiment of the present invention.
Figure 37:
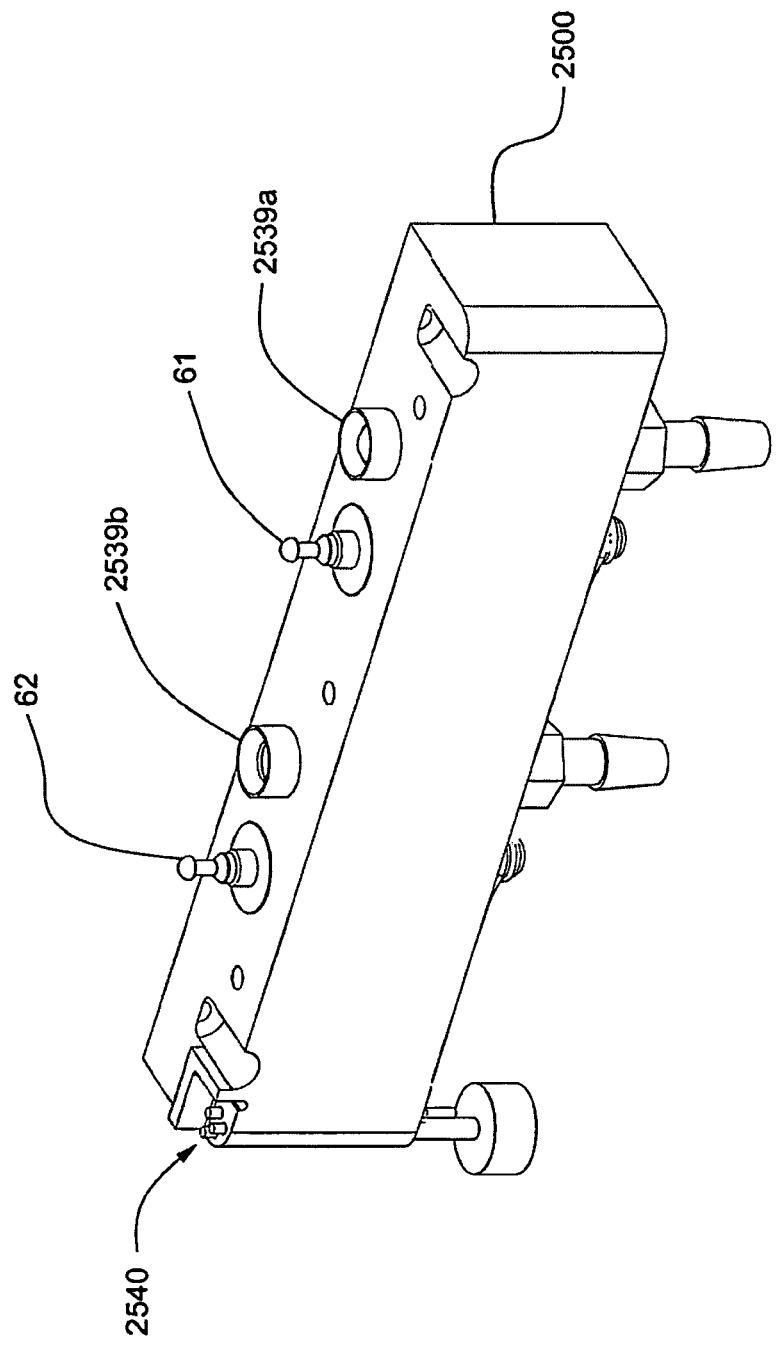
FIG. 37 shows a view of the manifold interface, in accordance with an exemplary embodiment of the present invention.

FIG. 36B shows a perspective back-side cross-sectional view of the manifold 130 of FIGS. 35, 38A, and 38B, in accordance with an exemplary embodiment of the present invention. In this embodiment, the manifold 130 includes an inlet thermal well 133a located in a bag inlet 23a and an outlet thermal well 133b located in a bag outlet 27. The thermal wells 133a, 133b interface with corresponding probes in a manifold interface of the base unit 11 (discussed below) when the disposable unit 16 is installed in the base unit 11. FIG. 36C shows a close-up view of an exemplary thermal well, although all of thermal well embodiments described herein may be utilized in connection with a manifold, such as manifold 130.

The thermal wells 133a, 133b provide for both thermal and electrical interconnections between the base unit 11 and the disposable unit 16. Among other things, such thermal and electrical interconnections allow the controller 49 to monitor blood temperature as the blood enters and exits the heat-exchanger bag 21 and also allow the controller 49 to take other measurements (e.g., to detect the presence of blood or air in the heat-exchanger bag 21 and to perform leak detection) as discussed below. In this embodiment, each of the thermal wells 133a, 133b is coupled so as to have a portion residing directly in the fluid path (i.e., in contact with the blood) so as to permit better transmission of blood temperature from the disposable unit 16 to the base unit 11. In lieu of, or in addition to, the thermal wells, the disposable unit 16 may include other temperature probes/sensors and interfaces by which the controller 49 can monitor blood temperature as the blood enters and exits the heat-exchanger bag 21.

While the exemplary embodiment shown in FIGS. 36B, 38A, and 38B include thermal wells for transmitting thermal information to the base unit 11 and optionally for use in conductivity sensing, it should be noted that other types of sensor components may be additionally or alternatively used. For example, rather than using a thermal well, a sensor component that sends temperature measurements or signals to the base unit 11 may be used. Various types and configurations of sensors are described below. In other embodiments, any of the sensor apparatus and sensor apparatus systems described herein may be used in conjunction with a manifold, such as manifold 130.

FIG. 26 shows a close-up view of the manifold interface 2500 shown in FIG. 25. The manifold interface 2500 includes, among other things, probes 61, 62 and pneumatic ports 2539a, 2539b. With reference again to FIG. 13B, it can be seen that the manifold 130 can be installed in the manifold interface 2500 such that the probes 61, 62 interface respectively with the thermal wells 133a, 133b and the pneumatic ports 2539a, 2539b interface respectively with the pneumatic interfaces 139a, 139b. The manifold interface 2500 also includes a data key interface 2540 for interfacing with a corresponding data key in the disposable unit. The data key interface 2540 preferably provides a bi-directional communication interface through which the controller 49 can read information from the disposable unit (e.g., serial/model number, expiration date, and prior usage information) and write information to the disposable unit (e.g., usage information). In an exemplary embodiment, the controller 49 may prevent the start of a treatment if the data key is not present or if the disposable unit is unusable, for example, because it includes an unacceptable serial/model number, is past a pre-configured expiration date, or has already been used. The controller 49 may terminate a treatment if the data key is removed. In lieu of a data key interface 2540, the base unit 11 or manifold interface 2500 may include other types of interfaces for reading information from the disposable unit and/or writing information to the disposable unit (e.g., RFID, bar code reader, smart key interface).

It should be noted that one or more pumps (e.g., pump pods) may be integral with a manifold such as the manifold 130 and placed in a base unit as a single cartridge. The assembly could include pneumatic connections from the pneumatic ports (which are connected to the base unit) directly to the pump actuation chambers so that no external tubing would be needed to make the pneumatic connections to the pump pods. The assembly could additionally or alternatively include fluidic connections (e.g., from the pump outlets to the interface with the heat-exchanger bag) so that no external tubing would be needed between the pump outlets and the manifold or bag.

3.4. Sensor Apparatus and Sensor Apparatus Systems Utilized in Connection with a Sensor Manifold In various embodiments of the inventions described herein, a sensor apparatus systems may be utilized that comprises a sensor manifold. A sensor manifold may allow subject media to be moved from one environment to another environment that is more conducive to obtaining sensor readings. For example, the cassette manifold may be contained in an area that is not subject to various types of environment conditions, such as temperature and/or humidity, which would not be preferable for sensor apparatus such as a sensing probe. Alternatively, sensing apparatus and sensing apparatus system may be delicate and may be probe to greater malfunctions than other components of a system. Separating the sensor apparatus and the sensor apparatus systems from the remainder of the system by use of a sensor manifold may allow the sensing apparatus and sensing apparatus systems to be repaired or replaced with minimal impact to the remainder of the system. Alternative, the sensor manifold may be replaced either more or less frequently than other components of the system.

Figure 39:
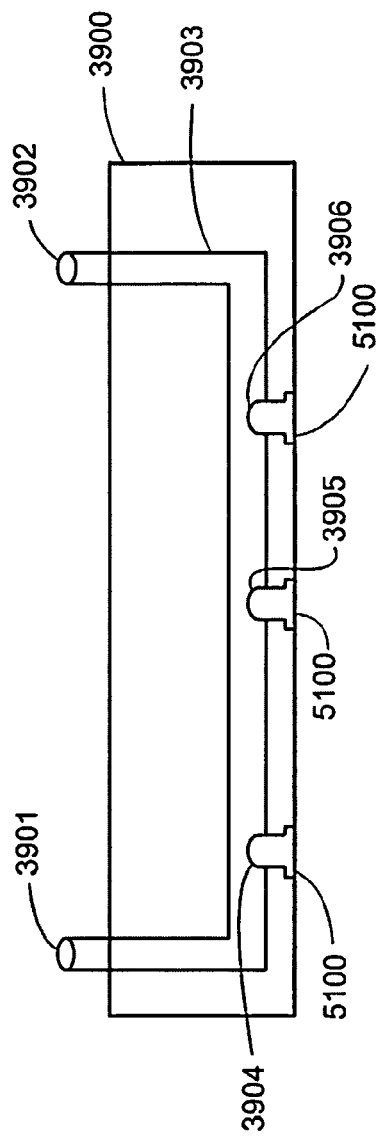
FIG. 39 is a view of an exemplary sensor manifold.

With reference to FIG. 39, an exemplary sensor manifold is shown. A subject media may be contained in or flow through cassette 3900. In this embodiment, cassette 3900 is comprised of a rigid body overlaid by one or more flexible diaphragms of the types described herein. Pre-molded tube connector 3901 allows subject media to enter sensor cassette 3900 from another source and flow through fluid path 3903. Subject media exits the cassette through pre-molded tube connector 3902. While tube connectors 3901 and 3902 are shown as pre-molded tube connectors, other embodiments may use any other fluid transfer devices to allow subject media into fluid path 3903.

With further reference to FIG. 39, cassette manifold 3900 includes sensor ports 3904, 3905, and 3906 that extend into fluid path 3903. Sensor ports 3904, 3905, and 3906 may be used to insert a sensing probe, thermal well or other sensing element to allow. Exemplary cassette manifold 3900 shows three sensor ports per cassette manifold, but any number of ports may be used depending on the configuration of the cassette manifold and the type of sensor or sensors used.

Again, with reference to FIG. 39, exemplary cassette manifold 3900 is shown with sensor ports 3904, 3905, and 3906 positioned in the rigid body of cassette manifold 3900. In the case of a rigid cassette body with two flexible membranes, one on either side of the rigid body, as shown in FIG. 39, in one embodiment sensor ports 3904, 3905, and 3906 may be position in the rigid body portion of the cassette (as shown in FIG. 39). However, in other embodiments, the sensor port may extend though one or more areas of the flexible diaphragm overlying the cassette manifold.

Referring again to FIG. 39, exemplary cassette manifold 3900 is shown with sensor ports 3904, 3905, and 3906 extending into fluid path 3903 such that a component placed in sensor ports 3904, 3905, and 3906 would come into direct contact with the subject media contained in or flowing through fluid path 3903. FIG. 39 additionally shows thermal wells 5100 installed in sensor ports 3904, 3905, and 3906. In certain embodiments, cassette manifold 2300 and thermal wells 5100 are separate parts. In some embodiments, the cassette manifold 3900 and thermal well 5100 are made from different materials. For these embodiments, the thermal well 5100 can be made from any materials, including but not limited to, plastic, metal, ceramic or a combination thereof. The material may depend in some part on the compatibility with the intended subject media. In other embodiments, thermal well 5100 could be made from the same material as cassette manifold 3900. In yet further embodiments, thermal well 5100 could be formed as a part of the structure of the rigid body of cassette manifold 3900.

The length and width of the thermal well 5100 utilized with exemplary cassette 2300 can be any length and width having the desired or tolerable accuracy characteristics and which properly positions any sensor or sensing probe utilized with thermal well 5100 sufficiently in contact with the subject media contained in or flowing through fluid path

2306. The length of thermal well 5100 may impact the fluid flow of the subject media in fluid path 2303 to a certain extent. It also should be understood that the length of the thermal well 5100 may also impact the turbulence of the fluid flow. Thus, the length and width of the thermal well 5100 may be changed to have greater or lesser impact on the fluid flow and turbulence of the fluid, while mitigating the other variables.

The shape of the thermal well 5100 is also a variable. Any shape desired is contemplated. However, the shape of the thermal well 5100, as with the other variables, is determined in part based on the intended use of the sensor apparatus. For purposes of description, an exemplary embodiment is described herein. However, the shape in the exemplary embodiment is not meant to be limiting. All of the various embodiments of thermal wells described herein may be used in conjunction with cassettes, such as exemplary cassette 2300.

FIG. 39 shows thermal wells 5100 installed in exemplary cassette manifold 3900. Thermal well 5100 may be installed in exemplary cassette manifold 3900 by use of the ways described herein, including adhesive, welding (ultrasonic and otherwise), o-ring, retaining plate, and otherwise. The thermal well 5100 used in connection with a cassette may be of various shapes and configurations. However, referring now to FIG. 4 for purposes of description, the embodiment of a thermal well 5100 shown may be utilized in conjunction with a cassette. In the exemplary embodiment shown in FIG. 4, the bottom zone 5406 is shaped to aid in press fitting the thermal well into the sensor port 2304, 3905, and 3906 shown in FIG. 39. Subject media may come into contact with the outside of zone 5402 of the thermal well 5100 as described above. Thermal energy is transferred from the subject media to the thermal well 5100. As may be seen with reference to FIG. 13A-B, the thermal energy can them be further transferred to the tip 6002 of the sensing probe 6000. Thermal energy is then conducted to the thermal sensor 6014. The thermal sensor 6014 communicates via leads 6016 with equipment that can determine the temperature of the subject media based on feedback of the thermal sensor 6014. In embodiments where conductivity sensing is also desired, lead 6018 communicates with equipment that can determine the conductivity of the subject media. With respect to determining the conductivity of the subject media, in addition to the lead 6018, a second electrical lead/contact (not shown) would also be used. The second lead could be any probe or apparatus capable of sensing capacitance of the subject media, including, an electrical contact.

Heat transfer from the tip 6002 to the thermal sensor 6014 may be improved by the use of a thermal epoxy or thermal grease 6022.

Many different embodiments of sensing apparatus may be used in connection with a thermal well installed in a flexible cassette manifold, including embodiments similar to those shown in FIGS. 14A-B, 15, and 16, and described above.

In certain embodiments of sensor apparatus and sensor apparatus systems used in conjunction with a flexible membrane cassette, a sensing probe may be installed directly into sensing ports 3904, 3905, and 3906 (shown in FIG. 39). In further embodiments of sensor apparatus and sensor apparatus systems used in conjunction with a flexible membrane, a sensing probe may be used with a thermal well.

In embodiments in which cassette manifold 3900 is used in conjunction with a sensing probe attached to a house, it may be preferable for sensor ports 3904, 3905, and 3906 to be positioned in the bottom edge of cassette manifold 3900 (the bottom edge as the cassette manifold is shown in FIG. 39). Positioning of the sensor ports 3904, 3905, and 3906 along the bottom edge of exemplary cassette manifold 3900 (such that sensor ports 2904, 3905, and 3906 and installed thermal wells 5100 extend into the bottom fluid line 3903 of the cassette) may facilitate engagement with the sensor apparatus as shown in FIG. 28. In certain of these embodiments, the exemplary cassette manifold 3900 with installed thermal wells 5100 may be placed in position over sensor probes 6000, and then rotated vertically down and onto the sensor probes 6000.

While several geometries have been described, many others could be shown to achieve desired performance characteristics.

The sensing apparatus, in some embodiments, is used to sense conductivity of the subject media within a fluid line within a cassette. In some embodiments, this is in addition to temperature sensing. In those embodiments where both temperature and conductivity sensing is desired, the sensing probe typically includes at least three leads, where two of these leads may be used for temperature sensing and the third used for conductivity sensing.

Referring now to FIG. 21, for conductivity sensing, at least two sensors 7102, 7104 are located in an area containing the subject media. In the embodiment shown, the area containing the subject media is a fluid path 5104 inside a fluid line 5108. The conductivity sensors 7102, 7104 can be one of the various embodiments of sensing probes as described above, or one of the embodiments of the sensor apparatus embodiments (including the thermal well) as described above.

Referring now to FIG. 28, sensing probes 6000 installed in thermal wells 5100 in sensor ports 2305 and 2306 can be used for sensing the conductivity of the subject media located between sensor ports 2305 and 2306 in fluid line 2303. However, in other embodiments, only one of the sensors is one of the embodiments of the sensor apparatus or one of the embodiments of the sensing probe, and the second sensor is any electrical sensor known in the art. Thus, in the systems described herein, conductivity and temperature can be sensed through using either one of the sensor apparatus or one of the sensor probes as described herein and a second capacitance sensor, or one of the sensor apparatus or one of the sensor probes as described herein and an electrical sensor.

For the various embodiments described herein, the cassette may be made of any material, including plastic and metal. The plastic may be flexible plastic, rigid plastic, semi-flexible plastic, semi-rigid plastic, or a combination of any of these. In some of these embodiments the cassette includes one or more thermal wells. In some embodiments one or more sensing probes and/or one or more other devices for transferring information regarding one or more characteristics of such subject media are in direct contact with the subject media. In some embodiments, the cassette is designed to hold fluid having a flow rate or pressure. In other embodiments, one or more compartments of the cassette is designed to hold mostly stagnant media or media held in the conduit even if the media has flow.

In some embodiments, the sensor apparatus may be used based on a need to separate the subject media from the sensing probe. However, in other embodiments, the sensing probe is used for temperature, conductivity, and/or other sensing directly with subject media.

In some embodiments, the thermal well may be part of a disposable portion of a device, machine, system or container. Thus, the thermal well may be in direct contact with subject media and may be the only component that is contaminated by same. In these embodiments, the sensing probe may be part of a machine, device, system or container, and be disposable or non-disposable.

Figure 40:
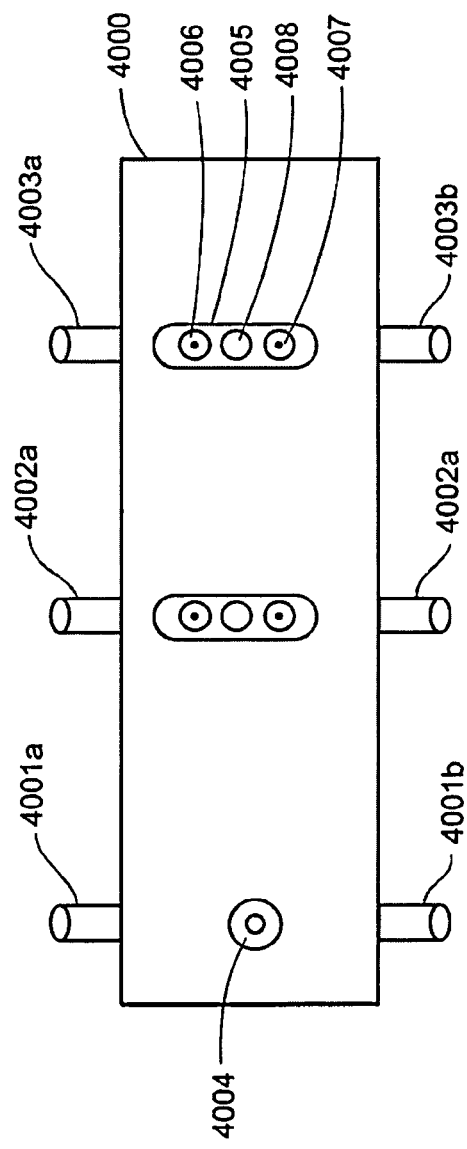
FIG. 40 is a view of another exemplary sensor manifold.

With reference to FIG. 40, another embodiment of an exemplary sensor manifold is shown. A subject media may be contained in or flow through cassette manifold 4000. Subject media may enter cassette manifold 4000 via pre-molded tube connector 4001a and exit the cassette manifold via pre-molded tube connector 4001b. Between tube connector 4001a and 4001b, there is a fluid path though the cassette (not shown) Likewise fluid paths (not shown) extend between tube connectors 4002a and 4002b and 4003a and 4003b.

Referring again to FIG. 40, in this exemplary embodiment of cassettes that may be used in conjunction with the sensor apparatus and sensor apparatus systems described herein, the cassette includes a top plate, a midplate and a bottom plate. Fluid paths, such as the fluid path extending between tube connectors 4001a and 4001b extend through the midplate. In the exemplary embodiment, the cassettes are formed by placing the membranes in their correct locations, assembling the plates in order and laser welding the plates. The cassettes may be constructed of a variety of materials. Generally, in the various exemplary embodiment, the materials used are solid and non flexible. In the preferred embodiment, the plates are constructed of polysulfone, but in other embodiments, the cassettes are constructed of any other solid material and in exemplary embodiment, of any thermoplastic.

Referring now to FIG. 40, in an exemplary embodiment of the cassette manifold, sensors are incorporated into the cassette so as to discern various properties of subject media contained in or flowing through the cassette. In various embodiments one sensor may be included to sense temperature and/or other properties of the subject media. In another embodiment, two sensors may be included, to sense temperature and/or conductivity and/or other properties of the subject media. In yet further embodiments, three or more sensors may be included. In some embodiments, such as sensor element 4004, one sensor element of the type generally described above is included. In other embodiments, the sensors are located in the sensor block 4005. In this embodiment, a sensor block 4005 is included as an area on the cassette manifold for sensor(s), such as temperature sensors and/or conductivity sensors. The conductivity sensors and temperature sensor can be any conductivity or temperature sensor in the art. In one embodiment, the conductivity sensor elements (or sensor leads) are graphite posts. In other embodiments, the conductivity sensors elements are posts made from stainless steel, titanium, or any other material of the type typically used for (or capable of being used for) conductivity measurements. In certain embodiments, the conductivity sensors will include an electrical connection that transmits signals from the sensor lead to a sensor mechanism, controller or other device. In various embodiments, the temperature sensor can be any of the temperature sensors commonly used (or capable of being used) to sense temperature.

However, in alternate embodiments, a combination temperature and conductivity sensor is used of the types described above. In such alternate embodiments, thermal wells of the types described above may be installed in the cassette. In such embodiments, the thermal well may be installed in the cassette by use of any of the ways described herein, including adhesive, welding (ultrasonic and otherwise), o-ring, retaining plate, and otherwise.

Referring now to FIG. 40, two conductivity sensors 4006 and 4007 and the temperature sensor 4008 are shown. In various embodiments, the sensors 4006, 4007, and 4008 are in the fluid path (not shown) that extends between tube connectors 4002a and 4002b and 4003a and 4003b.

3.5. Fluid Handling Systems and Methods Including Sensor Apparatus and Sensor Apparatus Systems Utilized in Connection with a Sensor Manifold In various embodiments of the inventions described herein, systems and methods for fluid handling may be utilized that comprise sensor apparatus systems comprising a sensor manifold. Examples of such embodiments may include systems and methods for the diagnosis, treatment, or amelioration of various medical conditions, including embodiments of systems and methods involving the pumping, metering, measuring, controlling, and/or analysis of various biological fluids and/or therapeutic agents, such as various forms of dialysis, cardio bi-pass, and other types of extracorporeal treatments and therapies. Further examples include fluid treatment and preparation systems, including water treatment systems, water distillation systems, and systems for the preparation of fluids, including fluids utilized diagnosis, treatment, or amelioration of various medical conditions, such as dialysate.

Examples of embodiments of the inventions described herein may include dialysis systems and methods. More specifically, examples of embodiments of the inventions described herein may include hemodialysis systems and methods of the types described in U.S. patent application Ser. No. 11/871,680, filed Oct. 12, 2007 entitled Pumping Cassette; U.S. patent application Ser. No. 12/072,908, filed Feb. 27, 2008 and issued as U.S. Pat. No. 8,246,826 on Aug. 21, 2012 and entitled Hemodialysis System and Methods; and U.S. patent application Ser. No. 12/038,648, filed Feb. 27, 2008 and issued as U.S. Pat. No. 8,042,563 on Oct. 25, 2011 and entitled Cassette System Integrated Apparatus.

In such systems and methods, the utilization of one or more sensor manifolds may allow subject media to be moved from one environment to another environment that is more conducive to obtaining sensor readings. For example, the cassette manifold may be contained in an area that is less subject to various types of environment conditions, such as temperature and/or humidity, which would not be preferable for sensor apparatus such as a sensing probe. Alternatively, sensing apparatus and sensing apparatus system may be delicate and may be more prone to malfunctions than other components of a system. Separating the sensor apparatus and the sensor apparatus systems from other components of the system by use of a sensor manifold may allow the sensing apparatus and sensing apparatus systems to be checked, calibrated, repaired or replaced with minimal impact to other components in the system. The ability to check, calibrate, repair or replace the sensor manifold with minimal impact to the remainder of the system may be particularly advantageous when utilized in connection with the integrated cassette systems and methods described in U.S. patent application Ser. No. 12/072,908, filed Feb. 27, 2008 and issued as U.S. Pat. No. 8,246,826 on Aug. 21, 2012 and entitled Hemodialysis System and Methods and U.S. patent application Ser. No. 12/038,648, filed Feb. 27, 2008 and issued as U.S. Pat. No. 8,042,563 on Oct. 25, 2011 and entitled Cassette System Integrated Apparatus. Alternatively, the sensor manifold may be replaced either more or less frequently than other components of the system.

With reference to FIGS. 41-46, various other embodiments of an exemplary sensor manifold is shown. One or more subject media, preferably a liquid in these exemplary embodiments, may be contained in or flow through cassette manifold 4100. For example, one subject media may enter cassette manifold 4100 via pre-molded tube connector 4101 and exit the cassette manifold via pre-molded tube connector 4102. Between tube connector 4101 and 4102, there is a fluid path though the cassette (best shown as fluid path 4225 in FIG. 42). Likewise fluid paths (shown as fluid paths 4223, 4220, 4222, 4224, and 4221 respectively in FIG. 42) extend between sets of tube connectors 4103 and 4104; 4105 and 4106; 4107, 4108, and 4109; 4110 and 4111; and 4112 and 4113. In certain embodiments, each fluid path may contain subject media of different composition or characteristics. In other embodiments, one or more fluid paths may contain the same or similar subject media. In certain embodiments, the same subject media may be flowed through more than one flow path at the same time to check and/or calibrate the sensor apparatus systems associated with such fluid paths.

Figure 42:
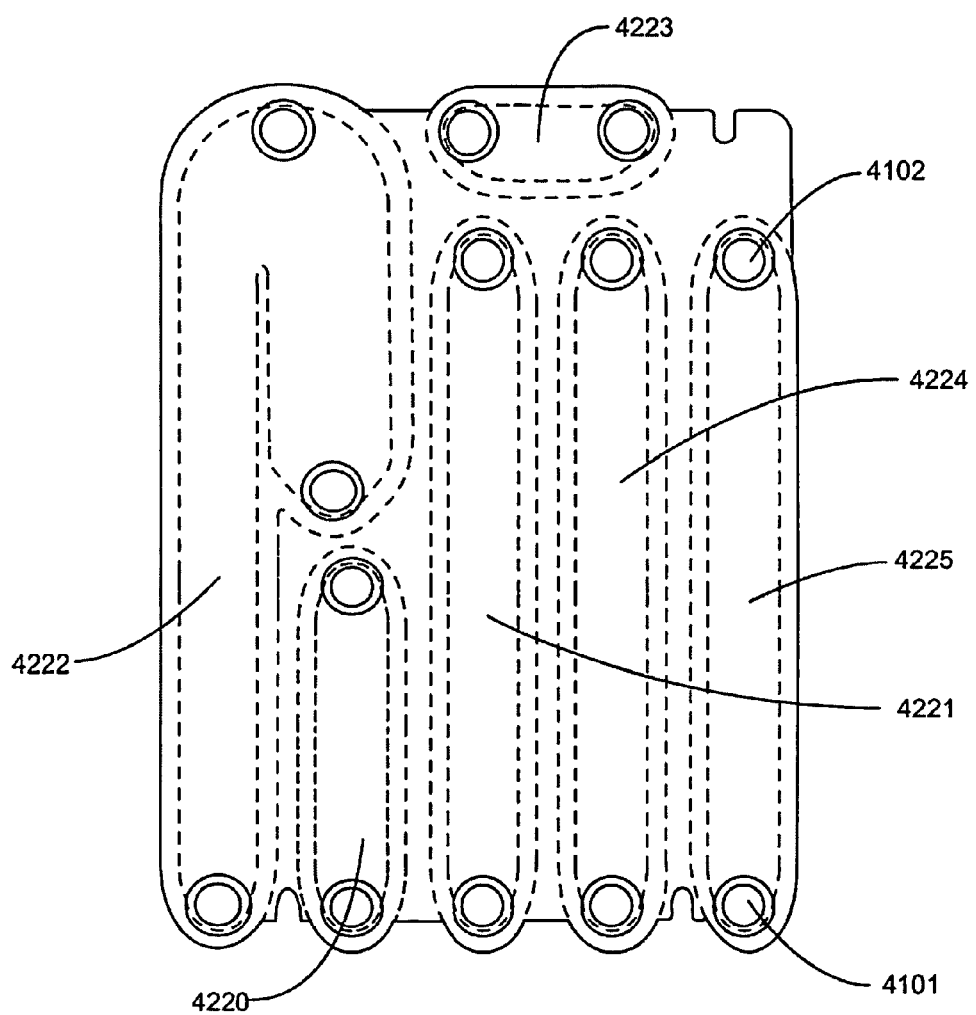
FIG. 42 is a view of the fluid paths within the exemplary sensor manifold shown in FIG. 41.
Figure 43:
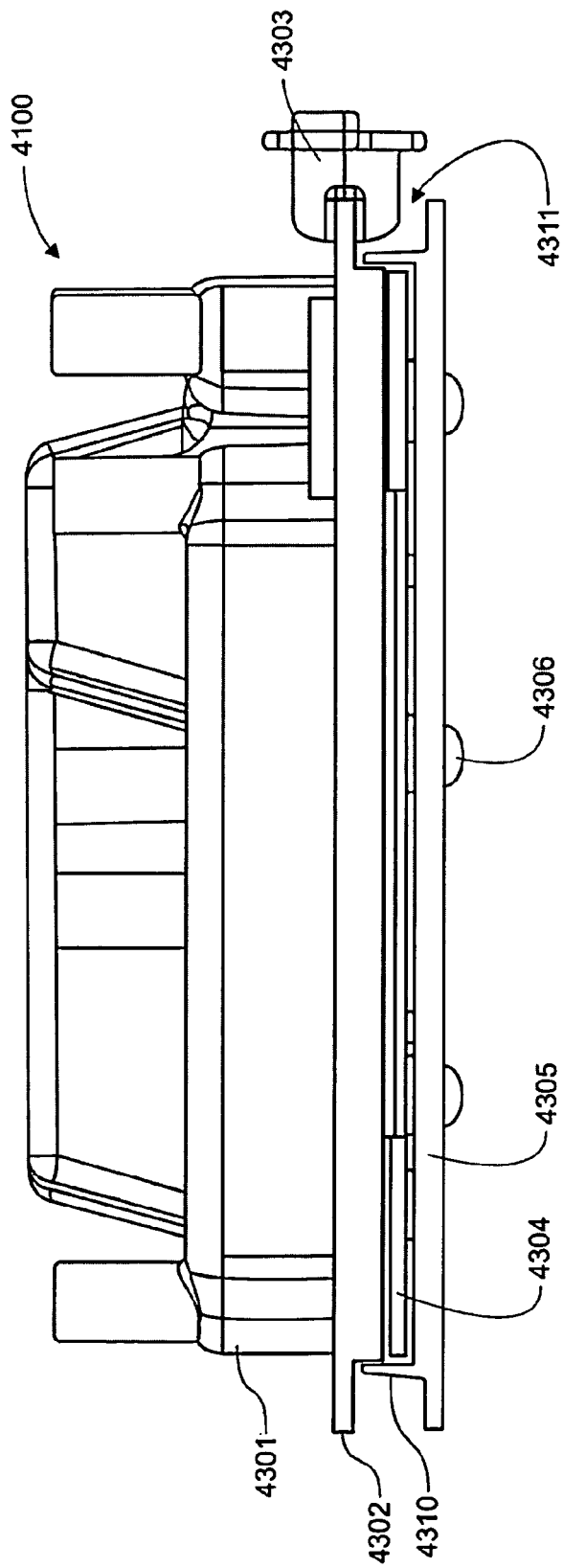
FIG. 43 is a side view of the exemplary sensor manifold shown in FIG. 41.

Referring now to FIG. 43, in these exemplary embodiments of sensor manifold 4100 that may be used in conjunction with the sensor apparatus and sensor apparatus systems described herein, the cassette includes a top plate 4302 and a base 4301. Fluid paths, such as the fluid path 4225 (as shown in FIG. 42) extending between tube connectors 4101 and 4102 extend between the base and top plate. The cassettes may be constructed of a variety of materials. Generally, in the various exemplary embodiment, the materials used are solid and non flexible. In the preferred embodiment, the plates are constructed of polysulfone, but in other embodiments, the cassettes are constructed of any other solid material and in exemplary embodiments, of any thermoplastic. Preferred embodiments of sensor manifold 4100 may be fabricated utilizing the systems and methods described in U.S. patent application Ser. No. 12/038,648, filed Feb. 27, 2008 and issued as U.S. Pat. No. 8,042,563 on Oct. 25, 2011 and entitled Cassette System Integrated Apparatus.

Referring again to FIG. 43, in these exemplary embodiments of sensor manifolds that may be used in conjunction with the sensor apparatus and sensor apparatus systems described herein, the sensor manifold 4100 may also include printed circuit board (PCB) 4304 and a PCB cover 4305. Various embodiments may also include connector 4303 (also shown in FIGS. 41 and 44B) which may be utilized to mechanically connect the cassette manifold 4100 to the system, such as a hemodialysis system. Cassette manifold 4100 may also utilize various means to hold the layers of sensor manifold 4100 together as a unit. In various embodiments, as shown in FIG. 43, connectors 4306 (also shown in FIG. 44B), which in one embodiment is a screw, but in other embodiments may be any means for connection, are utilized, but any means known to one of skill in the art, such as other types of screws, welds, clips, clamps, and other types of chemical and mechanical bonds may be utilized.

Figure 44A:
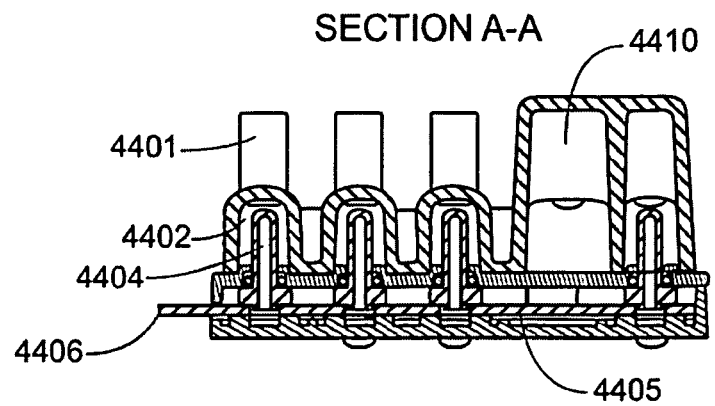
FIG. 44A is a cross sectional view of the exemplary sensor manifold shown in FIG. 41 at cross section A-A of FIG. 44B.

Referring now to FIG. 44A, in exemplary embodiments of the sensor manifold 4100, tube connectors, such as tube connector 4401, is utilized to bring subject media into or remove subject media from fluid path 4402. Sensing probes, such as sensing probe 4404 extending into fluid path 4402, are incorporated into sensor manifold 4100 so as to determine various properties of the subject media contained in or flowing through the particular fluid path in the sensor manifold. In various embodiments one sensing probe may be utilized to sense temperature and/or other properties of the subject media. In another embodiment, two sensing probes may be utilized to sense temperature and/or conductivity and/or other properties of the subject media. In yet further embodiments, three or more sensing probes may be included. In some embodiments, one or more combination temperature and conductivity sensing probes of the types generally described herein may be utilized. In other embodiments, the conductivity sensors and temperature sensor can be any conductivity or temperature sensor in the art. In one embodiment, the conductivity sensor elements (or sensor leads) are graphite posts. In other embodiments, the conductivity sensors elements are posts made from stainless steel, titanium, or any other material of the type typically used for (or capable of being used for) conductivity measurements. In certain embodiments, the conductivity sensors will include an electrical connection that transmits signals from the sensor lead to a sensor mechanism, controller or other device. In various embodiments, the temperature sensor can be any of the temperature sensors commonly used (or capable of being used) to sense temperature.

Figure 41:
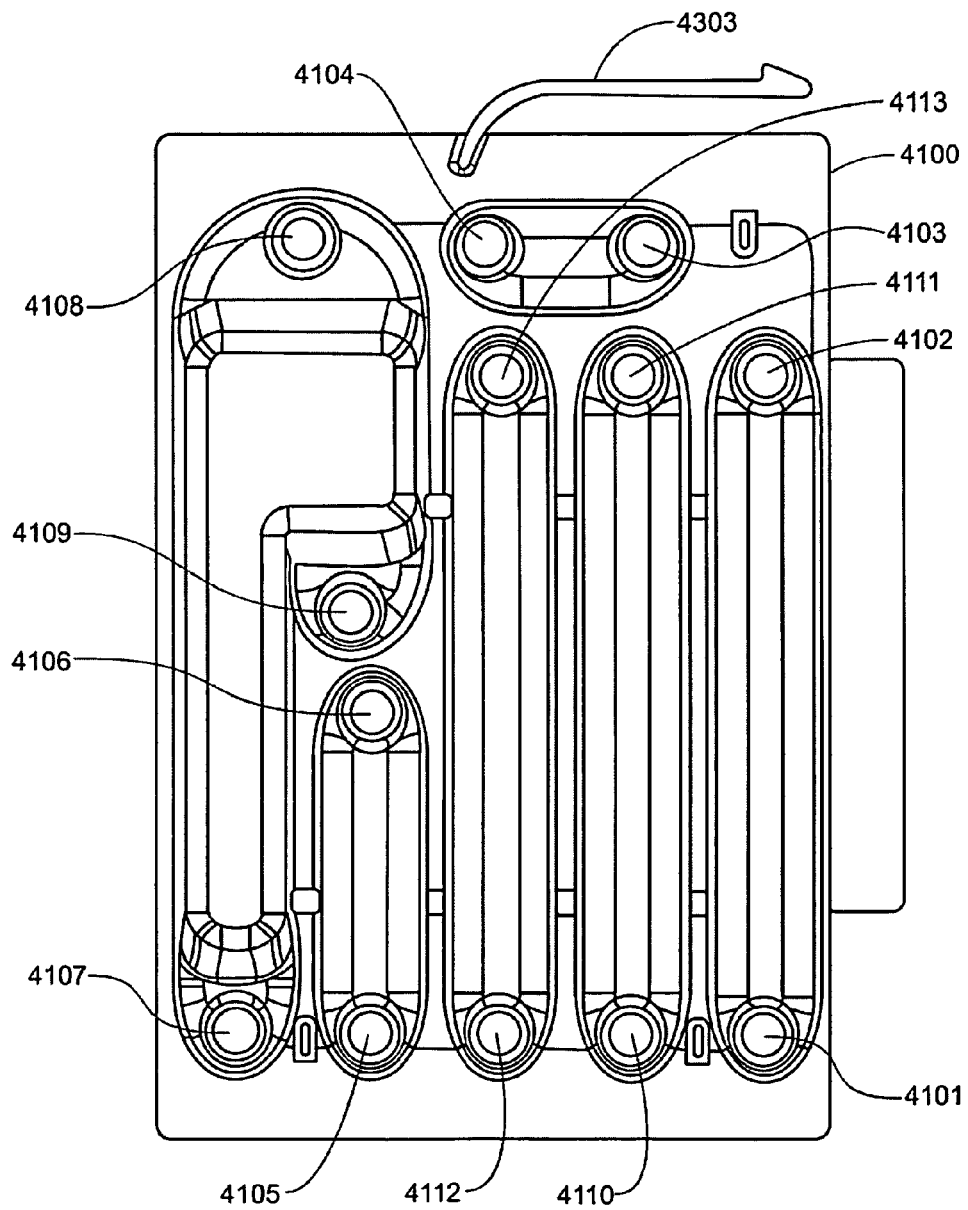
FIG. 41 is a view of another exemplary sensor manifold.

Referring again to FIG. 44A, sensing probe 4404 is electrically connected to PCB 4405. In certain embodiments, an electrically conductive epoxy is utilized between sensor element 4404 and PCB 4405 to ensure appropriate electrical connection, although other means known to those of skill in the art may be used to obtain an appropriate electrical connection between sensor element 4404 and PCB 4405. PCB 4405 is shown with edge connector 4406. In various embodiments, edge connector 4406 may be used to transmit sensor information from cassette manifold 4100 to the main system, such as embodiments of the hemodialysis system described in U.S. patent application Ser. No. 12/072,908, filed Feb. 27, 2008 and issued as U.S. Pat. No. 8,246,826 on Aug. 21, 2012 and entitled Hemodialysis System and Methods. Edge connector 4406 may be connected to a media edge connector (such as media edge connector 4601 shown in FIG. 46). In various embodiments, media edge connector 4601 may be installed in a hemodialysis machine (not shown). In such embodiments, guide tracks 4310 and 4311 (as shown in FIG. 43) may be utilized to assist in the connection of edge connector 4406 and media edge connector 4601. Various embodiments may also include connector 4303 (as shown in FIGS. 41, 43 and 44B) which may be utilized to mechanically connect the cassette manifold 4100 to the system, such as a hemodialysis system.

Referring again to FIG. 44A, air trap 4410 is shown. In certain embodiments, an air trap, such as air trap 4410, may be utilized to trap and purge air in the system. As may be best shown in FIG. 42, subject media may flow through fluid path 4222 between tube connectors 4107 and 4109 in sensor manifold 4100. As the flow of the subject media is slowed around the turn in fluid path 4222 (near tube connector 4108), air may be removed from the subject media through connector 4108.

Figure 44B:
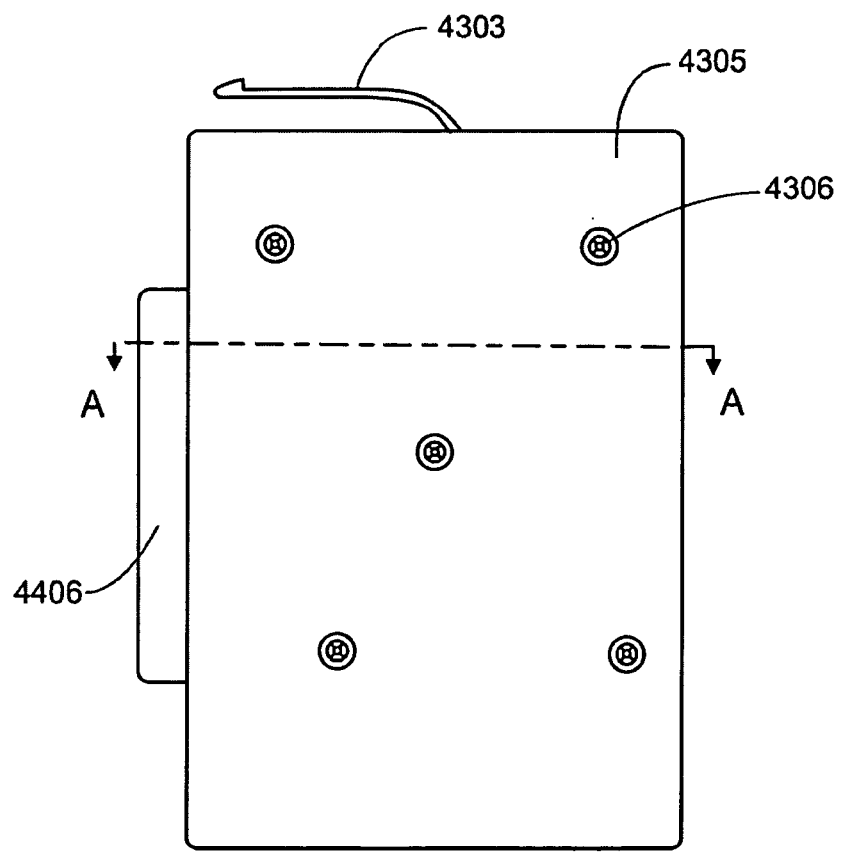
FIG. 44B is a front view of the exemplary sensor manifold shown in FIG. 41.

Referring now to FIG. 44B, PCB cover 4305 is shown. PCB cover 4305 may be connected to sensor manifold 4100 by connectors 4306. Edge connector 4406 is also shown.

In accordance with certain embodiments, sensor manifold 4100 is passive with respect to control of the fluid flow. In such embodiments, sensor manifold 4100 does not contain valves or pumping mechanisms to control the flow of the subject media. In such embodiments, the flow of the subject media may be controlled by fluid control apparatus external to sensor manifold 4100. In other embodiments, the sensor manifold may include one or more mechanical valves, pneumatic valves or other type of valve generally used by those of skill in the art. In such embodiments, the sensor manifold may include one or more pumping mechanisms, including pneumatic pumping mechanisms, mechanical pumping mechanisms, or other type of pumping mechanisms generally used by those of skill in the art. Examples of such valves and pumping mechanisms may include the valves and pumping mechanisms described in U.S. patent application Ser. No. 11/871,680, filed Oct. 12, 2007 entitled Pumping Cassette; U.S. patent application Ser. No. 12/072,908, filed Feb. 27, 2008 and issued as U.S. Pat. No. 8,246,826 on Aug. 21, 2012 and entitled Hemodialysis System and Methods; and U.S. patent application Ser. No. 12/038,648, filed Feb. 27, 2008 and issued as U.S. Pat. No. 8,042,563 on Oct. 25, 2011 and entitled Cassette System Integrated Apparatus.

Figure 45:
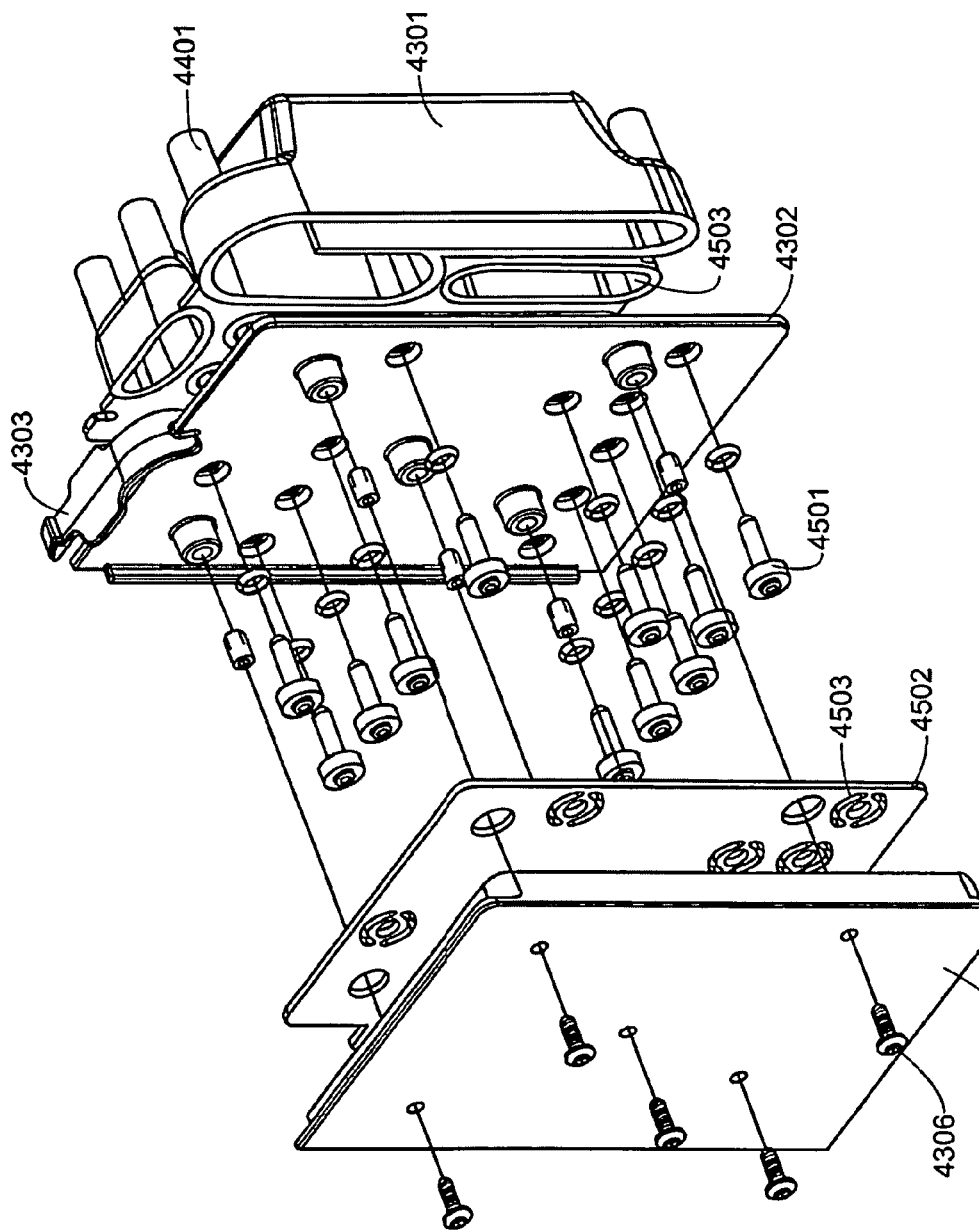
FIG. 45 is an exploded view of the exemplary sensor manifold shown in FIG. 41.
Figure 46:
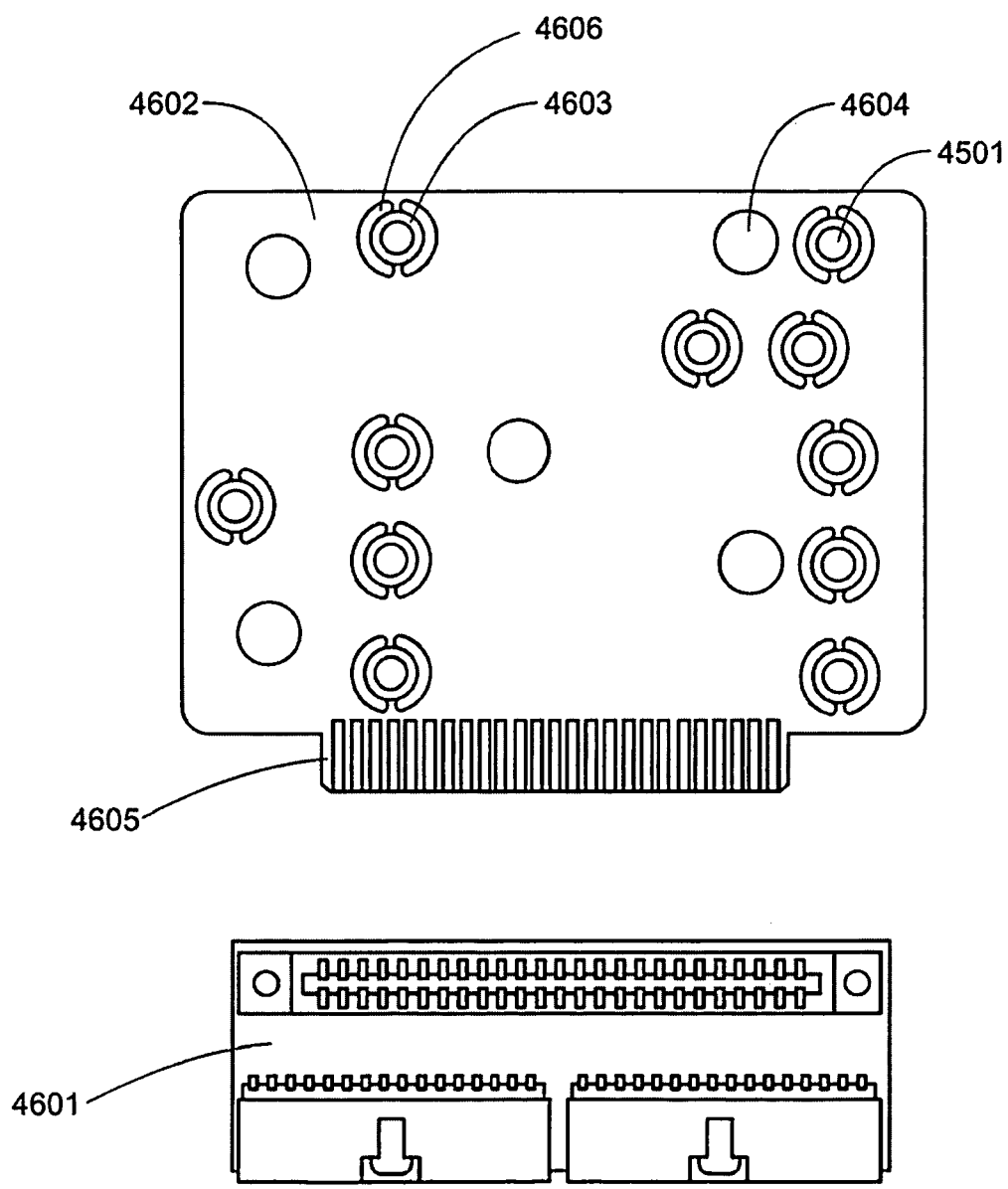
FIG. 46 is a view of a printed circuit board and media edge connector in accordance with the exemplary sensor manifold shown in FIG. 41.

Referring now to FIG. 45, tube connector 4401 is shown in base 4301. Top plate 4302 is shown, along with connector 4303. Sensing probes, such as sensing probe 4501, extend through top plate 4302 into fluid path 4503. Sensing probe 4501 may be various types of sensors, including the embodiments of sensing probes generally shown in FIGS. 8 and 9 herein.

The sensing probes, such as sensing probe 4501, may be all the same, may be individually selected from various sensors based on the type of function to be performed, or the same probe may be individually modified based on the type of function to be performed. Similarly, the configuration of the fluid paths, such as the length of the fluid path and the shape of the fluid path, may be selected based on the function to be performed. By way of example, to detect the temperature of the subject media in a fluid path, a temperature sensor, such as a thermistor, may be used. Again, by way of example, to measure the conductivity of the subject media, one sensing probe configured to measure temperature and conductivity, such as sensing probes of the type generally shown in FIGS. 8 and 9, and one sensing probe configured only to measure conductivity may be utilized. In other embodiments, two or more sensing probes configured to measure both temperature and conductivity, such as sensing probes of the type generally shown in FIGS. 8 and 9, may be utilized. In various embodiments of such configurations, by way of example, the second temperature sensor may be present but not utilized in normal operation, or the second temperature may be utilized for redundant temperature measurements, or the or the second temperature may be utilized for redundant temperature measurements.

Referring again to FIG. 45, PCB 4502 is shown with electrical connection 4503. As further shown in FIG. 46, PCB 4602 is shown with electrical connection 4603 for connection to a sensing probe (shown as 4501 in FIG. 45). PCB 4602 also contains opening 4604 for attachment to top plate (shown as 4305 in FIG. 45). In certain embodiments, electrical connection 4603 is mounted onto, or manufactured with, PCB 4602 with air gap 4606. In such embodiments, air gap 4606 may be utilized to provide protection to the electrical connection between sensing probe 4501 and PCB 4602 by allowing shrinking and expansion of the various components of sensor manifold 4100 with lesser impact to PCB 4602.

Referring again to FIG. 46, PCB 4602 is also shown with edge connector 4605. As described herein, edge connector 4605 may interface with edge connector receiver 4601, which may be connected to the system, such as the hemodialysis system, to which sensor manifold 4100 interfaces.

Figure 47:
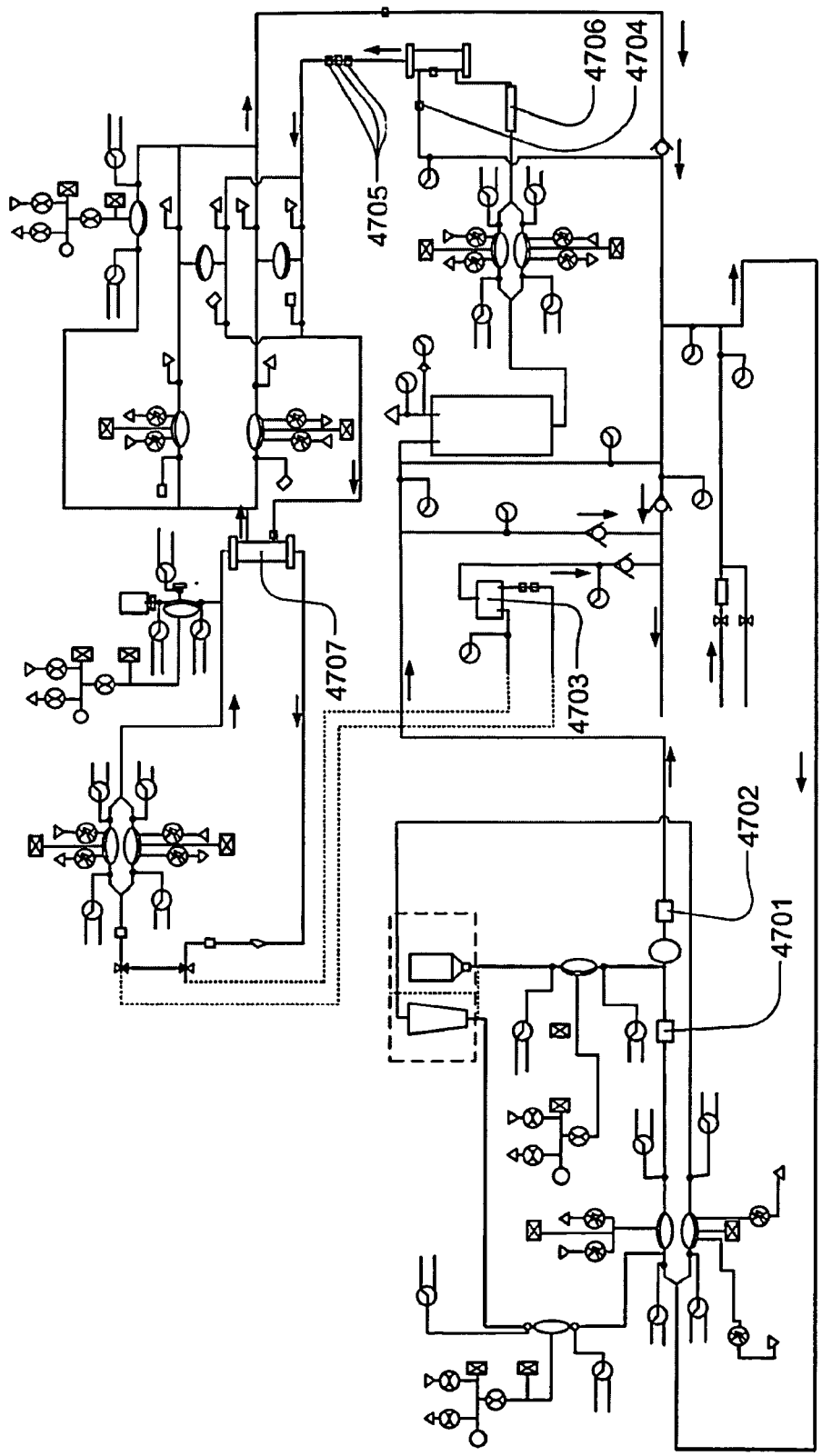
FIG. 47 is an exemplary fluid schematic of a hemodialysis system.

Various embodiments of exemplary sensor manifold 4100 shown in FIG. 41-46 may be utilized in conjunction with hemodialysis systems and methods described in U.S. patent application Ser. No. 11/871,680, filed Oct. 12, 2007 entitled Pumping Cassette; U.S. patent application Ser. No. 12/072,908, filed Feb. 27, 2008 and issued as U.S. Pat. No. 8,246,826 on Aug. 21, 2012 and entitled Hemodialysis System and Methods; and U.S. patent application Ser. No. 12/038,648, filed Feb. 27, 2008 and issued as U.S. Pat. No. 8,042,563 on Oct. 25, 2011 and entitled Cassette System Integrated Apparatus. In certain embodiments, sensor manifold 4100 contains all of the temperature and conductivity sensors shown in FIG. 47. FIG. 47 depicts a fluid schematic in accordance with one embodiment of the inventions described in the patent applications reference above.

By way of example, in various embodiments, the temperature and conductivity of the subject media at position 4701 as shown in FIG. 47 may be determined utilizing sensor manifold 4100. In such embodiments, subject media flows into tube connector 4105 (as shown in FIG. 41) through fluid path 4220 (as shown in FIG. 42) and exits at tube connector 4106 (as shown in FIG. 41). The conductivity of the subject media is measured by two sensing probes (not shown) extending into fluid path 4220, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4701 in FIG. 47, the subject media may be comprised of water to which a bicarbonated based solution has been added. Conductivity of the subject media at position 4701 may be utilized to determine if the appropriate amount of the bicarbonate based solution has been added prior to position 4701. In certain embodiments, if the conductivity measurement deviates from a predetermined range or deviates from a predetermined measurement by more than a predetermined amount, then the subject media may not contain the appropriate concentration of the bicarbonate based solution. In such instances, in certain embodiments, the hemodialysis system may be alerted.

Again, by way of example, in various embodiments, the conductivity of the subject media at position 4702 as shown in FIG. 47 may be determined utilizing sensor manifold 4100. In such embodiments, subject media flows into tube connector 4112 (as shown in FIG. 41) through fluid path 4221 (as shown in FIG. 42) and exits at tube connector 4113 (as shown in FIG. 41). The conductivity of the subject media is measured by two sensing probes (not shown) extending into fluid path 4221, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments at position 4702 in FIG. 47, the subject media may be comprised of water to which a bicarbonated based solution and then an acid based solution has been added. Conductivity of the subject media at position 4702 may be utilized to determine if the appropriate amount of the acid based solution (and the bicarbonate based solution in a previous step) has been added prior to position 4702. In certain embodiments, if the conductivity measurement deviates from a predetermined range or deviates from a predetermined measurement by more than a predetermined amount, then the subject media may not contain the appropriate concentration of the acid based solution and the bicarbonate based solution. In such instances, in certain embodiments, the hemodialysis system may be alerted.

By way of further example, in various embodiments, the temperature and conductivity of the subject media at position 4703 as shown in FIG. 47 may be determined utilizing sensor manifold 4100. In such embodiments, subject media may flow into or out of tube connector 4107 (as shown in FIG. 41) through fluid path 4222 (as shown in FIG. 42) and may flow into or out of tube connector 4109 (as shown in FIG. 41). As described herein, air may be removed from the subject media as it moves past the turn in fluid path 4222. In such instances, a portion of the subject media may be removed through tube connector 4108 to the drain, bringing with it air from the air trap. The conductivity of the subject media is measured by two sensing probes (not shown) extending into fluid path 4222, at least one of which has been configured to include a temperature sensing element, such as a thermistor. The conductivity measurement or the temperature measurement of the subject media may be utilized to determine and/or correlate a variety of information of utility to the hemodialysis system. For example, in various embodiments, the conductivity measurement at position 4703 in FIG. 47 may be utilized to correlate to the clearance of the dialyzer. In such instances, in certain embodiments, this information may then be sent to the hemodialysis system.

Again, by way of further example, in various embodiments, the temperature of the subject media at position 4704 as shown in FIG. 47 may be determined utilizing sensor manifold 4100. In such embodiments, subject media flows into tube connector 4103 (as shown in FIG. 41) through fluid path 4223 (as shown in FIG. 42) and exits at tube connector 4104 (as shown in FIG. 41). The temperature of the subject media is measured by one or more sensing probes (not shown) extending into fluid path 4223. The temperature measurement of the subject media at position 4704 may be utilized to determine and/or correlate a variety of information of utility to the hemodialysis system. For example, in various embodiments at position 4704 in FIG. 47, the temperature of the subject media is determined down stream of a heating apparatus 4706. If the temperature deviates from a predetermined range or deviates from a predetermined measurement by more than a predetermined amount, then the hemodialysis system may be alerted. For example in certain embodiments, the subject media may be re-circulated through the heating apparatus 4706 until the temperature of the subject media is within a predetermined range.

Again, by way of further example, in various embodiments, the temperature and conductivity of the subject media at position 4705 as shown in FIG. 47 may be determined utilizing sensor manifold 4100. In such embodiments, subject media flows into tube connector 4110 (as shown in FIG. 41) through fluid path 4224 (as shown in FIG. 42) and exits at tube connector 4111 (as shown in FIG. 41). The conductivity of the subject media is measured by two sensing probes (not shown) extending into fluid path 4224, at least one of which has been configured to include a temperature sensing element, such as a thermistor. The conductivity measurement or the temperature measurement of the subject media may be utilized to determine and/or correlate a variety of information of utility to the hemodialysis system. For example, the temperature and conductivity measurement at position 4705 may be used as a further safety check to determine if the temperature, conductivity, and, by correlation, the composition of, the subject media is within acceptable ranges prior to the subject media reaching the dialyzer 4707 and, thus, the patient. In certain embodiments, if the temperature and/or conductivity measurement deviates from a predetermined range or deviates from a predetermined measurement by more than a predetermined amount, then the hemodialysis system may be alerted.

For the various embodiments described herein, the cassette may be made of any material, including plastic and metal. The plastic may be flexible plastic, rigid plastic, semi-flexible plastic, semi-rigid plastic, or a combination of any of these. In some of these embodiments the cassette includes one or more thermal wells. In some embodiments one or more sensing probes and/or one or more other devices for transferring information regarding one or more characteristics of such subject media are in direct contact with the subject media. In some embodiments, the cassette is designed to hold fluid having a flow rate or pressure. In other embodiments, one or more compartments of the cassette is designed to hold mostly stagnant media or media held in the conduit even if the media has flow.

In some embodiments, the sensor apparatus may be used based on a need to separate the subject media from the sensing probe. However, in other embodiments, the sensing probe is used for temperature, conductivity, and/or other sensing directly with subject media.

Although the above discussion discloses various exemplary embodiments of the invention, it should be apparent that those skilled in the art can make various modifications that will achieve some of the advantages of the invention without departing from the true scope of the invention. While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

We claim:

1. A dialysis apparatus comprising a cassette for sensing liquid in the dialysis apparatus, the cassette comprising a housing having a plurality of fluid paths, each fluid path including
   a sensor element comprising a well for transmitting temperature and permitting conductivity sensing of fluid passing along the fluid path, wherein the well is adapted for interconnection with a sensor,
   wherein a first fluid flow path of the housing is configured to receive a liquid via a first port and to expel the liquid via a second port located vertically above the first port, and wherein a third port above the first and second ports is arranged to vent gas that escapes from the liquid moving from the first port to the second port.

2. A dialysis apparatus comprising a cassette for sensing liquid in the dialysis apparatus, the cassette comprising a housing having a plurality of fluid paths, each fluid path including
   a sensor element comprising a well for transmitting temperature and permitting conductivity sensing of fluid passing along the fluid path, wherein the well is adapted for interconnection with a sensor,
   wherein a first fluid path of the housing is configured to receive a first mixture of water and a bicarbonate buffer solution, and a second fluid path of the housing is configured to receive a second mixture of completed dialysate comprising the first mixture and an acid or electrolyte concentrate; wherein each fluid path comprises a conductivity sensing probe extending into the fluid path and spaced apart from the well.

3. The dialysis apparatus of claim 2, wherein each sensor is mounted onto and electrically connected with a printed circuit board having an edge connector through which sensor information may be transmitted from the sensors to a system controller.

4. The dialysis apparatus of claim 2, wherein the housing comprises a top plate and a base, the top plate being sealingly engaged with the base to define the volumes of the fluid paths, wherein sensor elements of each sensor penetrate the top plate to extend into the fluid paths.

5. The dialysis apparatus of claim 2, wherein the sensor is a thermistor.

6. The dialysis apparatus of claim 2, wherein said well comprises a hollow housing of a thermally and electrically conductive material, said housing having an outer surface and an inner surface, said inner surface of a predetermined shape so as to form a mating relationship with a sensing probe, wherein said mating thermally and electrically couples the inner surface with the sensing probe.

7. The dialysis apparatus of claim 2, wherein each fluid path comprises a conductivity sensing probe extending into the fluid path and spaced apart from the well.

8. The dialysis apparatus of claim 2, wherein the well is configured to make contact with fluid in the fluid path.

9. The dialysis apparatus of claim 8, wherein the well is coupled to the cassette using at least one of press fit connection, flexible tabs, adhesive, ultrasonic weld, and a retaining plate and fastener.

10. A dialysis apparatus comprising a cassette for sensing liquid in the dialysis apparatus, the cassette comprising a housing having a plurality of fluid paths, each fluid path including a sensor element comprising a well for transmitting temperature and permitting conductivity sensing of fluid passing along the fluid path, wherein a first fluid flow path of the housing is configured to dialysate solution that is flowing to a dialyzer, and a second fluid flow path of the housing is configured to receive dialysate solution directed to drain or to a heating apparatus; wherein each well of the plurality of fluid paths is adapted for interconnection with a thermistor.

11. The dialysis apparatus of claim 10, wherein the plurality of fluid paths each further comprises a conductivity sensing probe extending into the fluid path.

* * * * *